(12) United States Patent
Johnson et al.

(10) Patent No.: US 10,799,594 B2
(45) Date of Patent: Oct. 13, 2020

(54) DRUG DELIVERY POLYMER AND USES THEREOF

(71) Applicant: Massachusetts Institute of Technology, Cambridge, MA (US)

(72) Inventors: Jeremiah A. Johnson, Boston, MA (US); Longyan Liao, Midland, MI (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/231,166

(22) Filed: Dec. 21, 2018

(65) Prior Publication Data

US 2019/0192672 A1    Jun. 27, 2019

Related U.S. Application Data

(62) Division of application No. 15/190,018, filed on Jun. 22, 2016, now Pat. No. 10,159,749, which is a division of application No. 14/249,254, filed on Apr. 9, 2014, now Pat. No. 9,381,253.

(60) Provisional application No. 61/892,957, filed on Oct. 18, 2013, provisional application No. 61/810,065, filed on Apr. 9, 2013.

(51) Int. Cl.
| | |
|---|---|
| *A61K 47/60* | (2017.01) |
| *C07F 15/00* | (2006.01) |
| *A61K 31/4745* | (2006.01) |
| *A61K 31/555* | (2006.01) |
| *A61K 47/58* | (2017.01) |
| *A61K 31/704* | (2006.01) |
| *A61P 35/00* | (2006.01) |

(52) U.S. Cl.
CPC .......... *A61K 47/60* (2017.08); *A61K 31/4745* (2013.01); *A61K 31/555* (2013.01); *A61K 31/704* (2013.01); *A61K 47/58* (2017.08); *A61P 35/00* (2018.01); *C07F 15/0093* (2013.01)

(58) Field of Classification Search
None
See application file for complete search history.

(56) References Cited

U.S. PATENT DOCUMENTS

| | | | |
|---|---|---|---|
| 4,359,425 A | 11/1982 | Totani et al. | |
| 5,811,515 A | 9/1998 | Grubbs et al. | |
| 8,067,505 B2 | 11/2011 | Harris et al. | |
| 9,381,253 B2 | 7/2016 | Johnson et al. | |
| 9,447,129 B2 | 9/2016 | Johnson et al. | |
| 9,822,216 B2 | 11/2017 | Mahanthappa et al. | |
| 10,023,536 B2 | 7/2018 | Johnson et al. | |
| 10,105,449 B2 | 10/2018 | Johnson et al. | |
| 10,159,749 B2 | 12/2018 | Johnson et al. | |
| 10,159,759 B2 | 12/2018 | Johnson et al. | |
| 2002/0183473 A1 | 12/2002 | Matyjaszewski et al. | |
| 2002/0198328 A1 | 12/2002 | L'Alloret | |
| 2003/0065023 A1 | 4/2003 | Swindell et al. | |
| 2005/0109976 A1 | 5/2005 | Fuchs et al. | |
| 2011/0243848 A1 | 10/2011 | Appel et al. | |
| 2011/0300219 A1 | 12/2011 | Lippard et al. | |
| 2013/0296491 A1 | 11/2013 | Xia et al. | |
| 2013/0324666 A1 | 12/2013 | Yan et al. | |
| 2014/0142249 A1 | 5/2014 | Cho et al. | |
| 2014/0308234 A1 | 10/2014 | Johnson et al. | |
| 2015/0225438 A1 | 8/2015 | Johnson et al. | |
| 2016/0024246 A1 | 1/2016 | Mahanthappa et al. | |
| 2016/0289392 A1 | 10/2016 | Grubbs et al. | |
| 2016/0296631 A1 | 10/2016 | Johnson et al. | |
| 2017/0000909 A1 | 1/2017 | Gianneschi et al. | |
| 2017/0073311 A1 | 3/2017 | Johnson et al. | |
| 2017/0348431 A1 | 12/2017 | Johnson et al. | |
| 2018/0030213 A1 | 2/2018 | Johnson et al. | |
| 2018/0036415 A9 | 2/2018 | Johnson et al. | |
| 2018/0094099 A1 | 4/2018 | Johnson et al. | |
| 2019/0030067 A1 | 1/2019 | Johnson et al. | |
| 2019/0038751 A1 | 2/2019 | Johnson et al. | |
| 2019/0038782 A1 | 2/2019 | Johnson et al. | |
| 2019/0054187 A1 | 2/2019 | Johnson et al. | |

FOREIGN PATENT DOCUMENTS

| | | |
|---|---|---|
| CN | 101412792 A | 4/2009 |
| KR | 20120113694 A | 10/2012 |
| WO | WO 2010/047765 A1 | 4/2010 |
| WO | WO 2013/169739 A1 | 11/2013 |
| WO | WO 2014/169073 A1 | 10/2014 |

(Continued)

OTHER PUBLICATIONS

Liao, L., et al., A Convergent Synthetic Platform for Single-Nanoparticle Combination Cancer Therapy: Ratiometric Loading and Controlled Release of Cisplatin, Doxorubicin, and Camptothecin, J. Am. Chem. Soc. 2014, 136, 5896-5899.*
U.S. Appl. No. 16/080,503, filed Aug. 28, 2018, Johnson et al.
PCT/US2017/036447, Dec. 20, 2018, International Preliminary Report on Patentability.
PCT/US2017/055145, Jan. 23, 2018, International Search Report and Written Opinion.
PCT/US2017/055145, Apr. 18, 2019, International Preliminary Report on Patentability.
PCT/US2017/064784, Jun. 20, 2019, International Preliminary Report on Patentability.
PCT/US2017/064784, Mar. 1, 2018, International Search Report and Written Opinion.
PCT/US2017/48641, Nov. 9, 2017, International Search Report.
PCT/US2017/48641, Mar. 7, 2019, International Preliminary Report on Patentability.

(Continued)

*Primary Examiner* — H. Sarah Park
(74) *Attorney, Agent, or Firm* — Wolf, Greenfield & Sacks, P.C.

(57) ABSTRACT

Described herein are platinum-based brush-arm star polymers (Pt-BASPs), or a pharmaceutical composition thereof, for delivery of platinum-based agents, such as cisplatin. Also provided are methods and kits involving the Pt-BASPs, or a pharmaceutical composition thereof, for treating proliferative diseases such as cancers (e.g., lung cancer, head-and-neck cancer, esophagus cancer, stomach cancer, breast cancer, pancreas cancer, liver cancer, kidney cancer, or prostate cancer) in a subject.

20 Claims, 31 Drawing Sheets

(56) References Cited

FOREIGN PATENT DOCUMENTS

WO    WO 2016/023036 A1    2/2016

OTHER PUBLICATIONS

PCT/US2018/040488, Oct. 15, 2018, International Search Report and Written Opinion.
PCT/US2018/040494, Oct. 10, 2018, International Search Report and Written Opinion.
PCT/US2018/040496, Nov. 21, 2018, Invitation to Pay Additional Fees.
PCT/US2018/040496, Jan. 14, 2019, International Search Report and Written Opinion.
PCT/US2018/040488, Jan. 9, 2020, International Preliminary Report on Patentability.
PCT/US2018/040494, Jan. 9, 2020, International Preliminary Report on Patentability.
PCT/US2018/040496, Jan. 9, 2020, International Preliminary Report on Patentability.
International Preliminary Report on Patentability for Application No. PCT/US2017/036447 dated Dec. 20, 2018.
International Search Report and Written Opinion for PCT/US2017/055145, dated Jan. 23, 2018.
International Preliminary Report on Patentability for PCT/US2017/055145, dated Apr. 18, 2019.
International Preliminary Report on Patentability for PCT/US2017/064784, dated Jun. 20, 2019.
International Search Report and Written Opinion for PCT/US2017/064784, dated Mar. 1, 2018.
International Search Report for PCT/US2017/48641, dated Nov. 9, 2017.
International Preliminary Report on Patentability for Application No. PCT/US2017/48641 dated Mar. 7, 2019.
International Search Report and Written Opinion for PCT/US2018/040488, dated Oct. 15, 2018.
International Search Report and Written Opinion for PCT/US2018/040494, dated Oct. 10, 2018.
International Search Report and Written Opinion for Application No. PCT/US2018/040496 dated Jan. 14, 2019.
International Preliminary Report on Patentability for PCT/US2018/040488, dated Jan. 9, 2020.
International Preliminary Report on Patentability for PCT/US2018/040494, dated Jan. 9, 2020.
International Preliminary Report on Patentability for PCT/US2018/040496, dated Jan. 9, 2020.
Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.
Aime et al., Lanthanide(III) chelates for NMR biomedical applications. Chem. Soc. Rev., 1998;27:19-29.
Aime et al., Pushing the sensitivity envelope of lanthanide-based magnetic resonance imaging (MRI) contrast agents for molecular imaging applications. ACC Chem Res. Jul. 21, 2009;42(7):822-31. doi: 10.1021/ar800192p.
Altintas et al., Constructing star polymersvia modular ligation strategies. Polym. Chem., 2012;3:34-45. DOI: 10.1039/C1PY00249J.
Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.
Angot et al., Living Radical Polymerization Immobilized on Wang Resins: Synthesis and Harvest of Narrow Polydispersity Poly(methacrylate)s. Macromolecules, 2001;34(4):768-774. DOI: 10.1021/ma0011690.
Anraku et al., Size-controlled long-circulating PICsome as a ruler to measure critical cut-off disposition size into normal and tumor tissues. Chem Commun (Camb). Jun. 7, 2011;47(21):6054-6. doi: 10.1039/c1cc11465d. Epub Apr. 26, 2011.

Bapat et al., Dynamic-covalent nanostructures prepared by Diels—Alder reactions of styrene-maleic anhydride-derived copolymers obtained by one-step cascade block copolymerization. Polym. Chem., 2012;3:3112-3120. DOI: 10.1039/C2PY20351K.
Bapat et al., Redox-Responsive Dynamic-Covalent Assemblies: Stars and Miktoarm Stars. Macromolecules, 2013;46(6):2188-2198. DOI: 10.1021/ma400169m.
Barner et al., Synthesis of core-shell poly(divinylbenzene) microspheres via reversible addition fragmentation chain transfer graft polymerization of styrene. J. Polym. Sci. A Polym. Chem., 42: 5067-5076. doi:10.1002/pola.20328.
Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.
Bates et al., Polarity-switching top coats enable orientation of sub-10-nm block copolymer domains. Science. Nov. 9, 2012;338(6108):775-9. doi: 10.1126/science.1226046.
Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.
Blencowe et al., Core cross-linked star polymers via controlled radical polymerisation. Polymer Jan. 2009;50(1):5-32.
Blinco et al., Profluorescent Nitroxides as Sensitive Probes of Oxidative Change and Free Radical Reactions. Australian Journal of Chemistry 2010;64(4):373-389. https://doi.org/10.1071/CH10442.
Boase et al., Molecular imaging with polymers. Polym. Chem., Mar. 2012, 1384-1389. DOI: 10.1039/C2PY20132A.
Bobko et al., Reversible reduction of nitroxides to hydroxylamines: roles for ascorbate and glutathione. Free Radic Biol Med. Feb. 1, 2007;42(3):404-12. Epub Nov. 10, 2006.
Bohbot-Raviv et al., Discovering new ordered phases of block copolymers. Phys Rev Lett. Oct. 16, 2000;85(16):3428.
Bolton et al., Synthesis and Melt Self-Assembly of PS—PMMA—PLA Triblock Bottlebrush Copolymers. Macromolecules, 2014;47(9):2864-74. DOI: 10.1021/ma500625k.
Brasch et al., Work in progress: nuclear magnetic resonance study of a paramagnetic nitroxide contrast agent for enhancement of renal structures in experimental animals. Radiology. Jun. 1983;147(3):773-9.
Brasch, Work in progress: methods of contrast enhancement for NMR imaging and potential applications. A subject review. Radiology. Jun. 1983;147(3):781-8.
Brummelhuis et al., Stimuli-responsive star polymers through thiol—yne core functionalization/crosslinking of block copolymer micelles. Polym. Chem., 2011;2:1180-1184. DOI: 10.1039/C1PY00002K.
Budil et al., Nonlinear-Least-Squares Analysis of Slow-Motion EPR Spectra in One and Two Dimensions Using a Modified Levenberg—Marquardt Algorithm. Elsevier. Journal of Magnetic Resonance, Series A. Jun. 1996;120(2):155-189.
Burdynska et al., Synthesis of Star Polymers Using ARGET ATRP. Macromolecules, 2010;43(22):9227-9229. DOI: 10.1021/ma101971z.
Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.
Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.
Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.
Caravan et al., Gadolinium(III) Chelates as MRI Contrast Agents: Structure, Dynamics, and Applications. Chem Rev. Sep. 8, 1999;99(9):2293-352.
Cheng et al., Well-defined diblock macromonomer with a norbornene group at block junction: anionic living linking synthesis and ring-opening metathesis polymerization. Macromol. Mar. 4, 2010;43(7):3153-5.

(56) References Cited

OTHER PUBLICATIONS

Cheon et al., Synergistically integrated nanoparticles as multimodal probes for nanobiotechnology.Acc Chem Res. Dec. 2008;41(12):1630-40. doi: 10.1021/ar800045c.
Chiang et al., Vitamin D for the prevention and treatment of pancreatic cancer. World J Gastroenterol. Jul. 21, 2009;15(27):3349-54.
Choi et al., Self-confirming "AND" logic nanoparticles for fault-free MRI. J Am Chem Soc. Aug. 18, 2010;132(32):11015-7. doi: 10.1021/ja104503g.
Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.
Dag et al., Three-arm star ring opening metathesis polymers via alkyne-azide click reaction. J. Polym. Sci. A Polym. Chem., 47: 2344-2351. doi:10.1002/pola.23324.
Dalsin et al., Bottlebrush block polymers: Quantitative theory and experiments. ACS Nano. Nov. 6, 2015;9(12):12233-45.
Davies et al., Environmentally responsive MRI contrast agents. Chem Commun (Camb). Oct. 28, 2013;49(84):9704-21. doi: 10.1039/c3cc44268c.
Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.
Davis et al., Atom transfer radical polymerization of tert-butyl acrylate and preparation of block copolymers. Macromol. May 30, 2000;33(11):4039-47.
Detappe et al., Advanced multimodal nanoparticles delay tumor progression with clinical radiation therapy. J Control Release. Sep. 28, 2016;238:103-113. doi: 10.1016/j.jconrel.2016.07.021. Epub Jul. 14, 2016.
Ding et al., BRD4 is a novel therapeutic target for liver fibrosis. Proc Natl Acad Sci U S A. Dec. 22, 2015;112(51):15713-8. doi: 10.1073/pnas.1522163112. Epub Dec. 7, 2015.
Doane et al., The unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.
Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.
Elliott et al., Metabolism of brain tissue slices and suspensions from various mammals. J Neurophysiol. Nov. 1984;11(6):473-84.
Feng et al., A metabonomic analysis of organ specific response to USPIO administration. Biomaterials. Sep. 2011;32(27):6558-69. doi: 10.1016/j.biomaterials.2011.05.035.
Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.
Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.
Fox et al., Soluble polymer carriers for the treatment of cancer: the importance of molecular architecture. Acc Chem Res. Aug. 18, 2009;42(8):1141-51. doi: 10.1021/ar900035f.
Frechet, Functional polymers and dendrimers: reactivity, molecular architecture, and interfacial energy. Science. Mar. 25, 1994;263(5154):1710-5.
Gao et al., Development of star polymers as unimolecular containers for nanomaterials. Macromol Rapid Commun. May 14, 2012;33(9):722-34. doi: 10.1002/marc.201200005. Epub Mar. 14, 2012.
Gao et al., Modular Approaches to Star and Miktoarm Star Polymers by ATRP of Cross-Linkers. Macromol. Symp., 291-292: 12-16. doi:10.1002/masy.201050502.
Gao et al., Synthesis of functional polymers with controlled architecture by CRP of monomers in the presence of cross-linkers: From stars to gels. Progress in Polymer Science Apr. 2009;34(4):317-350.

Gao et al., Synthesis of Star Polymers by a New "Core-First" Method: Sequential Polymerization of Cross-Linker and Monomer. Macromolecules, 2008;41(4):1118-1125.
Ge et al., A Pyrene-functionalized Polynorbornene for Ratiometric Fluorescence Sensing of Pyrophosphate. Chem. Asian J. 2016;11:687.
Gestwicki et al., Influencing receptor-ligand binding mechanisms with multivalent ligand architecture. J Am Chem Soc. Dec. 18, 2002;124(50):14922-33.
Glunde et al., Magnetic resonance spectroscopy in metabolic and molecular imaging and diagnosis of cancer. Chem Rev. May 12, 2010;110(5):3043-59. doi: 10.1021/cr9004007.
Godugu et al., Abstract 2139: Effect of telmisartan on triple negative breast cancer (TNBC) and lung cancer tumor progression and intratumoral distribution of nanoparticles. Cancer Res. 2013;73(8).
Goh et al., Highly efficient synthesis of low polydispersity core cross-linked star polymers by Ru-catalyzed living radical polymerization. Macromol Rapid Commun. Mar. 2, 2011;32(5):456-61. doi: 10.1002/marc.201000641. Epub Jan. 7, 2011.
Grahovac et al., Abstract B41: The angiotensin receptor blocker telmisartan inhibits the growth of pancreatic ductal adenocarcinoma and improves survival. Cancer Res. 2016;76(24).
Grason et al., Geometric theory of diblock copolymer phases. Phys Rev Lett. Jul. 31, 2003;91(5):058304.
Haddleton et al., Well-defined oligosaccharide-terminated polymers from living radical polymerization. Biomacromolecules. 2000 Summer;1(2):152-6.
Han et al., Recent Development of Peptide Coupling Reagents in Organic Synthesis. Tetrahedron, 2004;60:2447-2467.
Hao et al., Dendrimers as scaffolds for multifunctional reversible addition—fragmentation chain transfer agents: Syntheses and polymerization. J. Polym. Sci. A Polym. Chem., 2004;42:5877-5890. doi:10.1002/pola.20434.
Harrison et al., A multimeric MR-optical contrast agent for multimodal imaging. Chem Commun (Camb). Oct. 9, 2014;50(78):11469-71. doi: 10.1039/c4cc05651e.
Harrison et al., Multimeric Near IR-MR Contrast Agent for Multimodal In Vivo Imaging. J Am Chem Soc. Jul. 22, 2015;137(28):9108-16. doi: 10.1021/jacs.5b04509. Epub Jul. 14, 2015.
Harvey et al., Lanthanide Complexes as Paramagnetic Probes for 19F Magnetic Resonance. Eur. J. Inorg. Chem., 2012: 2015-2022. doi:10.1002/ejic.201100894.
Hatje et al., Increases in Anthropogenic Gadolinium Anomalies and Rare Earth Element Concentrations in San Francisco Bay over a 20 Year Record. Environ Sci Technol. Apr. 19, 2016;50(8):4159-68. doi: 10.1021/acs.est.5b04322. Epub Jan. 25, 2016.
Hawker et al., Preparation of polymers with controlled molecular architecture. A new convergent approach to dendritic macromolecules. J Am Chem Soc. Oct. 1990;112(21):7638-47.
Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.
Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.
Helms et al., One-Pot Reaction Cascades Using Star Polymers with Core-Confined Catalysts. Angewandte Chemie, 2005;44:6384-6387. doi:10.1002/ange.200502095.
Heroguez et al., Novel Styrene—Butadiene Copolymers by Ring-Opening Metathesis Polymerization. Macromol. Oct. 3, 2000;33(20):7241-8.
Holbrook et al., Gd(III)-Dithiolane Gold Nanoparticles for T1-Weighted Magnetic Resonance Imaging of the Pancreas. Nano Lett. May 11, 2016;16(5):3202-9. doi: 10.1021/acs.nanolett.6b00599. Epub Apr. 20, 2016.
Hoogenboom et al., 1-Lactide Polymerization Utilizing a Hydroxy-Functionalized 3,6-Bis(2-pyridyl)pyridazine as Supramolecular (Co)initiator: Construction of Polymeric [2 × 2] Grids. Macromolecules, 2003;36(13):4743-9. DOI: 10.1021/ma034119e.

(56) References Cited

OTHER PUBLICATIONS

Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.

Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.

Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.

Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.

Hyodo et al., Probing the intracellular redox status of tumors with magnetic resonance imaging and redox-sensitive contrast agents. Cancer Res. Oct. 15, 2016;66(20):9921-8.

Iha et al., Applications of Orthogonal "Click" Chemistries in the Synthesis of Functional Soft Materials. Chem. Rev., 2009;109(11):5620-5686. DOI: 10.1021/cr900138t.

Inglis et al., Well-defined star shaped polymer-fullerene hybrids via click chemistry. Soft Matter, 2010;6:82-84. DOI: 10.1039/B920806M.

Jackson et al., pH triggered self-assembly of core cross-linked star polymers possessing thermoresponsive cores. Chem. Commun., 2011;47:6807-6809. DOI: 10.1039/C1CC11785H.

Jakubowski et al., Activators regenerated by electron transfer for atom transfer radical polymerization of styrene. Macromol. Jan. 10, 2006;39(1):39-45.

Jeong et al., Highly tunable self-assembled nanostructures from a poly (2-vinylpyridine-b-dimethylsiloxane) block copolymer. Nano Lett. Sep. 27, 2011;11(10):4095-101.

Jesberger et al., Hyperbranched polymers as scaffolds for multifunctional reversible addition—fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.

Jiang et al., Morphology and Phase Diagram of Comb Block Copolymer A m+ 1 (BC) m. J Phys Chem B. May 7, 2009;113(21):7462-7.

Jokerst et al., Molecular imaging with theranostic nanoparticles. Acc Chem Res. Oct. 18, 2011;44(10):1050-60. doi: 10.1021/ar200106e. Epub Sep. 15, 2011.

Jokerst et al., Nanoparticle PEGylation for imaging and therapy. Nanomedicine (Lond). Jun. 2011;6(4):715-28. doi: 10.2217/nnm.11.19.

Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.

Jung et al., Orientation-controlled self-assembled nanolithography using a polystyrene—polydimethylsiloxane block copolymer. Nano Lett. Jul. 11, 2007;7(7):2046-50.

Kale et al., Supramolecular assemblies of amphiphilic homopolymers. Langmuir. May 19, 2009;25(17):9660-70.

Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs.6b07670. Epub Sep. 1, 2016.

Kawamoto et al., Loops versus branch functionality in model click hydrogels. Macromol. Dec. 1, 2015;48(24):8980-8.

Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.

Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.

Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel.2013.03.016. Epub Mar. 29, 2013.

Kreutzer et al., Water-Soluble, Unimolecular Containers Based on Amphiphilic Multiarm Star Block Copolymers. Macromolecules, 2006;39(13):4507-4516. DOI: 10.1021/ma060548b.

Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.

Lee et al., Novel phase morphologies in a microphase-separated dendritic polymer melt. Macromol. Jan. 12, 2009;42(3):849-59.

Lee et al., Stimuli-responsive molecular brushes. Progress in Polymer Science (Oxford), 35(1-2), 24-44. DOI: 10.1016/j.progpolymsci.2009.11.002.

Li et al., Polycatechol Nanoparticle MRI Contrast Agents. Small, 2016;12(5):668-677. https://doi.org/10.1002/smll.201502754.

Li et al., A magnetic switch for spin-catalyzed interconversion of nuclear spin isomers. J Am Chem Soc. Mar. 31, 2010;132(12):4042-3. doi: 10.1021/ja910282p.

Li et al., Crosslinking-induced morphology change of latex nanoparticles: A study of RAFT-mediated polymerization in aqueous dispersed media using amphiphilic double-brush copolymers as reactive surfactants. J Polym Sci Part A: Polym Chem. Nov. 15, 2014;52(22):3250-9.

Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.

Li et al., Dynamic cylindrical assembly of triblock copolymers by a hierarchical process of covalent and supramolecular interactions. J Am Chem Soc. Jan. 4, 2011;133(5):1228-31.

Li et al., Efficient synthesis of narrowly dispersed amphiphilic double-brush copolymers through the polymerization reaction of macromonomer micelle emulsifiers at the oil—water interface. Polym Chem. 2016;7(27):4476-85.

Li et al., Facile syntheses of cylindrical molecular brushes by a sequential RAFT and ROMP "grafting-through" methodology. J Polym Sci A Polym Chem. Oct. 15, 2009;47(20):5557-5563.

Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.

Li et al., Synthesis of Hetero-Grafted Amphiphilic Diblock Molecular Brushes and Their Self-Assembly in Aqueous Medium. Macromolecules. 2010;43(3):1182-1184.

Li et al., Well-defined amphiphilic double-brush copolymers and their performance as emulsion surfactants. Macromol. May 18, 2012;45(11):4623-9.

Liang et al., The copper(I)-catalyzed alkyne-azide cycloaddition (CuAAC) "click" reaction and its applications. An overview. Coordination Chemistry Reviews Dec. 2011;255(23-24):2933-2945.

Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.

Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.

Liu et al., Nuts and bolts of chemical exchange saturation transfer MRI. NMR Biomed. Jul. 2013;26(7):810-28. doi: 10.1002/nbm.2899. Epub Jan. 10, 2013.

Liu et al., Synthesis of functional core, star polymers via RAFT polymerization for drug delivery applications. Macromol Rapid Commun. May 14, 2012;33(9):760-6. doi: 10.1002/marc.201200029. Epub Apr. 12, 2012.

Lock et al., One-Component Supramolecular Filament Hydrogels as Theranostic Label-Free Magnetic Resonance Imaging Agents. ACS Nano. Jan. 24, 2017;11(1):797-805.

Love et al., A practical and highly active ruthenium-based catalyst that effects the cross metathesis of acrylonitrile. Angew Chem Int Ed Engl. Nov. 4, 2002;41(21):4035-7.

(56) References Cited

OTHER PUBLICATIONS

Luo et al., Toroidal structures from brush amphiphiles. Chem Commun. 2014;50(5):536-8.

Macrenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.

Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.

Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.

Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.

Matsumoto et al., High-resolution mapping of tumor redox status by magnetic resonance imaging using nitroxides as redox-sensitive contrast agents. Clin Cancer Res. Apr. 15, 2006;12(8):2455-62.

McKenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.

McKenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.

Medarova et al., In vivo imaging of siRNA delivery and silencing in tumors. Nat Med. Mar. 2007;13(3):372-7. Epub Feb. 25, 2007.

Mendichovszky et al., Gadolinium and nephrogenic systemic fibrosis: time to tighten practice. Pediatr Radiol. May 2008;38(5):489-96; quiz 602-3. Epub Oct. 18, 2007.

Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.

Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.

Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 13, 2012.

Moon et al., Targeting the indoleamine 2,3-dioxygenase pathway in cancer J Immunother Cancer. Dec. 15, 2015;3:51. doi: 10.1186/s40425-015-0094-9. eCollection 2015.

Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.

Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.

Mukherjee et al., Oximes as reversible links in polymer chemistry: dynamic macromolecular stars. Polym. Chem., 2014;5:6923-6931. DOI: 10.1039/C4PY01282H.

Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.

Na et al., Development of a T1 contrast agent for magnetic resonance imaging using MnO nanoparticles. Angew Chem Int Ed Engl. 2007;46(28):5397-401.

Na et al., Inorganic Nanoparticles for MRI Contrast Agents. Adv. Mater., 21: 2133-2148. doi:10.1002/adma.200802366.

Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.

Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.

Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer As the Supporting Ligand for Ruthenium-Catalyzed Chemoselective Hydrogen Transfer Reduction of Ketones. Organometallics, 2012;31(14):5074-5080. DOI: 10.1021/om300417v.

Ohno et al., Synthesis of well-defined cyclodextrin-core star polymers. J. Polym. Sci. A Polym. Chem., 39: 2206-2214. doi:10.1002/pola.1197.

Paletta et al., Synthesis and Reduction Kinetics of Sterically Shielded Pyrrolidine Nitroxides. Org. Lett., 2012;14(20):5322-5325. Doi: 10.1021/ol302506f.

Park et al., Star Synthesis Using Macroinitiators via Electrochemically Mediated Atom Transfer Radical Polymerization. Macromolecules, 2013;46(15):5856-5860 Doi: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Perez-Salvia et al., Bromodomain inhibitors and cancer therapy: From structures to applications. Epigenetics. May 4, 2017;12(5):323-339. doi: 10.1080/15592294.2016.1265710. Epub Dec. 2, 2016.

Qiu et al., Efficient and versatile synthesis of star polymers in water and their use as emulsifiers. Chem. Commun., 2011;47:12685-12687. Doi: 10.1039/C1CC15679A.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Rangadurai et al., Temporal and triggered evolution of host-guest characteristics in amphiphilic polymer assemblies. J Am Chem Soc. Jun. 10, 2016;138(24):7508-11.

Rasmussen et al., Improved numerical algorithm for exploring block copolymer mesophases. J Polym Sci Part B: Poly Phys. Aug. 15, 2002;40(16):1777-83.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2010.

Ren et al., Synthetic Strategies towards Well-Defined Complex Polymeric Architectures through Covalent Chemistry. Chemie Ingenieur Technik, 86: 2195-2214. doi:10.1002/cite.201400088.

Rizzo et al., In vivo nanotoxicity testing using the zebrafish embryo assay. J. Mater. Chem. B, Jan. 2013, 3918-3925. DOI: 10.1039/C3TB20528B.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

(56) References Cited

OTHER PUBLICATIONS

Roy et al., Cyclic β-Peptoids. Org. Lett., 2008;10(5):921-924. DOI: 10.1021/ol7030763.
Runge et al., Synthesis and Self-Assembly of Bottlebrush Block Copolymers. PMSEP reprints, 2005;92:5.
Rzayev, Molecular Bottlebrushes: New Opportunities in Nanomaterials Fabrication. ACS Macro Lett., 2012;1(9):1146-1149. DOI: 10.1021/mz300402x.
Rzayev Synthesis of polystyrene—polylactide bottlebrush block copolymers and their melt self-assembly into large domain nanostructures. Macromol. Feb. 20, 2009;42(6):2135-41.
Samuni et al., Factors influencing nitroxide reduction and cytotoxicity in vitro. Antioxid Redox Signal. Jun. 2004;6(3):587-95.
Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.
Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.
Saunders et al., Synthesis of amphiphilic star block copolymers using ring-opening metathesis polymerization. Macromolecules, 1992;25(7):2055-2057. DOI: 10.1021/ma00033a035.
Schmidt et al., Supramolecular three-armed star polymers via cyclodextrin host-guest self-assembly. Polym. Chem., 2012;3:3139-3145. DOI: 10.1039/C2PY20293J.
Sheiko et al., Cylindrical molecular brushes: Synthesis, characterization, and properties. Progress in Polymer Science (Oxford), 33(7), 759-785. DOI: 10.1016/j.progpolymsci.2008.05.001.
Shellock et al., Safety of magnetic resonance imaging contrast agents. J Magn Reson Imaging. Sep. 1999;10(3):477-84.
Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.
Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.
Shin et al., Recent advances in magnetic nanoparticle-based multimodal imaging. Chem Soc Rev. Jul. 21, 2015;44(14):4501-16. doi: 10.1039/c4cs00345d.
Sides et al., Parallel algorithm for numerical self-consistent field theory simulations of block copolymer structure. Polymer. Sep. 1, 2003;44(19):5859-66.
Sinturel et al., High $\chi$-low N block polymers: how far can we go?. ACS Macro Lett. Sep. 2, 2015;4:1044-50.
Smith et al., Nanomaterials for In Vivo Imaging. Chem Rev. Feb. 8, 2017;117(3):901-986. doi: 10.1021/acs.chemrev.6b00073. Epub Jan. 3, 2017.
Sowers et al., Redox-responsive branched-bottlebrush polymers for in vivo MRI and fluorescence imaging. Nature Communications. 2014;5:Article No. 5460.
Spiniello et al., Synthesis and characterization of fluorescently labeled core cross-linked star polymers. J. Polym. Sci. A Polym. Chem., 2008;46:2422-2432. doi:10.1002/pola.22576.
Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.
Sulistio et al., Star polymers composed entirely of amino acid building blocks: a route towards stereospecific, biodegradable and hierarchically functionalized stars. Chem. Commun., 2011;47:1151-1153. DOI: 10.1039/C0CC03541F.
Sveinbjornsson et al., Rapid self-assembly of brush block copolymers to photonic crystals. Proc Natl Acad Sci USA. Sep. 4, 2012;109(36):14332-6. doi: 10.1073/pnas.1213055109. Epub Aug. 21, 2012.
Swaminathan et al., Nephrogenic systemic fibrosis, gadolinium, and iron mobilization. N Engl J Med. Aug. 16, 2007;357(7):720-2.
Takamizu et al., Synthesis of oligo(thiophene)-coated star-shaped ROMP polymers: unique emission properties by the precise integration of functionality. Journal of the American Chemical Society 2012;134(18):7892-7895.
Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.
Terreno et al., Challenges for molecular magnetic resonance imaging. Chem Rev. May 12, 2010;110(5):3019-42. doi: 10.1021/cr100025t.
Theodorakis et al., Interplay between chain collapse and microphase separation in bottle-brush polymers with two types of side chains. Macromol. May 4, 2010;43(11):5137-48.
Thompson et al., Labelling polymers and micellar nanoparticles via initiation, propagation and termination with ROMP. Polym. Chem., 2014;5:1954-1964.
Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.
Tolmasoff et al., Superoxide dismutase: correlation with life-span and specific metabolic rate in primate species. Proc Natl Acad Sci U S A. May 1980;77(5):2777-81.
Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.
Tu et al., Multimodal magnetic-resonance/optical-imaging contrast agent sensitive to NADH. Angew Chem Int Ed Engl. 2009;48(35):6547-51. doi: 10.1002/anie.200900984.
Tunca et al., Novel miktofunctional initiator for the preparation of an ABC-type miktoarm star polymer via a combination of controlled polymerization techniques. J. Polym. Sci. A Polym. Chem., 42: 4228-4236. doi:10.1002/pola.20284.
Valeur et al., Amide bond formation: beyond the myth of coupling reagents. Chem. Soc. Rev., 2009;38:606-631. DOI: 10.1039/B701677H.
Verduzco et al., Correction: Structure, function, self-assembly, and applications of bottlebrush copolymers. Chem Soc Rev. Nov. 7, 2015;44(21):7916. doi: 10.1039/c5cs90099a.
Verduzco et al., Structure, function, self-assembly, and applications of bottlebrush copolymers. Chem. Soc. Rev., 2015;44:2405-20.
Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.
Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.
Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/ol502449r].
Wei et al., Exceedingly small iron oxide nanoparticles as positive MRI contrast agents. Proc. Natl. Acad. Sci. USA 2017;114(9):2325-2330.
Wong et al., Quantitative formation of core cross-linked star polymers via a one-pot two-step single electron transfer-living radical polymerization. Polym. Chem., 2013;4:4562-4565. DOI: 10.1039/C3PY00726J.
Worrell et al., Direct evidence of a dinuclear copper intermediate in Cu(I)-catalyzed azide-alkyne cycloadditions. Science. Apr. 26, 2013;340(6131):457-60. doi: 10.1126/science.1229506. Epub Apr. 4, 2013.
Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.
Xia et al., Efficient Synthesis of Narrowly Dispersed Brush Polymers via Living Ring-Opening Metathesis Polymerization of Macromonomers. Macromolecules, 2009;42(11):3761-3766. DOI: 10.1021/ma900280c.

(56) References Cited

OTHER PUBLICATIONS

Xia et al., EPR study of spin labeled brush polymers in organic solvents. J Am Chem Soc. Dec. 14, 2011;133(49):19953-9. doi: 10.1021/ja2085349. Epub Nov. 21, 2011.

Yang et al., Luminescent chemodosimeters for bioimaging. Chem Rev. Jan. 9, 2013;113(1):192-270. doi: 10.1021/cr2004103. Epub Jun. 18, 2012.

Yi et al., Telmisartan attenuates hepatic fibrosis in bile ductligated rats. Acta Pharmacol Sin. Dec. 2012;33(12):1518-24. doi: 10.1038/aps.2012.115. Epub Oct. 29, 2012.

You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.

Yuan et al., One-pot syntheses of amphiphilic centipede-like brush copolymers via combination of ring-opening polymerization and "click" chemistry. Macromol. Jan. 27, 2010;43(4):1739-46.

Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.

Zhang et al., Dual-functional gadolinium-based copper(II) probe for selective magnetic resonance imaging and fluorescence sensing. Inorg Chem. Feb. 20, 2012;51(4):2325-31. doi: 10.1021/ic202322f. Epub Feb. 8, 2012.

Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.

Zhang et al., Redox-Responsive, Core Cross-Linked Polyester Micelles. ACS Macro Lett., 2013;2(1):40-44. DOI: 10.1021/m7300522n.

Zhao et al., Polystyrene—Polylactide Bottlebrush Block Copolymer at the Air/Water Interface. Macromol. Sep. 28, 2009;42(22):9027-33.

Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.

Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.

Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.

Zheng et al., Construction of Smart Supramolecular Polymeric Hydrogels Cross-linked by Discrete Organoplatinum(II) Metallacycles via Post-Assembly Polymerization. J. Am. Chem. Soc., 2016;138(14):4927-37. DOI: 10.1021/jacs.6b01089.

Zheng et al., Morphology of ABC triblock copolymers. Macromol. Oct. 1995;28(21):7215-23.

Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.

International Search Report and Written Opinion for PCT/US2014/033554, dated Aug. 29, 2014.

International Preliminary Report on Patentability for PCT/US2014/033554, dated Oct. 22, 2015.

Extended European Search Report for EP 14782253.0, dated Nov. 11, 2016.

International Search Report and Written Opinion for PCT/US2015/015032, dated May 8, 2015.

International Preliminary Report on Patentability for Application No. PCT/US2015/015032, dated Aug. 18, 2016.

International Search Report for PCT/US2017/036447, dated Sep. 7, 2017.

Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.

Amouri et al., Host-guest interactions: design strategy and structure of an unusual cobalt cage that encapsulates a tetrafluoroborate anion. Angew Chem Int Ed Engl. Jul. 18, 2005;44(29):4543-6.

Anderson, Late Transition Metal Complexes of Pentafluorophenylphosphino-Pincer Ligands. Doctoral Thesis. Victoria University of Wellington. 2012:ii, iii, 32.

Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.

Aryal et al., Polymeric nanoparticles with precise ratiometric control over drug loading for combination therapy. Mol Pharm. Aug. 1 2011;8(4):1401-7. doi: 10.1021/mp200243k. Epub Jul. 6, 2011.

Barbour et al., An intermolecular (H2O)10 cluster in a solid-state supramolecular complex. Nature. 1998;393(6686): 671-673.

Barnes et al., Using an RNAi Signature Assay to Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. Epub Sep. 14, 2016.

Barrett et al., pH-Based Regulation of Hydrogel Mechanical Properties Through Mussel-Inspired Chemistry and Processing. Advanced Functional Materials. Mar. 6, 2013;23(9):1111-1119.

Beck et al., Multistimuli, multiresponsive metallo-supramolecular polymers. J Am Chem Soc. Nov. 19, 2003;125(46):13922-3.

Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.

Bunzen et al., Self-assembly of M24L48 polyhedra based on empirical prediction. Angew Chem Int Ed Engl. Mar. 26, 2012;51(13):3161-3. doi: 10.1002/anie.201108731.

Burnworth et al., Decoupling Optical Properties in Metallo-Supramolecular Poly (p-phenylene ethynylene)s. Macromolecules. 2008;41(6):2157-2163.

Burts et al., Using EPR to Compare PEG-branch-nitroxide "Bivalent-Brush Polymers" and Traditional PEG Bottle—Brush Polymers: Branching Makes a Difference. Macromolecules. 2012;45(20):8310-18.

Caiolfa et al., Polymer-bound camptothecin: initial biodistribution and antitumour activity studies. J Control Release. Mar. 1, 2000;65(1-2):105-19.

Campos-Fernández et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.

Campos-Fernández et al., Fine-tuning the ring-size of metallacyclophanes: a rational approach to molecular pentagons. J Am Chem Soc. Jan. 31, 2001;123(4):773-4.

Castilla et al., Stereochemistry in subcomponent self-assembly. Acc Chem Res. Jul. 15, 2014;47(7):2063-73. doi: 10.1021/ar5000924. Epub May 2, 2014.

Chambron et al., Topologically complex molecules obtained by transition metal templation: it is the presentation that determines the synthesis strategy. New Journal of Chemistry. 2013;37(1):49-57.

Chand et al., Self-assembly of a novel macrotricyclic Pd(II) metallocage encapsulating a nitrate ion. Chem Commun (Camb). Sep. 7, 2001;(17):1652-3.

Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.

Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.

Chen et al., Synthesis of superporous hydrogels: hydrogels with fast swelling and superabsorbent properties. J Biomed Mater Res. Jan. 1999;44(1):53-62.

(56) References Cited

OTHER PUBLICATIONS

Chifotides et al., Anion-π interactions in supramolecular architectures. Acc Chem Res. Apr. 16, 2013;46(4):894-906. doi: 10.1021/ar300251k. Epub Mar. 11, 2013.

Clever et al., Inclusion of anionic guests inside a molecular cage with palladium(II) centers as electrostatic anchors. Angew Chem Int Ed Engl. 2009;48(38):7010-2. doi: 10.1002/anie.200902717.

Cok et al., Synthesis of Model Network Hydrogels via Tetrazine-Olefin Inverse Electron Demand Diels-Alder Cycloaddition. Macromolecular Symposia. Jul. 2013;329(1):108-112.

Conrad et al., Tunable, temperature-responsive polynorbornenes with side chains based on an elastin peptide sequence. Angew Chem Int Ed Engl. 2009;48(44):8328-30. doi: 10.1002/anie.200903888.

Cordier et al., Self-healing and thermoreversible rubber from supramolecular assembly. Nature. Feb. 21, 2008;451(7181):977-80. doi: 10.1038/nature06669.

Davis et al., Nanoparticle therapeutics: an emerging treatment modality for cancer. Nat Rev Drug Discov. Sep. 2008;7(9):771-82. doi: 10.1038/nrd2614.

Desmarets et al., Design, Self-Assembly, and Molecular Structures of 3D Copper(II) Capsules Templated by BF4—Guest Anions. European Journal of Inorganic Chemistry. Oct. 2009;(29-30):4396-4400. doi: 10.1002/ejic.200900606.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Duncan, The dawning era of polymer therapeutics. Nat Rev Drug Discov. May 2003;2(5):347-60.

Eryazici et al., Two Large-Pore Metal-Organic Frameworks Derived from a Single Polytopic Strut. Crystal Growth & Design. Mar. 7, 2012;12(3):1075-1080.

Forgan et al., Chemical topology: complex molecular knots, links, and entanglements. Chem Rev. Sep. 14, 2011;111(9):5434-64. doi: 10.1021/cr200034u. Epub Jun. 21, 2011.

Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.

Fullenkamp et al., Mussel-Inspired Histidine-Based Transient Network Metal Coordination Hydrogels. Macromolecules. Jan. 18, 2013;46(3):1167-1174.

Gao et al., Synthesis of Acid-Labile PEG and PEG-Doxorubicin-Conjugate Nanoparticles via Brush-First ROMP. ACS Macro Lett. Sep. 16, 2014;3(9):854-857. Epub Aug. 13, 2014.

Gilgorich et al., Palladium-catalyzed reductive coupling of styrenes and organostannanes under aerobic conditions. J Am Chem Soc. Nov. 21, 2007;129(46):14193-5. Epub Oct. 27, 2007.

Greenwald et al., Effective drug delivery by PEGylated drug conjugates. Adv Drug Deliv Rev. Feb. 10, 2003;55(2):217-50.

Grumbley et al., Photoresponsive Polymers Containing Nitrobenzyl Esters via Ring-Opening Metathesis Polymerization. Macromolecules. 2011;44(20):7956-61.

Hackelbusch et al., Chain Dynamics in Supramolecular Polymer Networks. Macromolecules. 2013;46(15):6273-6286.

Hackelbusch et al., Multiresponsive Polymer Hydrogels by Orthogonal Supramolecular Chain Cross-Linking. Macromolecules. 2014;47(12):4028-4036.

Hafkamp et al., Organogel formation and molecular imprinting by functionalized gluconamides and their metal complexes. Chemical Communications. 1997;6:545-546. doi: 10.1039/A608266A.

Hall et al., Platinum(IV) antitumour compounds: their bioinorganic chemistry. Coord Chem Rev. 2002;232:49-67.

Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.

Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.

Harrington et al., Holdfast heroics: comparing the molecular and mechanical properties of Mytilus californianus byssal threads. J Exp Biol. Dec. 2007;210(Pt 24):4307-18.

Harrington et al., Iron-clad fibers: a metal-based biological strategy for hard flexible coatings. Science. Apr. 9, 2010;328(5975):216-20. doi: 10.1126/science.1181044. Epub Mar. 4, 2010.

Harris et al., Giant hollow M(n)L(2n) spherical complexes: structure, functionalisation and applications. Chem Commun (Camb). Aug. 4, 2013;49(60):6703-12. doi: 10.1039/c3cc43191f.

Hirakawa et al., Removal of Perchlorate Anion from an Aqueous Solution by Encapsulation in an Anion-templated Self-assembled Molecular Capsule. Chemistry Letters. 2009;38(3):290-291.

Holliday et al., Strategies for the Construction of Supramolecular Compounds through Coordination Chemistry. Angew Chem Int Ed Engl. Jun. 1, 2001;40(11):2022-2043.

Holten-Andersen et al., Metal-coordination: using one of nature's tricks to control soft material mechanics. J. Mater. Chem. B. 2014;2:2467-2472.

Holten-Andersen et al., pH-induced metal-ligand cross-links inspired by mussel yield self-healing polymer networks with near-covalent elastic moduli. PNAS. Feb. 15, 2011;108:2651-2655.

Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.

Huinink et al., Topotecan versus paclitaxel for the treatment of recurrent epithelial ovarian cancer. J Clin Oncol. Jun. 1997;15(6):2183-93.

Huynh, Novel Polymeric Micelles via RAFT Polymerization for Platinum Drug Delivery. Doctoral Thesis. The University of New South Wales. 2012:i, 57-58.

Jamieson et al., Structure, Recognition, and Processing of Cisplatin-DNA Adducts. Chem Rev. Sep. 8, 1999;99(9):2467-98.

Johnson et al., Core-clickable PEG-branch-azide bivalent-bottle-brush polymers by ROMP: grafting-through and clicking-to. J Am Chem Soc. Jan. 26, 2011;133(3):559-66. doi: 10.1021/ja108441d. Epub Dec. 13, 2010.

Johnson et al., Drug-loaded, bivalent-bottle-brush polymers by graft-through ROMP. Macromolecules. Dec. 28, 2010;43(24):10326-10335.

Johnson et al., Efficient Synthesis of Doxorubicin Releasing Brush Polymers by Graft-Through Romp. Polymer Preprints. 2010;51(2):96-97.

Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.

Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.

Kim et al., Anion-directed self-assembly of coordination polymer into tunable secondary structure. J Am Chem Soc. Jun. 9, 2004;126(22):7009-14.

Kim et al., Supporting Information Experimental Section. J Am Chem Soc. Jun. 9, 2004;126(22):7009-14. Available at: http://pubs.acs.org/doi/suppl/10.1021/ja049799v/suppl_file/ja049799vsi20040219_113203.pdf Retrieved Apr. 24, 2015.

Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20, 2002;124(46):13662-3.

Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.

(56) References Cited

OTHER PUBLICATIONS

Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.

Kwon et al., Block copolymer micelles as long-circulating drug vehicles. Adv Drug Delivery Rev. 1995;16:295-309.

Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 21, 2009.

Lee et al., Mussel-Inspired Adhesives and Coatings. Annu Rev Mater Res. Aug. 1, 2011;41:99-132.

Lee et al., Single-molecule mechanics of mussel adhesion. Proc Natl Acad Sci U S A. Aug. 29, 2006;103(35):12999-3003. Epub Aug. 18, 2006.

Leininger et al., Self-assembly of discrete cyclic nanostructures mediated by transition metals. Chem Rev. Mar. 8, 2000;100(3):853-908.

Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.

Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.

Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n.

Li et al., Surface Properties of Bottlebrush Polymer Thin Films. Macromolecules. 2012;45(17):7118-7127.

Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.

Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t.

Liao et al., A convergent synthetic platform for single-nanoparticle combination cancer therapy: ratiometric loading and controlled release of cisplatin, doxorubicin, and camptothecin. J Am Chem Soc. Apr. 23, 2014;136(16):5896-9. doi: 10.1021/ja502011g. Epub Apr. 11, 2014.

Liao et al., Two-component control of guest binding in a self-assembled cage molecule. Chem Commun (Camb). Jul. 21, 2010;46(27):4932-4. doi: 10.1039/c0cc00234h. Epub Jun. 4, 2010.

Liu et al., Assembly of trigonal and tetragonal prismatic cages from octahedral metal ions and a flexible molecular clip. Inorg Chem. Jul. 23, 2007;46(15):5814-6. Epub Jan. 26, 2007.

Liu et al., Discrete M2L2 metallacycle and M2L4 cage frameworks and anion competitive reactions of Cu2L4 type receptor. Inorganic Chemistry Communications. Jun. 2009;12(6):457-460.

Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.

Liu et al., Particles without a Box: Brush-first Synthesis of Photodegradable PEG Star Polymers under Ambient Conditions. J Vis Exp. 2013;80:e50874, doi:10.3791/50874.

Loveless et al., Chemoresponsive viscosity switching of a metallo-supramolecular polymer network near the percolation threshold. J. Mater Chem. 2007;17:56-61.

Loveless et al., Rational Control of Viscoelestic Properties in Multicomponent Associative Polymer Networks. Macromolecules. 2005;38(24):10171-10177.

Ma et al., Nanoparticles for combination drug therapy. ACS Nano. Nov. 26, 2013;7(11):9518-25. doi: 10.1021/nn405674m.

Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.

Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Moghimi et al., Long-circulating and target-specific nanoparticles: theory to practice. Pharmacol Rev. Jun. 2001;53(2):283-318.

Nair et al., Modulating mechanical properties of self-assembled polymer networks by multi-functional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

Nishiyama et al., Novel cisplatin-incorporated polymeric micelles can eradicate solid tumors in mice. Cancer Res. Dec. 15, 2003;63(24):8977-83.

Peer et al., Nanocarriers as an emerging platform for cancer therapy. Nat Nanotechnol. Dec. 2007;2(12):751-60. doi: 10.1038/nnano.2007.387.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) in patients with solid tumours. Br J Cancer. Feb. 15, 2011;104(4):593-8. doi: 10.1038/bjc.2011.6. Epub Feb. 1, 2011.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.

Sanders et al., Metal-free sequential [3 + 2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sengupta et al., Temporal targeting of tumour cells and neovasculature with a nanoscale delivery system. Nature. Jul. 28, 2005;436(7050):568-72.

Skomski et al., Redox-active on-surface assembly of metal-organic chains with single-site Pt(II). J Am Chem Soc. Jul. 16, 2014;136(28):9862-5. doi: 10.1021/ja504850f. Epub Jul. 1, 2014.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Su et al., Coordination-directed assembly of trigonal and tetragonal molecular boxes encapsulating anionic guests. Journal of the Chemical Society, Dalton Transactions. 2001:359-361. doi: 10.1039/B010118O.

Sun et al., Multicomponent metal-ligand self-assembly. Curr Opin Chem Biol. Dec. 2002;6(6):757-64.

Sun et al., Self-assembled M24L48 polyhedra and their sharp structural switch upon subtle ligand variation. Science. May 28, 2010;328(5982):1144-7. doi:10.1126/science.1188605. Epub Apr. 29, 2010.

Tam et al., Recent advances in metallogels. Chem Soc Rev. Feb. 21, 2013;42(4):1540-67. doi: 10.1039/c2cs35354g. Epub Jan. 8, 2013.

(56) References Cited

OTHER PUBLICATIONS

Tominaga et al., Finite, spherical coordination networks that self-organize from 36 small components. Angew Chem Int Ed Engl. Oct. 25, 2004;43(42):5621-5.
Tsuji et al., Facile Palladium catalyzed decarboxylative allylation of active methylene compounds under neutral conditions using allylic carbonates. Tetrahedron Letters. 1982;23(46):4809-12.
Wang et al., Advances of cancer therapy by nanotechnology. Cancer Res Treat. Mar. 2009;41(1):1-11. doi: 10.4143/crt.2009.41.1.1. Epub Mar. 31, 2009.
Weng et al., Control of Gel Morphology and Properties of a Class of Metallo-Supramolecular Polyers by Good/Poor Solvent Environments. Macromolecules. 2009;42(1):236-246.
Weng et al., Effect of monomer structure on the gelation of a class of metallo-supramolecular polymers. Soft Matter. 2009;5(23):4647-4657.
Weng et al., Structural origin of the thixotropic behavior of a class of metallosupramolecular gels. Tetrahedron. Jul. 30, 2007;63(31):7419-7431.
Weng et al., Understanding the mechanism of gelation and stimuli-responsive nature of a class of metallo-supramolecular gels. J Am Chem Soc. Sep. 6, 2006;128(35):11663-72.
Westhaus et al., Triggered release of calcium from lipid vesicles: a bioinspired strategy for rapid gelation of polysaccharide and protein hydrogels. Biomaterials. Mar. 2001;22(5):453-62.
Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.
Xiao et al., The use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. Epub Aug. 28, 2012.
Xing et al., A stable metal coordination polymer gel based on a calix[4]arene and its 'uptake' of non-ionic organic molecules from the aqueous phase. Chem Commun (Camb). Feb. 21, 2002;(4):362-3.
Xing et al., Design of coordination polymer as stable catalytic systems. Chemistry. Nov. 4, 2002;8(21):5028-32.
Xing et al., Spontaneous Enrichment of Organic Molecules from Aqueous and Gas Phases into a Stable Metallogel. Langmuir. 2002;18:9654-9658.
Xu et al., Mechanism of Shear Thickening in Reversibly Cross-linked Supramolecular Polymer Networks. Macromolecules. Apr. 13, 2010;43(7):3556-3565.
Xu et al., Scaling Laws in Supramolecular Polymer Networks. Macromolecules. 2011;44(13):5465-5472.
Xu et al., Strain Hardening and Strain Softening of Reversibly Cross-linked Supramolecular Polymer Networks. Macromolecules. Sep. 27, 2011;44(18):7478-7488.
Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. Epub Aug. 8, 2013.
Yan et al., Particle carriers for combating multidrug-resistant cancer. ACS Nano. Nov. 26, 2013;7(11):9512-7. doi: 10.1021/nn405632s. Epub Nov. 11, 2013.
Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.
Yan et al., Supramolecular polymers with tunable topologies via hierarchical coordination-driven self-assembly and hydrogen bonding interfaces. Proc Natl Acad Sci U S A. Sep. 24, 2013;110(39):15585-90. doi: 10.1073/pnas.1307472110. Epub Sep. 9, 2013.
Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.
Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.
Yoshizawa et al., Molecular architectures of multi-anthracene assemblies. Chem Soc Rev. Mar. 21, 2014;43(6):1885-98. doi: 10.1039/c3cs60315f.
Yount et al., Small-molecule dynamics and mechanisms underlying the macroscopic mechanical properties of coordinatively cross-linked polymer networks. J Am Chem Soc. Oct. 19, 2005;127(41):14488-96.
Yount et al., Strong means slow: dynamic contributions to the bulk mechanical properties of supramolecular networks. Angew Chem Int Ed Engl. Apr. 29, 2005;44(18):2746-8.
Yue et al., Macrocyclic and lantern complexes of palladium(II) with bis(amidopyridine) ligands: synthesis, structure, and host-guest chemistry. Inorg Chem. Nov. 29, 2004;43(24):7671-81.
Zhang et al., Active cross-linkers that lead to active gels. Angew Chem Int Ed Engl. Oct. 25, 2013;52(44):11494-8. doi: 10.1002/anie.201304437. Epub Sep. 12, 2013.
Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.
Zhao et al., Rheological Behavoir of Shear-Responsive Metallo-Supramolecular Gels. Macromolecules. 2004;37(10):3529-3531.
Zhou et al., Counting primary loops in polymer gels. Proc Natl Acad Sci U S A. Nov. 20, 2012;109(47):19119-24. doi: 10.1073/pnas.1213169109. Epub Nov. 6, 2012.
Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.
U.S. Appl. No. 14/249,254, filed Apr. 9, 2014, Johnson et al.
U.S. Appl. No. 15/190,018, filed Jun. 22, 2016, Johnson et al.
U.S. Appl. No. 14/617,747, filed Feb. 9, 2015, Johnson et al.
U.S. Appl. No. 15/270,959, filed Sep. 20, 2016, Johnson et al.
U.S. Appl. No. 15/616,498, filed Jun. 7, 2017, Johnson et al.
PCT/US2014/033554, Aug. 29, 2014, International Search Report and Written Opinion.
PCT/US2014/033554, Oct. 22, 2015, International Preliminary Report on Patentability.
EP 1478225.0, Nov. 11, 2016, Extended European Search Report.
PCT/US2015/015032, May 8, 2015, International Search Report and Written Opinion.
PCT/US2015/015032, Aug. 18, 2016, International Preliminary Report on Patentability.
PCT/US2017/036447, Sep. 7, 2017, International Search Report.

\* cited by examiner

Camptothecin macromonomer

Doxorubicin macromonomer

Platinum crosslinker

| sample | $M_w$ / kD[a] | $Đ$[b] | <# Bl>[c] | <# Pt>[d] | % 1[e] | $D_H$ / nm[f] | $D_{core}$ / nm[g] |
|---|---|---|---|---|---|---|---|
| *m5N3* | 95 | 1.27 | 5 | 15 | 5% | 11.0(0.4) | 2.1(0.5) |
| *m5N5* | 210 | 1.22 | 10 | 50 | 7% | 11.6(0.3) | 3.3(0.5) |
| *m5N7* | 419 | 1.49 | 18 | 126 | 9% | 16.0(0.2) | 4.2(0.8) |
| *m7N3* | 124 | 1.34 | 5 | 15 | 4% | 12.2(0.3) | 3.5(0.4) |
| *m7N5* | 229 | 1.27 | 8 | 40 | 5% | 15.4(0.4) | 3.9(0.5) |
| *m7N7* | 194 | 1.15 | 7 | 49 | 8% | 14.2(0.6) | 4.0(0.6) |
| *m11N1* | 88 | 1.16 | 2 | 2 | 1% | 11.8(0.6) | 2.8(0.5) |
| *m11N3* | 120 | 1.22 | 3 | 9 | 2% | 13.2(0.5) | 3.2(0.5) |
| *m11N5* | 136 | 1.18 | 3 | 15 | 3% | 13.4(0.3) | 2.7(0.4) |

Figure 4

Camptothecin-Loaded MM (CPT-MM)

Doxorubicin-Loaded MM (Dox-MM)

*Camptothecin-Loaded MM (CPT-MM)*

DRUG DELIVERY POLYMER AND USES THEREOF

RELATED APPLICATIONS

The present application is a division of and claims priority under 35 U.S.C. § 120 to U.S. patent application Ser. No. 15/190,018, filed Jun. 22, 2016, which is a division of and claims priority under 35 U.S.C. § 120 to U.S. patent application Ser. No. 14/249,254, filed Apr. 9, 2014, which claims priority under 35 U.S.C. § 119(e) to U.S. provisional patent application Ser. No. 61/810,065, filed Apr. 9, 2013, and U.S. Ser. No. 61/892,957, filed Oct. 18, 2013, each of which is incorporated herein by reference.

FIELD OF THE INVENTION

This invention relates to polymers and macromolecules for the delivery of therapeutic agents and methods of treating diseases.

BACKGROUND OF THE INVENTION

Platinum-based therapeutics form a cornerstone of treatment for solid tumor malignancies. Cisplatin is one of the most effective chemotherapeutic agents against many forms of cancer including testicular, bladder, head and neck, ovarian, breast, lung, prostate, and refractory non-Hodgkin's lymphomas (Jamieson et al., *Chem Rev.*, 1999, 99:2467-2498). Despite the ubiquitous use of cisplatin in oncology, this drug is associated with significant dose-limiting toxicities including nephrotoxicity and neurotoxicity (Dhar et al., *Proc. Nat. Acad. Sci.*, 2011, 1850-1855). Significant efforts have been devoted to developing new strategies for safer and more effective platinum-based therapeutics therapy.

Targeting controlled release polymer systems (e.g., targeted to a particular tissue or cell type or targeted to a specific diseased tissue but not normal tissue) is desirable because it reduces the amount of a drug present in tissues of the body that are not targeted. This is particularly important when treating cancer where it is desirable that a cytotoxic dose of the drug be delivered to cancer cells without killing the surrounding non-cancerous tissue. Effective drug targeting can reduce the undesirable and sometimes life threatening side effects common with many anti-cancer therapies. Controlled release polymer systems can be designed to provide a drug level in the optimum range over a longer period of time, thus increasing the efficacy of the drug and minimizing problems with patient compliance.

SUMMARY OF THE INVENTION

Platinum-based agents play an important role in the treatment of cancer. Significant adverse reactions related to platinum-based agents frequently hinders the use of higher doses to achieve their maximum antineoplastic effects. The present invention provides platinum-based brush-arm star polymers (Pt-BASP) using "brush-first" ring-opening metathesis polymerization (ROMP). The brush-first method involves sequential copolymerization of two functional monomers, a polymeric macromonomer followed by a multifunctional crosslinker, to generate a unimolecular micelle-like nanostructure with a core including the crosslinker and a corona including the macromonomer (FIGS. 1A-1, 1A-2, and 1B). In certain embodiments, the Pt-BASPs described herein are useful in the delivery and controlled release of platinum-based agents (e.g., platinum-based therapeutic agents). In certain embodiments, the Pt-BASPs can be loaded with more than one therapeutic, diagnostic, or prophylactic agents in addition to the platinum-based agents (e.g., platinum-based therapeutic agents) for multi-agent delivery). In certain embodiments, the platinum-based agent is cisplatin or a cisplatin derivative.

In one aspect, the present invention provides platinum complexes of Formula (I):

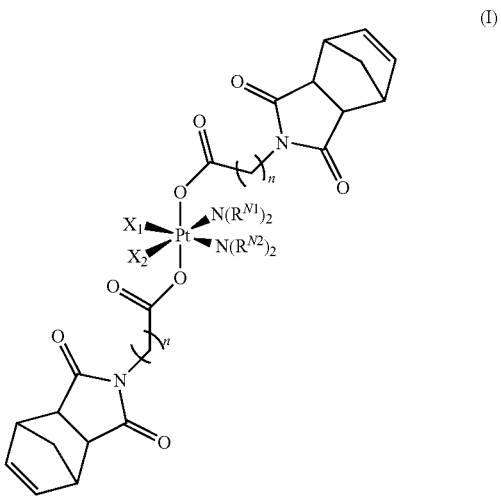

(I)

and salts thereof. In certain embodiments, the platinum complexes of Formula (I), and salts thereof, are prodrugs of a platinum-based therapeutic agent. In certain embodiments, the platinum complexes of Formula (I), and salts thereof, are used as crosslinkers to prepare Pt-BASPs for the delivery of the platinum-based agents. In certain embodiments, a cisplatin-based platinum complex crosslinker is incorporated in BASPs. In certain embodiments, a cisplatin-based platinum complex crosslinker and a macromonomer containing a therapeutic agent are incorporated in the Pt-BASPs (see FIGS. 1A-1 and 1A-2).

In another aspect, the present invention provides methods of preparing platinum complexes of Formula (I) and salts thereof. In certain embodiments, the platinum therapeutic agent is oxidized with an oxidant such as hydrogen peroxide, followed by treatment with a norbornene anhydride derivative.

In another aspect, the present invention provides a macromonomer of Formula (III):

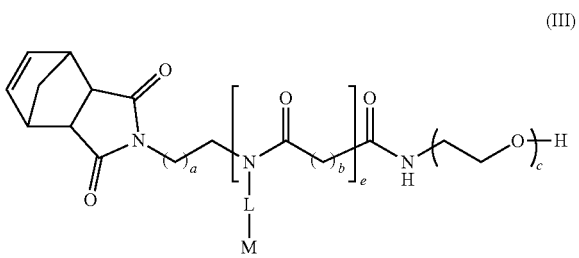

(III)

or a salt thereof. In certain embodiments, macromonomers of Formula (II) include a therapeutic, diagnostic, or prophylactic agent. In certain embodiments, macromonomers of Formula (III) include one or more anti-cancer agents. In certain embodiments, the anti-cancer agent is an alkylating agent (e.g. nitrosoureas; procarbazine; dacarbazine; altretamine; and cisplatin). In certain embodiments, the anti-cancer agent is an antimetabolite (e.g. methotrexate; purine antagonists such as mercaptopurine (6-MP), thioguanine (6-TG), fludarabine phosphate, cladribine and pentostatin; pyrimidine antagonists such as fluorouracil (5-FU), cytarabine (ARA-C) and azacitidine; plant alkaloids such as vinblastine, vincristine, etoposide, teniposide, topotecan, irinotecan, paclitaxel and docetaxel). In certain embodiments, the anti-cancer agent is an antibiotic. In certain embodiments, the anti-cancer agent is an anthracycline, such as doxorubicin or daunorubicin; dactinomycin; idarubincin; plicamycin; mitomycin; or bleomycin. In certain embodiments, the anti-cancer agent is a hormonal agents (e.g. tamoxifen; flutamide; gonadotropin-releasing Hormone Agonistssuch as Leuprolide and Goserelin (Zoladex); aromatase Inhibitors such as aminoglutethimide and anastrozole. In certain embodiments, the anti-cancer agent is amsacrine; ydroxyurea; asparaginase; mitoxantrone; mitotane; retinoic acid derivatives; bone marrow growth factor, or amifostine. In certain embodiments, the anti-cancer agent is camptothecin or another member of the camptothecin family (e.g., topotecan or irinotecan). In certain embodiments, the anticancer agent is doxorubicin.

In another aspect, the present invention provides platinum-based brush-arm star polymers (Pt-BASP) using "brush-first" ring-opening metathesis polymerization (ROMP). In certain embodiments, the Pt-BASP described herein can be prepared by (a) reacting a macromonomer of Formula (III) with a metathesis catalyst to form a polymerization mixture; and (b) mixing the polymerization mixture from step (a) with a solution of a platinum complex of Formula (I). In certain embodiments, the polymer is a brush-arm star polymer (BASP) with the covalently bound platinum-based agent as the core and poly(ethylene glycol) (PEG) as the coronas (FIG. 1B). In certain embodiments, the macromonomer can introduce one or more therapeutic, diagnostic, or prophylactic agents in addition to the platinum-based agent (e.g., platinum-based therapeutic agent). In certain embodiments, the delivery of an agent (including a platinum-based agent) included in a Pt-BASP described herein is ratiometric. In certain embodiments, the delivery of each agent included in a Pt-BASP described herein is ratiometric. In certain embodiments, the release of two or more agents (including a platinum-based agent) included in a Pt-BASP described herein from the Pt-BASP is orthogonal. In certain embodiments, the delivery of two or more agents (including a platinum-based agent) included in a Pt-BASP described herein is orthogonal. In certain embodiments, the macromonomer introduces one or more anti-cancer agents for combination delivery. In certain embodiments, the provided Pt-BASPs are loaded with more than one therapeutic, diagnostic, or prophylactic agents and can be prepared by (a) reacting a macromonomer of Formula (III) having one therapeutic, diagnostic, or prophylactic agent, with another macromonomer of Formula (III) having a different therapeutic, diagnostic, or prophylactic agent, in the presence of a metathesis catalyst to form a polymerization mixture; and (b) mixing the polymerization mixture from step (a) with a solution of a platinum complex of Formula (I). In certain embodiments, the Pt-BASPs as described herein are loaded with cisplatin, camptothecin and doxorubicin (see FIG. 10). In certain embodiments, the Pt-BASPs loaded with cisplatin, camptothecin, and doxorubicin are prepared by (a) reacting a doxorubicin-loaded macromonomer of Formula (III) with a camptothecin-loaded macromonomer of Formula (II) in the presence of a metathesis catalyst to form a polymerization mixture; and (b) mixing the polymerization mixture from step (a) with a solution of a platinum complex of Formula (I).

In another aspect, the present invention provides pharmaceutical compositions comprising a polymer described herein and a pharmaceutically acceptable excipient. In certain embodiments, a polymer described herein is provided as a polymeric nanoparticle. The size of the polymeric nanoparticle may be determined by the molar ratio of all the macromonomers to the crosslinker employed in a method of preparing the polymeric nanoparticle (e.g., Method A or B). In certain embodiments, the polymeric nanoparticle is of radius size about 1 nm to about 1000 nm. In certain embodiments, the polymeric nanoparticle is of radius size about 1 nm to about 200 nm. In certain embodiments, the polymeric nanoparticle is of radius size about 1 nm to about 20 nm. In certain embodiments, the polymeric nanoparticle is of radius size about 1 nm to about 10 nm. In certain embodiments, the pharmaceutical compositions described herein include a therapeutically effective amount of a polymer described herein. The pharmaceutical composition may be useful for treating a proliferative disease such as cancer.

In another aspect, the present invention provides methods for treating proliferative diseases. Exemplary proliferative diseases include cancers (e.g., leukemia, melanoma, multiple myeloma, solid tumors), benign neoplasms, angiogenesis, angiogenesis-associated diseases, inflammatory diseases, autoinflammatory diseases, and autoimmune diseases.

In another aspect, the present invention provides kits comprising a platinum complex of Formula (I) and/or a polymer described herein. The kits of the invention may include a single dose or multiple doses of a platinum complex of Formula (I) and/or a polymer described herein. The provided kits may be useful for the treatment of proliferative diseases such as cancers. In certain embodiments, the kits described herein further include instructions for administering the platinum complex of Formula (I) and/or a polymer described herein. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

The details of certain embodiments of the invention are set forth herein. Other features, objects, and advantages of the invention will be apparent from the Detailed Description, Figures, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; *Smith and March March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-5}$, $C_{2-5}$, $C_{2-4}$, $C_{2-3}$, $C_{3-4}$, $C_{3-5}$, $C_{3-4}$, $C_{4-6}$, $C_{4-5}$, and $C_{5-6}$ alkyl.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_2$ 6 alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

The term "heteroalkyl" refers to an alkyl group which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_2$-10 alkynyl.

The term "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{1-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, carbocyclyl, aryl, and heteroaryl groups are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" carbocyclyl. "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O) SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein. In the case wherein "substituted hydroxyl" is a ligand L$_1$ or L$_2$, "substituted hydroxyl" also refers to the group (R$^{aa}$)$_2$O, wherein R$^{aa}$ is as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$.

The term "monosubstituted amino" refers to an amino group wherein the nitrogen atom directly attached to the parent molecule, or coordinated to an iron atom, is substituted with one hydrogen and one group other than hydrogen, and includes groups selected from —NH(R$^{bb}$). —NHC(=O)R$^{aa}$—, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule, or coordinated to an iron atom, is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule, or coordinated to an iron atom, is substituted with three groups, and includes groups selected from —N(R$^{bb}$)$_3$ and —N(R$^{bb}$)$_3$+X$^-$, wherein R$^{bb}$ and X$^-$ are as defined herein.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl. C$_{2-10}$ alkynyl. C$_{1-10}$ heteroalkyl. C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition. John Wiley & Sons, 1999, incorporated herein by reference.

For example, nitrogen protecting groups such as amide groups (e.g., —C(O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC). 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methylencamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris (levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(RN)_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

The use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

Other Definitions

The following definitions are more general terms used throughout the present application:

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

A "polymer" is given its ordinary meaning as used in the art, i.e., a molecular structure comprising one or more repeat units (monomers), connected by covalent bonds. The repeat units may all be identical, or in some cases, there may be more than one type of repeat unit present within the polymer. In certain embodiments, the polymer has C═C. In certain embodiments, the polymer is prepared from ring opening metathesis polymerization.

The term "cross-linker" refers to compounds that link one polymer chain to another by covalent bonds or ionic bonds. "Polymer chains" can refer to synthetic polymers or natural polymers (such as proteins).

The term "macromonomer" refers to a macromolecule with one end-group that enables it to act as a monomer. Macromonomers will contribute a single monomeric unit to a chain of the completed macromolecule.

The term "prodrugs" refer to compounds and/or polymers, including compounds of Formula (I) and polymers of Formula (II), which have cleavable groups and become active by solvolysis, reduction, oxidation, or under physiological conditions, to provide the pharmaceutically active compounds in vivo. Prodrugs include polymeric derivatives conjugated with the pharmaceutical active compounds known to practitioners of the art, such as, for example, to form an ester by reaction of the acid, or acid anhydride, or mixed anhydrides moieties of the polymer of the polymer with the hydroxyl moiety of the pharmaceutical active compound, or to form an amide prepared by the acid, or acid anhydride, or mixed anhydrides moieties of the polymer with a substituted or unsubstituted amine of the pharmaceutically active compound. Simple aliphatic or aromatic esters, amides, and anhydrides derived from acidic groups pendant on the polymers of this invention are particular prodrugs. In some embodiments, the polymer incorporates one therapeutic agent. In some embodiments, the polymer incorporates more than one therapeutic agents.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic or genetically engineered animal.

The terms "administer," "administering," or "administration" refer to implanting, absorbing, ingesting, injecting, inhaling, or otherwise introducing an inventive polymer, or a pharmaceutical composition thereof, or a device incorporating the inventive polymer.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of refers to an amount sufficient to elicit a desired biological response, i.e., treating the condition. As will be appreciated by those of ordinary skill in this art, the effective amount of an inventive polymer may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor. In treating macular degeneration, an effective amount of an inventive compound may improve sight, reduce the risk of vision loss, or prevent central vision loss from worsening.

A "therapeutically effective amount" is an amount sufficient to provide a therapeutic benefit in the treatment of a condition or to delay or minimize one or more symptoms associated with the condition. A therapeutically effective amount of an inventive polymer means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant." depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary.* 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer, benign monoclonal gammopathy; biliary cancer (e.g., cholangiocarcinoma); bladder cancer, breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML. T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLUSLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer, rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and growth of new blood vessels. Normal angiogenesis occurs in the body of a healthy subject during wound healing and for restoring blood flow to tissues after injury. The body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can result in new blood vessels that feed diseased tissues and/or destroy normal tissues, and in the case of cancer, the new vessels can allow tumor cells to escape into the circulation and lodge in other organs (tumor metastases).

The term "ratiometric" refers to the situation where $C_1^i$ is substantially equal to $C_0^i$, wherein $C_0^i$ refers to the ratio of the amount of a first agent before the first agent is delivered to a subject, tissue, or cell, to the total amount of two or more agents (including the first agent) before the two or more agents are delivered to the subject, tissue, or cell; and $C_1^i$ refers to the ratio of the amount of the first agent that is delivered to the subject, tissue, or cell, to the total amount of the two or more agents (including the first agent) that are delivered to the subject, tissue, or cell. In certain embodiments, the delivery of each one of the two or more agents is ratiometric.

The term "orthogonal" refers to the situation where a first agent and a second agent, each of which is included in a Pt-BASP described herein, is independently released from the Pt-BASP. In certain embodiments, under condition A, the first agent, but not the second agent, is released from the Pt-BASP. For example, an orthogonal release or orthogonal delivery of the first and second agents includes: under condition A, the first agent, but not the second agent, is released from the Pt-BASP; under condition B, the second agent, but not the first agent, is released from the Pt-BASP. The release or delivery of the first and second agents is not orthogonal when, for example, under condition C, both the first and second agents are released from the Pt-BASP.

BRIEF DESCRIPTION OF THE DRAWINGS

FIG. 2 shows an exemplary synthesis of platinum brusharm star polymers (Pt-BASPs) with cisplatin prodrug crosslinker XL3. PEG-based macromonomer (MM) 4 (in equiv.) is first exposed to 1.0 equiv, of catalyst C-1 (cat.) in tetrahydrofuran for 10 min to generate living bottle-brush polymer initiators (BIs). Transfer of the BI solution to solid XL3 initiates crosslinking and formation of Pt-BASPs with dense Pt-loaded cores and PEG coronas. Upon reduction, cleavage of the O—Pt bonds from XL3 leads to simultaneous Pt-BASP degradation and release of the platinum-based therapeutic agent such as cisplatin.

FIG. 4 shows Table 1 of characterization data for Pt-BASPs. The hydrodynamic diameters ($D_H$) of each Pt-BASP were measured by dynamic light scattering (DLS). Values for $D_H$ ranged from 11.0±0.4 nm to 16.0±0.2 nm, and generally increased with MW (Table 1). Since $D_H$ captures the size of the Pt-BASP plus its hydrated shell, $D_H$ values can be larger than the diameters measured by TEM. In the case of the m5N5 sample, the $D_H$ value is of 11.6±0.3 and the TEM value is 9.3±0.9.

FIGS. 3-4 demonstrate that the Pt-BASP sizes and Pt loadings can be tuned by adjusting m and N. Increasing m (BI length) generally increases steric bulk and limits the extent of crosslinking; shorter BIs (smaller m) generally lead to larger Pt-BASPs. Increasing N (Pt loading) generally directly increases the core size and reduces steric hindrance, which leads to increased <# BI>.

As shown in FIG. 5C, the Pt-BASP (squares) had an $IC_{50}$=37 µM; cisplatin (circles) had an $IC_{50}$=23 µM. The same kinetics for the cell culture experiment is assumed, then the dose-response curve for the Pt-BASP is shifted to lower concentration to give an $IC_{50}$=14 µM (triangles, m5N5*, star suggests identifying a different curve (the curve shifted to lower IC50)). The observation that Pt-BASPs display similar $IC_{50}$ values to cisplatin, but only 18-39% of the Pt is released, suggesting that at least a fraction of the Pt-BASP material is internalized. Addition of ligands to the PEG periphery that induce internalization may lead to even greater efficacy.

DETAILED DESCRIPTION OF CERTAIN EMBODIMENTS OF THE INVENTION

Figures 1, 1A:
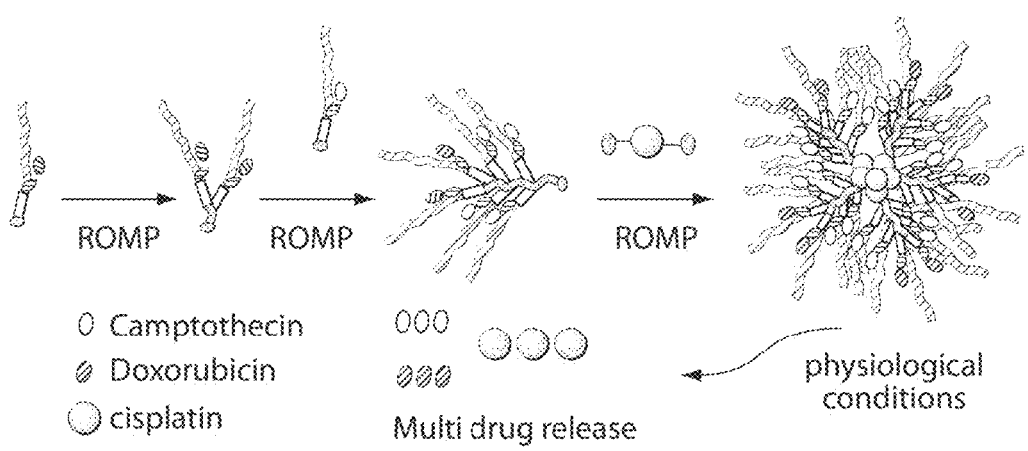
FIGS. 1A-1 and 1A-2 show an exemplary synthesis of Pt-BASPs loaded with more than one therapeutic agents.
Figure 1A:
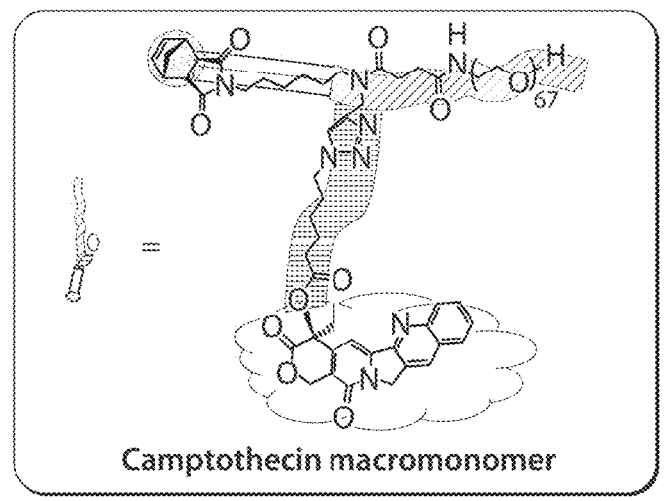
Figure 1:
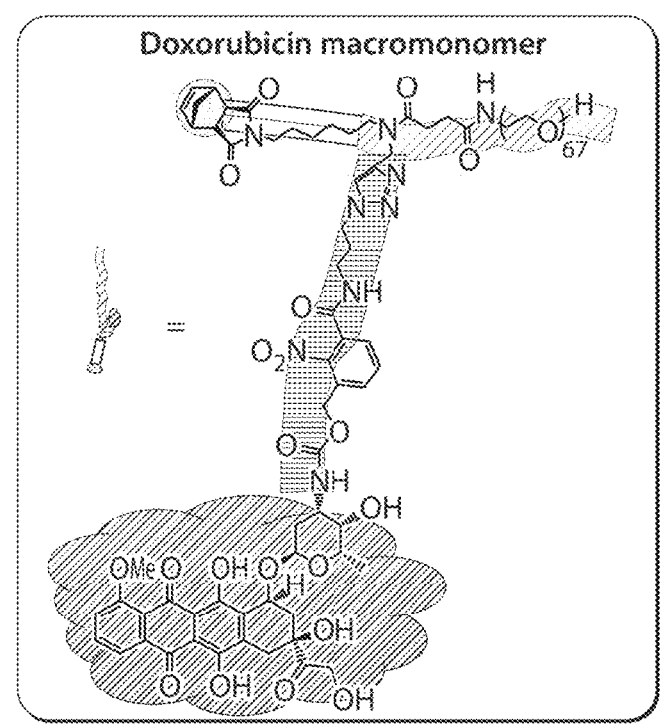

Platinum-based agents are widely used in cancer chemotherapy. Significant adverse reactions related to platinum-based agents frequently hinder the use of higher doses to achieve their maximum antineoplastic effects. The present invention provides platinum-based brush-arm star polymers (Pt-BASPs) and methods for the controlled delivery of platinum-based therapeutic agents. In certain embodiments, the Pt-BASPs are loaded with more than one therapeutic, diagnostic, or prophylactic agents in addition to the platinum-based therapeutic agents for multi-agent delivery.

Platinum Complex Crosslinkers

In one aspect, the present invention provides a platinum complex of Formula (I):

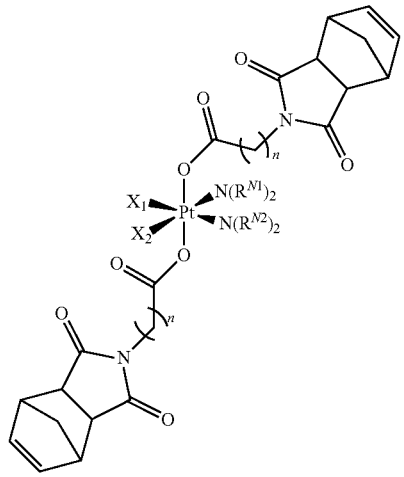

(I)

or a salt thereof,
wherein:

$X_1$ is F, Cl, Br, or I;

$X_2$ is F, Cl, Br, or I;

each instance of $R^{N1}$ and $R^{N2}$ is independently hydrogen, optionally substituted $C_{1-6}$ alkyl, or a nitrogen protecting group; or two $R^{N1}$ are taken with the intervening atoms to form a heterocyclic ring; or two $R^{N2}$ are taken with the intervening atoms to form a heterocyclic ring; or $R^{N1}$ and $R^{N2}$ are taken with the intervening atoms to form a heterocyclic ring; and n is 1, 2, 3, 4, 5, or 6.

As generally defined herein, $X_1$ is F, Cl, Br, or I. In certain embodiments, $X_1$ is F. In certain embodiments, $X_1$ is Cl. In certain embodiments, $X_1$ is Br. In certain embodiments, $X_1$ is I.

As generally defined herein, $X_2$ is F, Cl, Br, or I. In certain embodiments, $X_2$ is F. In certain embodiments, $X_2$ is Cl. In certain embodiments, $X_2$ is Br. In certain embodiments, $X_2$ is I.

In certain embodiments, $X_1$ and $X_2$ are the same. In certain embodiments, $X_1$ and $X_2$ are F. In certain embodiments, $X_1$ and $X_2$ are Cl. In certain embodiments, $X_1$ and $X_2$ are Br. In certain embodiments, $X_1$ and $X_2$ are I. In certain embodiments, $X_1$ and $X_2$ are different. In certain embodiments, $X_1$ is Cl, and $X_2$ is F. In certain embodiments, $X_1$ is Cl, and $X_2$ is Br. In certain embodiments, $X_1$ is Cl, and $X_2$ is I. In certain embodiments, $X_1$ is Br, and $X_2$ is I. In certain embodiments, $X_1$ is F, and $X_2$ is I. In certain embodiments, $X_1$ is F, and $X_2$ is Br.

As generally defined herein, each instance of $R^{N1}$ is independently hydrogen, optionally substituted $C_{1-6}$ alkyl, or a nitrogen protecting group, or two $R^{N1}$ are taken with the intervening atoms to form a heterocyclic ring. In certain embodiments, $R^{N1}$ is nitrogen. In certain embodiments, $R^{N1}$ is optionally substituted $C_{1-6}$ alkyl. In certain embodiments, $R^{N1}$ is substituted $C_{1-6}$ alkyl. In certain embodiments, $R^{N1}$ is unsubstituted $C_{1-6}$ alkyl. In certain embodiments, $R^{N1}$ is methyl. In certain embodiments, $R^{N1}$ is ethyl. In certain embodiments, $R^{N1}$ is a nitrogen protecting group. In certain embodiments, two $R^{N1}$ are taken with the intervening atoms to form a heterocyclic ring.

As generally defined herein, each instance of $R^{N2}$ is independently hydrogen, optionally substituted $C_{1-6}$ alkyl, or a nitrogen protecting group, or two $R^{N2}$ are taken with the intervening atoms to form a heterocyclic ring, or $R^{N1}$ and $R^{N2}$ are taken with the intervening atoms to form a heterocyclic ring. In certain embodiments, $R^{N2}$ is nitrogen. In certain embodiments, $R^{N2}$ is optionally substituted $C_{1-6}$ alkyl. In certain embodiments, $R^{N2}$ is substituted $C_{1-6}$ alkyl. In certain embodiments, $R^{N2}$ is unsubstituted $C_{1-6}$ alkyl. In certain embodiments, $R^{N2}$ is methyl. In certain embodiments, $R^{N2}$ is ethyl. In certain embodiments, $R^{N2}$ is a nitrogen protecting group. In certain embodiments, two $R^{N1}$ are taken with the intervening atoms to form a heterocyclic ring. In certain embodiments, $R^{N1}$ and $R^{N2}$ are taken with the intervening atoms to form a heterocyclic ring.

In certain embodiments, $R^{N1}$ and $R^{N2}$ are the same. In certain embodiments, $R^{N1}$ and $R^{N2}$ are different. In certain embodiments, both $R^{N1}$ and $R^{N2}$ are hydrogen. In certain embodiments, $R^{N1}$ is hydrogen and $R^{N2}$ is not hydrogen. In certain embodiments, $R^{N1}$ is hydrogen and $R^{N2}$ is optionally substituted $C_{1-6}$ alkyl. In certain embodiments, $R^{N1}$ is hydrogen and $R^{N2}$ is substituted $C_{1-6}$ alkyl. In certain embodiments, $R^{N1}$ is hydrogen and $R^{N1}$ is unsubstituted $C_{1-6}$ alkyl. In certain embodiments, $R^{N1}$ is hydrogen and $R^{N2}$ is methyl, ethyl, or propyl. In certain embodiments, $R^{N1}$ and $R^{N2}$ are each independently optionally substituted $C_{1-6}$ alkyl. In certain embodiments, $R^{N1}$ and $R^{N2}$ are each independently substituted $C_{1-6}$ alkyl. In certain embodiments $R^{N1}$ and $R^{N2}$ are each independently unsubstituted $C_{1-6}$ alkyl. In certain embodiments, $R^{N1}$ and $R^{N2}$ are each independently is methyl, ethyl, or propyl. In certain embodiments, $R^{N1}$ and $R^{N2}$ are taken with the intervening atoms to form a heterocyclic ring. In certain embodiments, $R^{N1}$ and $R^{N2}$ are taken with the intervening atoms to form a six-membered heterocyclic ring. In certain embodiments, $R^{N1}$ and $R^{N2}$ are taken with the intervening atoms to form a five-membered heterocyclic ring. In certain embodiments, $R^{N1}$ and $R^{N2}$ are taken with the intervening atoms to form a bicyclic ring. In certain embodiments, $R^{N1}$ and $R^{N2}$ are each independently a nitrogen protecting group.

In certain embodiments, $X_1$ and $X_2$ are the same and $R^{N1}$ and $R^{N2}$ are the same. In certain embodiments, $X_1$ and $X_2$ are Cl and $R^{N1}$ and $R^{N2}$ are hydrogen. In certain embodiments, $X_1$ and $X_2$ are Cl and $R^{N1}$ and $R^{N2}$ are optionally substituted alkyl. In certain embodiments, $X_1$ and $X_2$ are Cl and $R^{N1}$ and $R^{N2}$ are substituted alkyl. In certain embodiments, $X_1$ and $X_2$ are Cl and $R^{N1}$ and $R^{N2}$ are unsubstituted alkyl. In certain embodiments, $X_1$ and $X_2$ are Cl and $R^{N1}$ and $R^{N2}$ are methyl, ethyl or propyl. In certain embodiments, $X_1$ and $X_2$ are Cl and $R^{N1}$ and $R^{N2}$ are taken with the intervening atoms to form a heterocyclic ring. In certain embodiments, $X_1$ and $X_2$ are Cl and $R^{N1}$ and $R^{N2}$ are taken with the intervening atoms to form a five-membered heterocyclic ring. In certain embodiments, $X_1$ and $X_2$ are Cl and $R^{N1}$ and $R^{N2}$ are taken with the intervening atoms to form a six-membered heterocyclic ring. In certain embodiments, $X_1$ and $X_2$ are Cl and $R^{N1}$ and $R^{N2}$ are taken with the intervening atoms to form a bicyclic ring.

As generally defined herein, n is 1, 2, 3, 4, 5, or 6. In certain embodiments, n is 1. In certain embodiments, n is 2. In certain embodiments, n is 3. In certain embodiments, n is 4. In certain embodiments, n is 5. In certain embodiments, n is 6.

In certain embodiments, the platinum complexes of Formula (I) are prodrugs of the platinum-based therapeutic agents. The Pt—O bond can be cleaved by a reducing agent in vivo to release the active platinum-based therapeutic agent. In certain embodiments, the platinum complex of Formula (I) is used as a crosslinker to prepare polymers for the controlled release of platinum-based agents. In certain embodiments, the platinum complex of Formula (I) is used as a crosslinker to prepare Pt-BASP.

In certain embodiments, the platinum complex of Formula (I) is of Formula (II):

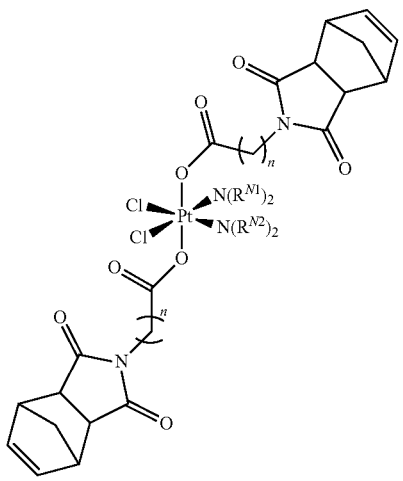

(II)

or a salt thereof.

In certain embodiments, the platinum complex of Formula (I) is of Formula (II-a):

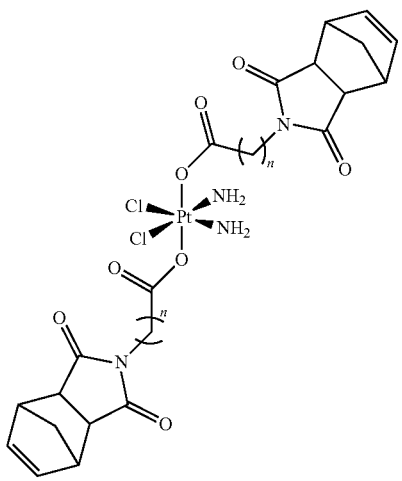

(II-a)

or a salt thereof.

In certain embodiments, the platinum complex of Formula (I) is of the formula:

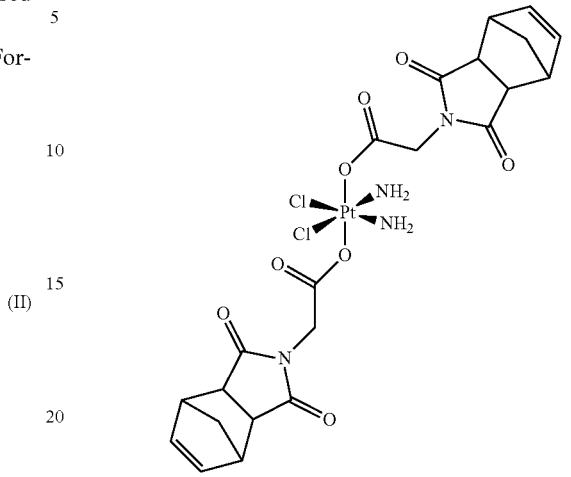

or a salt thereof.

The platinum complex of Formula (I) can be prepared using the general methodology shown in Scheme 1. Details of the synthetic procedures are described in the Examples below.

Scheme 1

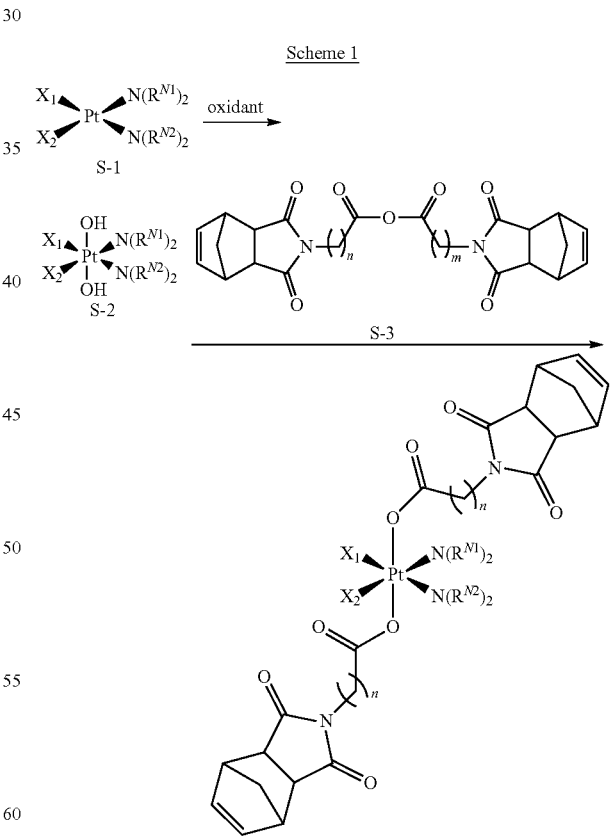

In one embodiments, the invention provides methods of preparing a platinum complex of Formula (I), the method comprising steps of:
(a) oxidizing a compound of Formula (s-1) with an oxidant $$\begin{array}{c} X_1 \diagdown_{Pt} \diagup N(R^{N1})_2 \\ X_2 \diagup \diagdown N(R^{N2})_2 \end{array} \quad (s\text{-}1)$$

to yield a compound of Formula (s-2):

$$\begin{array}{c} OH \\ | \\ X_1 \diagdown_{Pt} \diagup N(R^{N1})_2 \\ X_2 \diagup | \diagdown N(R^{N2})_2; \\ OH \end{array} \quad (s\text{-}2)$$

wherein:
 $X_1$ is F, Cl, Br, or I;
 $X_2$ is F, Cl, Br, or I;
 each instance of $R^{N1}$ and $R^{N2}$ is independently hydrogen, optionally substituted $C_{1-6}$ alkyl, or a nitrogen protecting group; or two $R^{N1}$ are taken with the intervening atoms to form a heterocyclic ring; or two $R^{N2}$ are taken with the intervening atoms to form a heterocyclic ring; or $R^{N1}$ and $R^{N2}$ are taken with the intervening atoms to form a heterocyclic ring; and
  n is 1, 2, 3, 4, 5, or 6; and
  (b) coupling the compound of Formula (s-2) with a compound of Formula (s-3):

(s-3)

to yield a platinum complex of Formula (I).

In certain embodiments, the oxidant used in step (a) can oxidize Pt (II) to Pt (IV) with two hydroxyl groups under suitable oxidization condition (Hall et al., *J. Biol. Inorg. Chem.* 2003, 8, 726). In certain embodiments, the oxidant is $H_2O_2$.

In certain embodiments, an activator is present in the coupling reaction in step (b). The activator converts the compound of Formula (s-3) to an activated ester for the coupling reaction. Examples of useful activators are dicyclohexylcarbodiimide (DCC), 1-ethyl-3-(3-dimethylaminopropyl)carbodiimide hydrochloride (WSC/HCl), diphenylphosphorylazide (DPPA), carbonyldiimidazole (CDI), diethylcyanophosphonate (DEPC), benzotriazole-1-yloxytrispyrrolidinophosphonium (DIPCI), benzotriazole-1-yloxy-trispyrrolidinophosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazole-1-yl)-1,1,3,3-tetramethyluronium hexafluorophosphate (HBTU), O-(7-azabenzotriazole-1-yl)-1,1,3,3-tetramethyluronium hexafluorophosphonate (HATU), O-benzotriazole-1-yl-1,1,3,3-tetramethyluronium tetrafluoroborate (TBTU), 3,4-dihydro-3-hydrodi-4-oxa-1,2,3-benzotriazine (Dhbt). In certain embodiments, the activator is DCC.

The activator is used in an amount of about 1 to 20 equivalents of the compound of Formula (s-2). In certain embodiments, the activator is used in an amount of about 1 to 10 equivalents. In certain embodiments, the activator is used in an amount of about 1 to 5 equivalents.

Examples of useful solvents in the coupling reaction are DMSO, DMF, methylene chloride. The coupling reaction can be conducted at 0 to 50° C. In certain embodiments, the coupling reaction is conducted at room temperature for about 10 min to about 30 hours. In certain embodiments, the coupling reaction is conducted for about 15 minutes to about 24 hours.

Macromonomers

In one aspect, the present invention provides a macromonomer of Formula (III).

(III)

or a salt thereof,
wherein:
 a is an integer from 1 to 10, inclusive;
 b is an integer from 1 to 5 inclusive;
 c is an integer from 30 to 100 inclusive;
 e is 0, 1, 2, 3, or 4;
 L is —O—, —S—, —$NR^{La}$—, —$NR^{La}C(=O)$—, —$C(=O)NR^{La}$—, —$SC(=O)$—, —$C(=O)S$—, —$OC(=O)$—, —$C(=O)O$—, —$OC(=O)O$—, —$OC(=O)NR^{La}$—, —$NR^{La}C(=O)O$—, trans-$CR^{Lb}=CR^{Lb}$—, cis-$CR^{Lb}=CR^{Lb}$—, —C≡C—, —$OC(R^{Lb})_2$—, —$C(R^{Lb})_2O$—, —$NR^{La}C(R^{Lb})_2$—, —$C(R^{Lb})_2NR^{La}$—, —$S(=O)_2O$—, —$OS(=O)_2$—, —$S(=O)_2NR^{La}$—, —$NR^{La}S(=O)_2$—, or an optionally substituted $C_{1-10}$ hydrocarbon chain, optionally wherein one or more carbon units of the hydrocarbon chain is replaced with —O—, —S—, —$NR^{La}$—, —$NR^{La}C(=O)$—, —$C(=O)NR^{La}$—, —$OC(=O)$—, —$C(=O)O$—, —$OC(=O)O$—, —$OC(=O)NR^{La}$—, —$NR^{La}C(=O)O$—, trans-$CR^{Lb}=CR^{Lb}$—, cis-$CR^{Lb}=CR^{Lb}$—, —C≡C—, —$OC(R^{Lb})_2$—, —$C(R^{Lb})_2O$—, —$NR^{La}C(R^{Lb})_2$—, —$C(R^{Lb})_2NR^{La}$—, —$S(=O)_2O$—, —$OS(=O)_2$—, —$S(=O)_2NR^{La}$—, or —$NR^{La}S(=O)_2$—, wherein each instance of $R^{La}$ is independently hydrogen, optionally substituted $C_{1-10}$ alkyl, or a nitrogen protecting group, and wherein each occurrence of $R^{Lb}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{Lb}$ groups are joined to form an optionally substituted carbocyclic or optionally substituted heterocyclic ring, or $R^{La}$ and $R^{Lb}$ are joined to form an optionally substituted heterocyclic ring; and M is hydrogen or a therapeutic, diagnostic, or prophylactic agent.

As generally defined herein, a is an integer from 1 to 10, inclusive. In certain embodiments, a is 1. In certain embodiments, a is 2. In certain embodiments, a is 3. In certain embodiments, a is 4. In certain embodiments, a is 5. In certain embodiments, a is 6. In certain embodiments, a is 7. In certain embodiments, a is 8. In certain embodiments, a is 9. In certain embodiments, a is 10.

As generally defined herein, b is an integer from 1 to 5, inclusive. In certain embodiments, b is 1. In certain embodiments, b is 2. In certain embodiments, b is 3. In certain embodiments, b is 4. In certain embodiments, b is 5.

As generally defined herein, c is an integer from 30 to 100, inclusive. In certain embodiments, c is an integer from 40 to 90, inclusive. In certain embodiments, c is an integer from 50 to 80, inclusive. In certain embodiments, c is an integer from 60 to 70, inclusive. In certain embodiments, c is from 65. In certain embodiments, c is from 66. In certain embodiments, c is from 67. In certain embodiments, c is from 68. In certain embodiments, c is from 69. In certain embodiments, c is from 70.

As generally defined herein, e is 0, 1, 2, 3, or 4. In certain embodiments, e is 0. In certain embodiments, e is 1. In certain embodiments, e is 2. In certain embodiments, e is 3. In certain embodiments, e is 4.

As generally defined herein, linker L is —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=C$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, —NR$^{La}$S(=O)$_2$—, or an optionally substituted C$_{1-10}$ hydrocarbon chain, optionally wherein one or more carbon units of the hydrocarbon chain is replaced with —O—, —S—, —NR$^{La}$—, —NR$^{La}$C(=O)—, —C(=O)NR$^{La}$—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—, wherein each instance of R$^{La}$ is independently hydrogen, optionally substituted C$_{1-10}$ alkyl, or a nitrogen protecting group, and wherein each occurrence of R$^{Lb}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{Lb}$ groups are joined to form an optionally substituted carbocyclic or optionally substituted heterocyclic ring, or R$^{La}$ and R$^{Lb}$ are joined to form an optionally substituted heterocyclic ring. In certain embodiments, L is an optionally substituted C$_{1-10}$ hydrocarbon chain, optionally wherein one or more carbon units of the hydrocarbon chain is replaced with —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—. In certain embodiments, L is of the Formula (L-1):

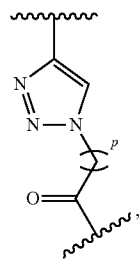

(L-1)

wherein p is an integer from 1 to 10 inclusive. In certain embodiments, L is of the Formula (L-2):

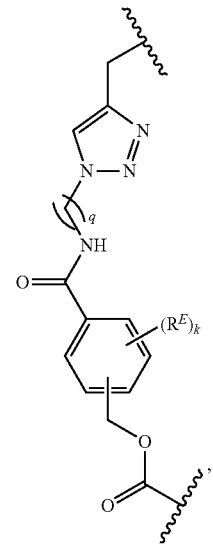

(L-2)

wherein q is an integer of 1 to 10, inclusive; each instance of R$^E$ is halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$; wherein each R$^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl; and each R$^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^B$ groups are taken together with their intervening atoms to form an optionally substituted heterocyclic ring; and k is 0, 1, 2, 3, 4, or 5. In certain embodiments, L is of the formula:

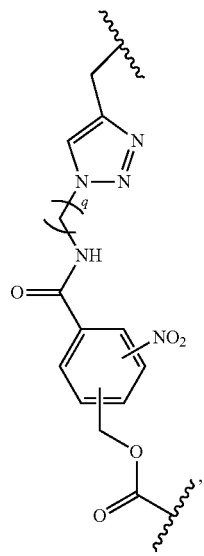
wherein q is an integer of 1 to 10, inclusive. In certain embodiments, L is of the formula:
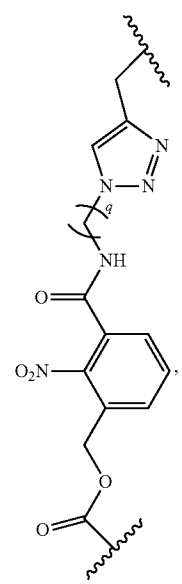
wherein q is 3. In certain embodiments, L is of the Formula (L-3):
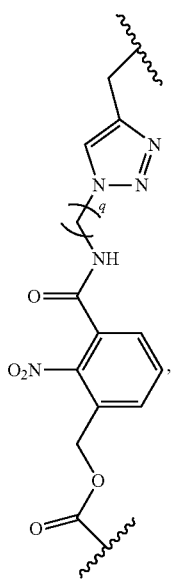
wherein q is an integer of 1 to 10, inclusive. In certain embodiments, L is of the formula:
(L-3)
wherein g is an integer from 1 to 10, inclusive. In certain embodiments, L is of the Formula (L-3):

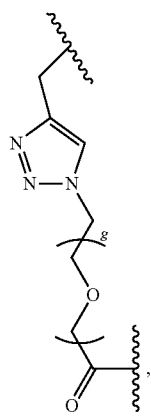

wherein g is an integer from 1 to 5, inclusive. In certain embodiments, L is of the Formula (L-3):

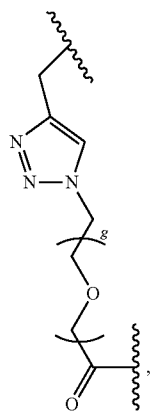

wherein g is 3. In certain embodiments, L is of the Formula (L-4):

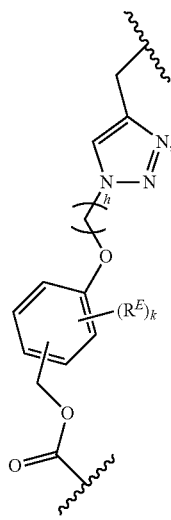

wherein h is an integer of 1 to 10, inclusive; each instance of $R^E$ is halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$; wherein each $R^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl; and each $R^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring; and k is 0, 1, 2, 3, 4, or 5. In certain embodiments, L is of the formula:

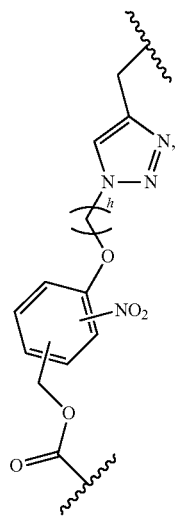

wherein h is an integer of 1 to 10, inclusive. In certain embodiments, L is of the formula:

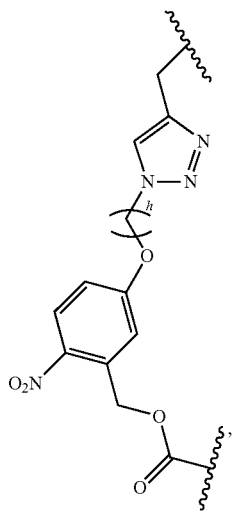

wherein h is an integer of 1 to 10, inclusive. In certain embodiments, L is of the formula:

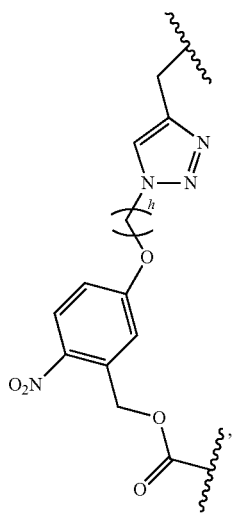

wherein h is 3. In certain embodiments, L is of the Formula:

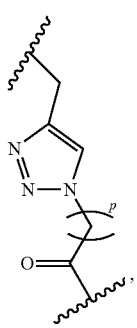
(L-5)

wherein p is an integer from 1 to 10 inclusive. In certain embodiments, L is of the Formula (L-5):

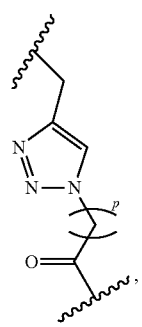
(L-5)

wherein p is an integer from 1 to 5 inclusive. In certain embodiments, L is of the Formula (L-5):

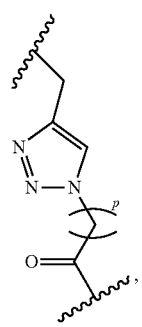
(L-5)

wherein p is 5.

In certain embodiments, the macromonomer of Formula (III) is of the Formula (III-a):

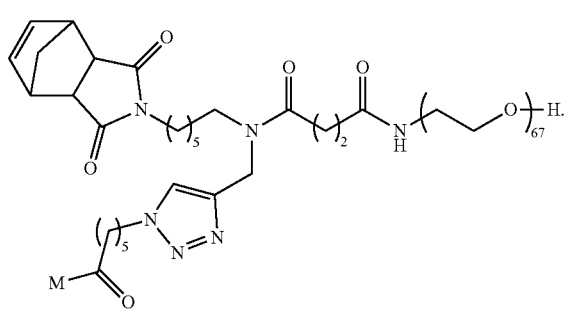
(III-a)

In certain embodiments, the macromonomer of Formula (III) is of the Formula (III-c):

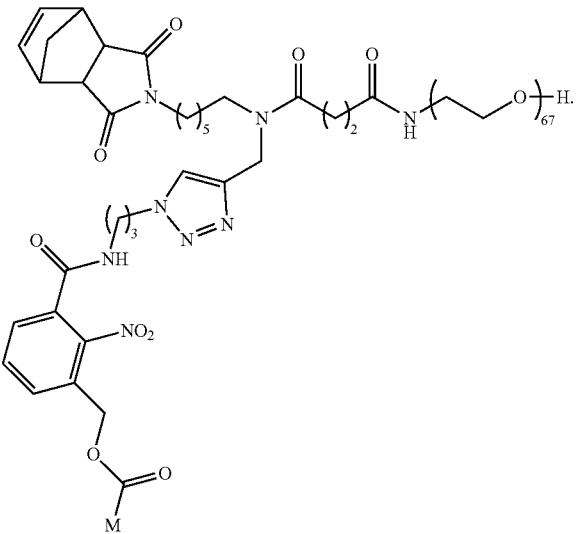

(III-b)

In certain embodiments, the macromonomer of Formula (III) is of the Formula (III-c):

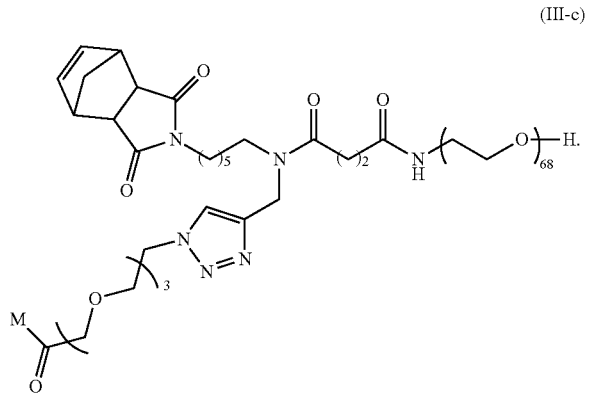

(III-c)

In certain embodiments, the macromonomer of Formula (III) is of the Formula (III-d):

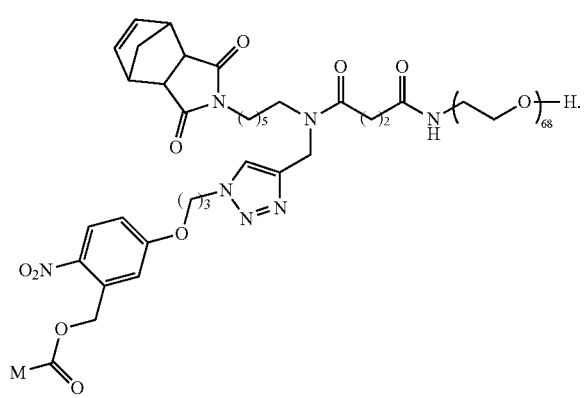

(III-d)

As generally defined herein, M is hydrogen or a therapeutic, diagnostic, or prophylactic agent. In certain embodiments, M is hydrogen. In certain embodiments, M is a therapeutic, diagnostic, or prophylactic agent. In certain embodiments, M is a therapeutic agent. Examples of therapeutic moieties include, but are not limited to, antimicrobial agents, analgesics, antinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic moieties include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins. In certain embodiments, M is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG 1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g. 1-methyl-4-phenylpyridinium ion), cell cycle inhibitors (e.g., staurosporine), actinomycin (e.g. actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU 11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca). BEZ235 (Novartis), BGT226 (Norvartis), XL765 (Sanofi Aventis), PF-4691502 (Pfizer). GDC0980 (Genetech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, lcurosine, chlorambucil, trabcctedin, procarbazine, discodermolide, carminomycin, aminopterin, and hexamethyl melamine. In certain embodiments. M is camptothecin or doxorubicin.

In certain embodiments, M is a diagnostic agent. Exemplary diagnostic agents include, but are not limited to, fluorescent molecules; gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials. In certain embodiments, the diagnostic agent is used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A which are reviewed in Aime, et al. (*Chemical Society Reviews* (1998), 27:19-29), the entire teachings of which are incorporated herein by reference.

In certain embodiments, M is a prophylactic agent. Prophylactic agents that can be included in the conjugates of the invention include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum. Freund's adjuvant.

M can be conjugated to the macromonomer using any suitable conjugation technique. For instance, EDC-NHS chemistry (1-ethyl-3-(3-dimethylaminopropyl) carbodiimide hydrochloride and N-hydroxysuccinimide), or a reaction involving a maleimide or a carboxylic acid, which can be conjugated to one end of a thiol, an amine, or a similarly functionalized polyether. The conjugation can be performed in an organic solvent, such as, but not limited to, methylene chloride, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting the agent that includes a hydroxyl, thiol, or amino group with a polymer comprising a carboxylic acid functional group. Such a reaction may occur as a single-step reaction, i.e., the conjugation is performed with or without using intermediates such as N-hydroxysuccinimide or a maleimide. The conjugation reaction between the amine-containing, thiol-containing, or hydroxyl-containing moiety and the carboxylic acid-terminated polymer may be achieved in one embodiment, by adding the amine-containing, thoil-containing, or hydroxyl-containing moiety, solubilized in an organic solvent such as, but not limited to, dichloromethane, acetonitrile, chloroform, tetrahydrofuran, acetone, formamide, dimethylformamide, pyridines, dioxane, or dimethysulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously in some cases. Unconjugated macromonomers may be washed away after such reactions, and the polymer may be precipitated in solvents such as, for instance, ethyl ether, hexane, methanol, or ethanol.

In some cases, the Pt-BASPs are of the form of nanoparticles, i.e., the particle have a characteristic dimension of less than about 1 micrometer, where the characteristic dimension of a particle is the diameter of a perfect sphere having the same volume as the particle. In certain embodiments, the Pt-BASP particle has a characteristic dimension of less than about 300 nm. In certain embodiments, the Pt-BASP particle has a characteristic dimension of less than about 200 nm. In certain embodiments, the Pt-BASP particle has a characteristic dimension of less than about 150 nm. In certain embodiments, the Pt-BASP particle has a characteristic dimension of less than about 100 nm. In certain embodiments, the Pt-BASP particle has a characteristic dimension of less than about 50 nm. In certain embodiments, the Pt-BASP particle has a characteristic dimension of less than about 30 nm. In certain embodiments, the Pt-BASP particle has a characteristic dimension of less than about 20 nm. In certain embodiments, the Pt-BASP particle has a characteristic dimension of less than about 10 nm. In certain embodiments, the Pt-BASP particle has a characteristic dimension between 6 and 250 nm, inclusive. In certain embodiments, the Pt-BASP particle has a characteristic dimension between 8 and 200 nm, inclusive. In certain embodiments, the Pt-BASP particle has a characteristic dimension between 12 and 200 nm, inclusive. In certain embodiments, the Pt-BASP particle has a characteristic dimension between 50 and 200 nm, inclusive.

In certain embodiments, the macromonomer of Formula (III) is of the formula:

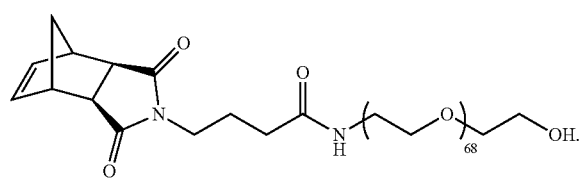

In certain embodiments, the macromonomer of Formula (III) is of the formula:

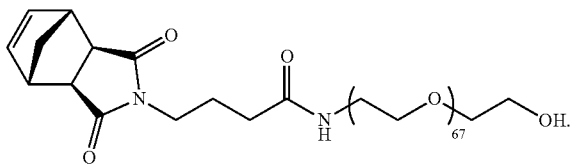

In certain embodiments, the macromonomer of Formula (III) is a camptothecin macromonomer of the formula:

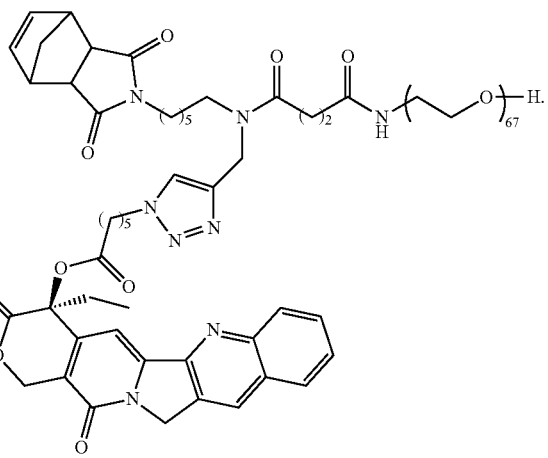

In certain embodiments, the macromonomer of Formula (III) is a camptothecin macromonomer of the formula:

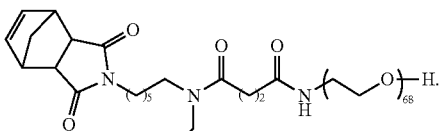
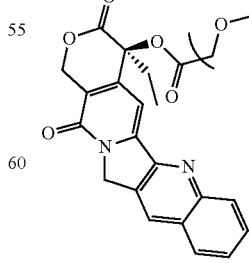

In certain embodiments, the macromonomer of Formula (III) is doxorubicin macromonomer of the formula:

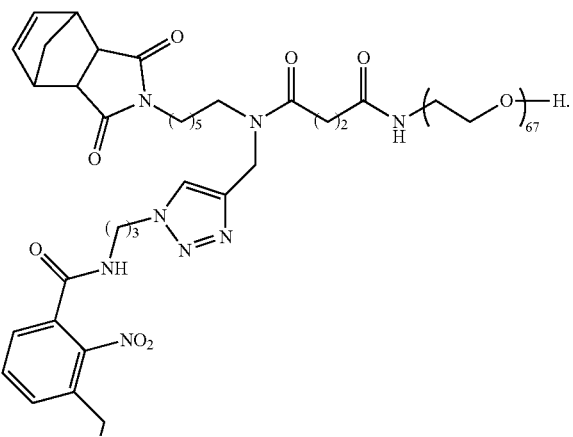
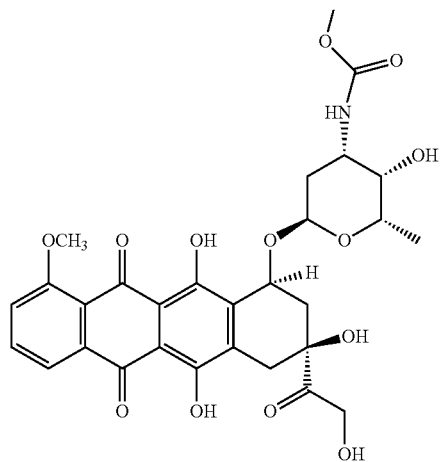
In certain embodiments, the macromonomer of Formula (III) is doxorubicin macromonomer of the formula:
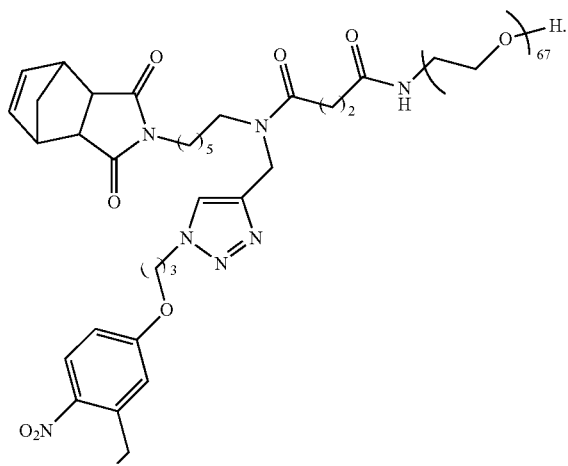

-continued

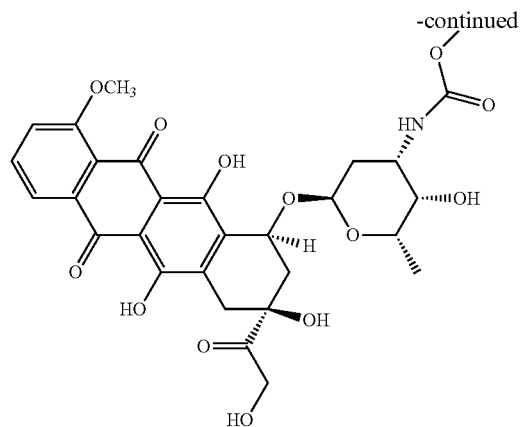

The macromonomers of Formula (III) can be prepared using the general methods shown in J. Johnson et al., *Macromolecules,* 2010, 43 (24), 10326-10335.

Platinum-Based Brush-Arm Star Polymers (Pt-BASPs)

Figure 2:
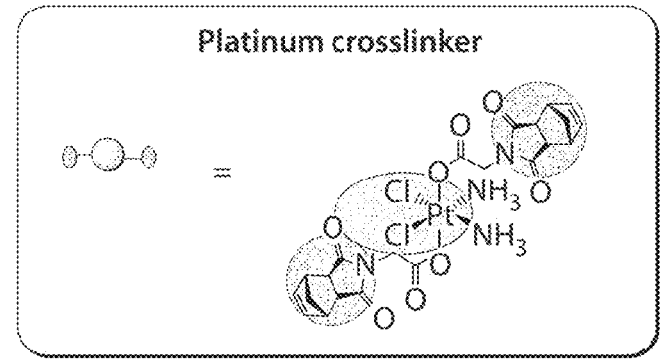
Figure 1B:
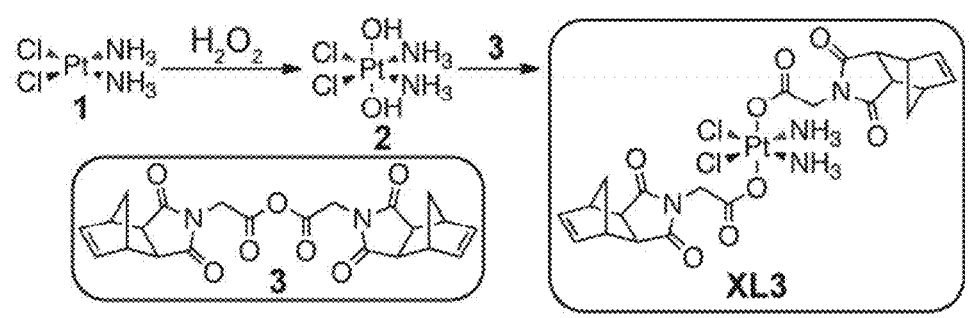
FIG. 1B shows an exemplary synthesis of the cisplatin prodrug crosslinker XL3.
Figure 2:
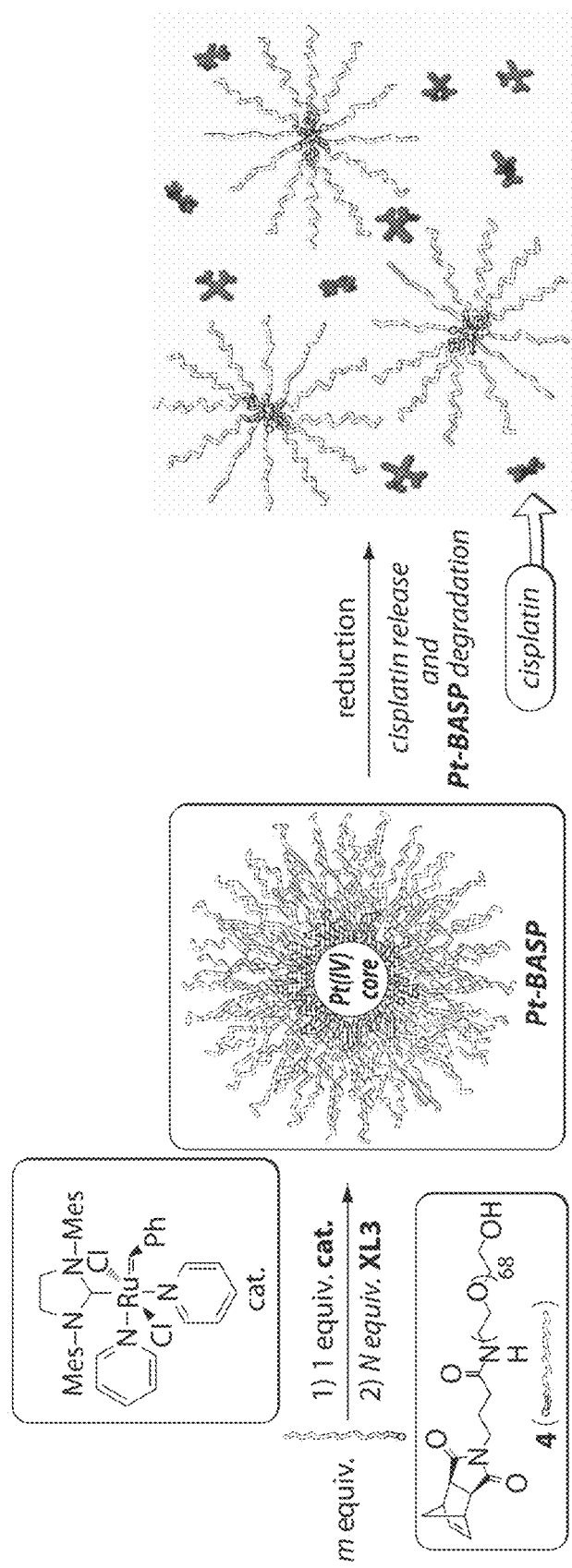
Figure 3A:
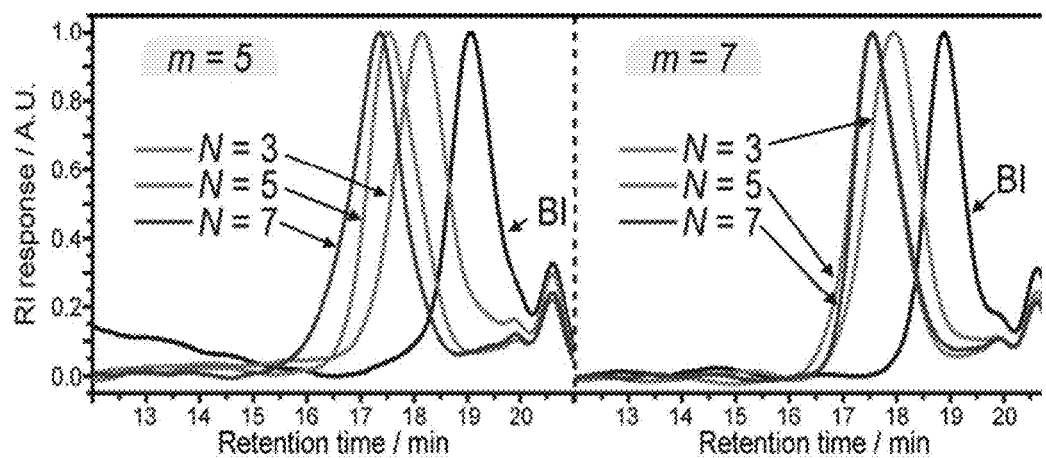
FIG. 3A shows gel permeation chromatography (GPC) evaluation of the molecular weight of exemplary cisplatin-based Pt-BASPs. The weight-average molecular weights (MWs) and dispersity indices (Đ) of each Pt-BASP (specific samples referred to by their m and N values, e.g., m5N3) were obtained by gel permeation chromatography (GPC) coupled with a multi-angle laser light scattering (MALLS) detector using DMF with 0.2 M LiBr eluent. The molecular weight generally increases with N and decreases with m; these trends agree with our previously proposed growth mechanism. The GPC traces were monomodal and the Đ values were low (<1.3) for most m and N combinations. The average numbers of BIs per Pt-BASP (<# BI>) and platinum atoms per Pt-BASP (<# Pt>), and the corresponding weight percentage of cisplatin (% 1), are listed in Table 1 as shown in FIG. 4. From this series of parallel reactions a range of cisplatin loadings from 1% to 9% was achieved. Increasing N or truncating compound 4 could increase these values.
Figure 3B:
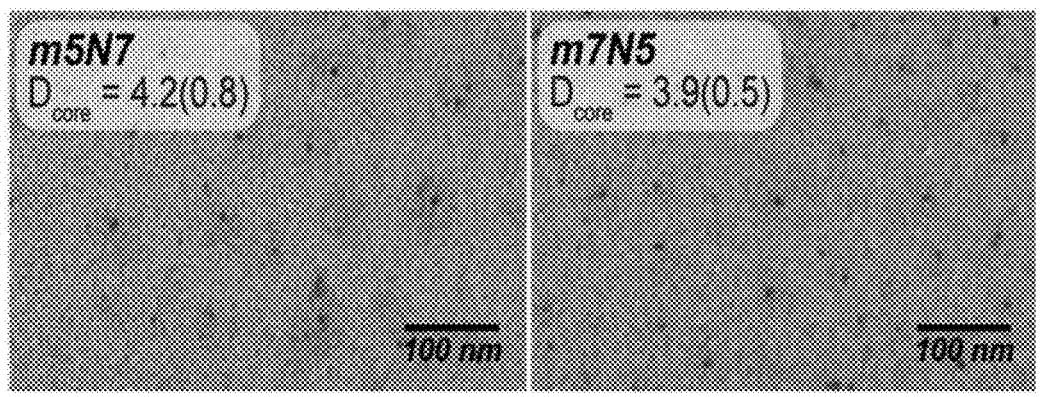
FIG. 3B shows images of exemplary cisplatin-based Pt-BASPs particles from transmission electron microscopy (TEM). TEM of unstained Pt-BASPs revealed particles that ranged from 2.0 nm to 5.0 nm in diameter. The observed particle sizes correspond to the core size $D_{core}$ (see FIG. 4). $D_{core}$ generally increased with percentage of cisplatin 1. Larger particles were observed when samples were stained with $RuO_4$ prior to imaging. For example, the m5N5 sample, which had an unstained size of 3.3±0.5 nm, possessed a stained size of 9.3±0.9. This can be attributed to $RuO_4$ staining at least a portion of the PEG corona.
Figure 3C:
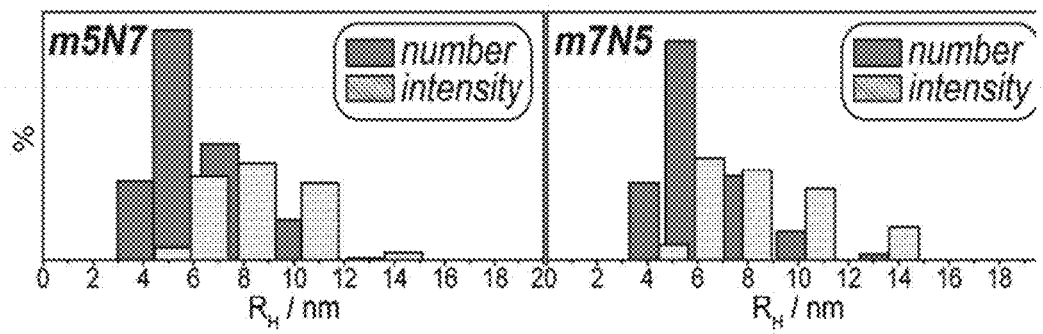
FIG. 3C shows histograms of hydrodynamic radii ($R_H$) of exemplary cisplatin-based Pt-BASPs.

The present invention provides platinum-based brush-arm star polymers (Pt-BASP) using the "brush-first" ring-opening metathesis polymerization (ROMP). The brush-first method involves sequential copolymerization of two functional monomers, a polymeric macromonomer (MM) followed by a multifunctional crosslinker, to generate a unimolecular micelle-like nanostructure with a core comprised of the crosslinker and a corona comprised of the MM. For example, FIG. 2 shows the exemplary synthesis of Pt-BASPs via a route that combines the "graft-through" and "arm-first" methodologies. Homopolymerization of macromonomer 4 catalyzed by third-generation Grubb's catalyst C1 generated living polymerization chains, which then served as "brush initiators" to initiate reaction with the cross-linker XL3, forming stars Pt-BASP with covalently bound Pt(IV) complex cores. Under the reducing environment in cells, the cores constructed by Pt(IV) complexes will be reduced, which leads to the release of Pt complexes and degradation of the star polymers.

A Pt-BASP described herein includes a cisplatin moiety attached to the rest of the Pt-BASP through ester bonds. Cisplatin is a clinically approved chemotherapeutic agent that includes a platinum(IV) (Pt(IV)) core. Pt(IV) diester derivatives have been widely applied as prodrugs for cisplatin (Hall, M. D.; Hambley, T. W. *Coord. Chem. Rev.* 2002, 232, 49; Nishiyama et al. *Cancer Res.* 2003, 63, 8977; Dhar, S.; Gu, F. X.; Langer, R.; Farokhzad, O. C.; Lippard. S. *J. Proc. Natl. Acad. Sci. U.S.A* 2008, 105, 17356; Dhar, S.; Daniel, W. L.; Giljohann, D. A.; Mirkin, C. A.; Lippard. S. *J. J. Am. Chem. Soc.* 2009, 131, 14652; Plummer et al., *Br. J. Cancer* 2011, 104, 593). Pt(IV) diesters release cytotoxic platinum(II) (Pt(II)) species upon glutathione-induced intracellular reduction.

In addition to cisplatin, a Pt-BASP described herein may include one or more additional agents that are not cisplatin to form multi-agent-loaded (e.g., multi-drug-loaded) Pt-BASPs. The described Pt-BASPs are advantageous over known nanoparticle (NP)-based delivery systems. NP-based combination cancer therapy has the potential to overcome the toxicity and poorly controlled dosing of traditional systemic combination therapies (Hu. C. M. J.; Zhang, L. F. *Biochem. Pharmacol.* 2012, 83, 1104; Yan, Y.; Bjornmalm, M.; Caruso, F. *ACS Nano* 2013, 7, 9512; Ma, L.; Kohli, M.; Smith, A. *ACS Nano* 2013, 7, 9518). Though NP-based therapeutics for cancer therapy have been the subject of numerous investigations over the past several decades (Duncan, R. *Nat. Rev. Drug Discovery* 2003, 2, 347; Peer et al. *Nat. Nanotechnol.* 2007, 2, 751; Wolinsky, J. B.; Grinstaff, M. W. *Adv. Drug Delivery Rev.* 2008, 60, 1037; Davis, M. E.; Chen, Z.; Shin, D. M. *Nat. Rev. Drug Discovery* 2008, 7, 771; Kwon, G. S.; Kataoka. K. *Adv. Drug Delivery Rev.* 2012, 64, 237), ratiometric, synchronized release of multiple drugs from single NP scaffolds remains a challenge (Sengupta et al. *Nature* 2005, 436, 568; Lammers et al. *Biomaterials* 2009, 30, 3466; Kolishetti, N.; Dhar, S.; Valencia, P. M.; Lin, L. Q.; Karnik, R.; Lippard, S. J.; Langer, R.; Farokhzad, O. C. *Proc. Natl. Acad. Sci. U.S.A* 2010, 107, 17939; Aryal, S.; Hu, C. M. J.; Zhang, L. F. *Mol. Pharm.* 2011, 8, 1401). Many reported nanoparticle architectures for delivery, e.g., liposomes, micelles, and dendrimers, are not readily amenable to controlled incorporation and release of multiple drugs.

In contrast, the Pt-BASPs described herein are able to deliver multiple agents (e.g., cisplatin and one or more other agents) ratiometrically. The agents included in a Pt-BASP may show different therapeutic, diagnostic, and/or prophylactic effects on a subject, tissue, or cell. For example, a Pt-BASP may include two or more therapeutic agents (including cisplatin), and the therapeutic agents may show different anti-proliferative activities (e.g., anti-cancer activities) at each therapeutic agent's maximum tolerated dose (MTD). A key benefit of single nanoparticle combination therapy is the ability to deliver multiple drugs at a precise ratio to a subject, tissue, or cell, while minimizing undesired effects (e.g., toxicity) associated with multiple drug combinations. To achieve the maximum therapeutic index in a multi-drug combination therapy, simultaneous dosing of each drug at or near each drug's MTD would be ideal. A Pt-BASP described herein may include multiple drugs at or near each drug's MTD before the Pt-BASP is delivered to a subject, tissue, or cell, release the multiple drugs at or near each drug's MTD into the subject, tissue, or cell after delivery, and therefore achieve the maximum therapeutic index. In certain embodiments, a Pt-BASP described herein includes camptothecin (CPT) and cisplatin. In certain embodiments, a Pt-BASP described herein includes doxorubicin (DOX) and cisplatin. In certain embodiments, a Pt-BASP described herein includes CPT, DOX, and cisplatin. CPT, DOX, and cisplatin have shown non-overlapping toxicity profiles (Devita et al. *Ann. Intern. Med.* 1970, 73, 881; Al-Lazikani, B.; Banerji, U.; Workman, P. *Nat. Biotechnol.* 2012, 30, 679). A serious dose-limiting side effect from doxorubicin may arise due to cardiotoxicity (Singal, P. K.; Iliskovic, N. *N. Engl. J. Med.* 1998, 339, 900), while those from cisplatin and camptothecin may result from neurotoxicity (Mollman, *N. Engl. J. Med.* 1990, 322, 126) and myelosuppression or hemorrhagic cystitis (Pizzolato, J. F.; Saltz, L. B. *Lancet* 2003, 361, 2235), respectively. In certain embodiments, a Pt-BASP described herein includes CPT, DOX, and cisplatin, wherein the molar ratio of CPT:DOX:cisplatin in the Pt-BASP is substantially equal to the ratio of the MTD of CPT:the MTD of DOX:the MTD of cisplatin against a cell (e.g., a cancer cell). In certain embodiments, the molar ratio of CPT:DOX:cisplatin in a Pt-BASP that includes CPT, DOX, and cisplatin is substantially equal to the ratio of (the MTD of CPT)×2:(the MTD of DOX)×2:the MTD of cisplatin against a cell (e.g., a cancer cell) (Caiolfa et al. *J. Controlled Release* 2000, 65, 105; MacKay, J. A.; Chen, M. N.; McDaniel, J. R.; Liu, W. G.; Simnick, A. J.; Chilkoti. A. *Nat. Mater* 2009, 8, 993; Chang, C. L.; Hsu, Y. T.; Wu, C. C.; Lai, Y. Z.; Wang, C. N.; Yang, Y. C.; Wu, T. C.; Hung. C. F. *Cancer Res.* 2013, 73, 119). In certain embodiments, the molar ratio of CPT:DOX:cisplatin in a Pt-BASP that includes CPT, DOX, and cisplatin is about 2.07:0.83:3.00. It has been shown that Pt-BASPs (e.g., polymer P3) that include CPT, DOX, and cisplatin at a molar ratio of about 2.07:0.83:3.00 outperformed Pt-BASPs that include only one or two of CPT, DOX, and cisplatin, in in vitro cell viability studies using ovarian cancer (OVCAR3) cells.

The Pt-BASPs described herein are also able to deliver multiple agents orthogonally. Different chemical and/or physical conditions may be employed to individually release the multiple agents upon delivery. The convergent synthesis of Pt-BASPs allow the attachment of different agents to the Pt-BASPs through different linkers (e.g., linkers cleavable by reduction, such as Pt—O bonds; hydrolysable linkers, such as ester bonds; and photo-cleavable linkers, such as the moiety

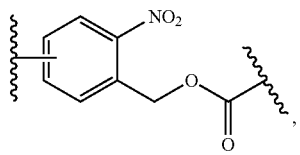

wherein the moiety may be further substituted). For example, cisplatin may be released from a Pt-BASP by a reduction reaction of the Pt—O bonds of cisplatin; and other agents included in the Pt-BASP may be released from the Pt-BASP under chemical and/or physical conditions that are different from the reduction reaction. In certain embodiments, an agent, other than cisplatin, included in a Pt-BASP is released from the Pt-BASP by hydrolysis (e.g., hydrolysis under acidic conditions). In certain embodiments, an agent, other than cisplatin, included in a Pt-BASP is released from the Pt-BASP by irradiation with ultraviolet light (UV). For example, orthogonal release of of CPT, DOX, and cisplatin from polymer P3 may be achieved by hydrolyzation (which releases CPT), irradiation with UV (which releases DOX), and reduction (which releases cisplatin), wherein the hydrolyzation, irradiation, and reduction may be performed in any order and at the same time or different times.

The Pt-BASPs described herein can be directly constructed using carefully designed drug-conjugates as building blocks, and no self-assembly is required for preparing the Pt-BASPs. The methods for preparing the Pt-BASPs described herein involves ring-opening metathesis polymerization (ROMP) (Liu et al. *J. Am. Chem. Soc.* 2012, 134, 16337; Liu, J.; Gao, A. X.; Johnson, J. A. *J Vis Erp* 2013, e50874). In certain embodiments, the Pt-BASPs described herein are prepared by polymerization of norbornene-terminated macromonomers (MMs) followed by in situ crosslinking with bis-norbornene crosslinkers. The preparation methods described herein are versatile and have little limitations, e.g., in terms of the different agents that can be built into the Pt-BASPs. In certain embodiments, an agent that can be built into the Pt-BASPs includes addressable functional groups that are compatible with ROMP. In certain embodiments, the invention provides Pt-BASPs prepared by Method A including the steps of:

(a) reacting a macromonomer of Formula (III) (e.g., a macromonomer of Formula (III))

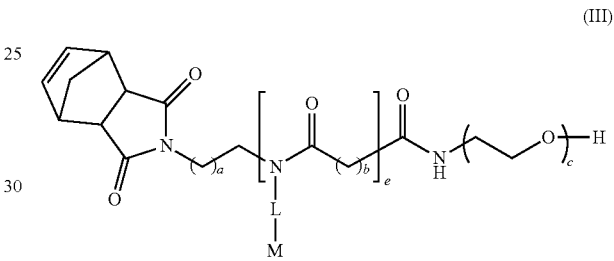

with a metathesis catalyst to form a polymerization mixture; and (b) mixing the polymerization mixture from step (a) with a solution of a platinum complex of Formula (I):

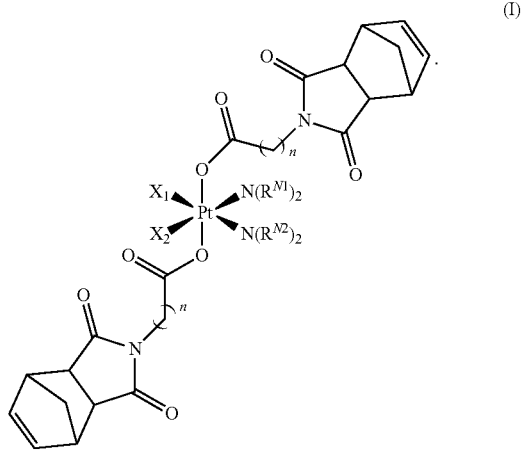

In certain embodiments, M in the macromonomer is not cisplatin. In Method A, step (a) may be performed in the presence of a non-agent-loaded MM, such as a macromonomer of Formula (IV):

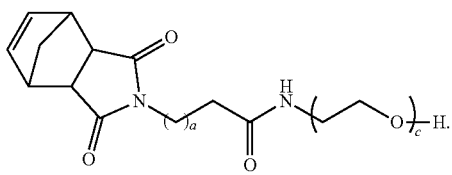

(IV)

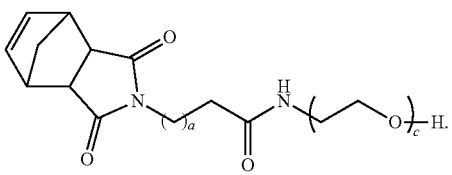

(IV)

In certain embodiments, the molar ratio of a non-agent-loaded MM to the combined agents (including cisplatin) is about 0.01:1, about 0.3:1, about 0.67:1, about 1:1, about 1.5:1, about 3:1, about 10:1, about 30:1, or about 100:1. In certain embodiments, the molar ratio of a non-agent-loaded macromonomer to the combined agents (including cisplatin) is about 0.67:1.

In certain embodiments, the provided Pt-BASPs are loaded with more than one therapeutic, diagnostic, or prophylactic agents other than cisplatin and can be prepared by Method B including the steps of:

(a) reacting a first macromonomer of Formula (III) with a second macromonomer of Formula (III)

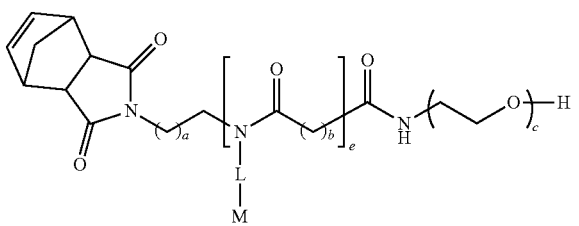

(III)

in the presence of a metathesis catalyst to form a polymerization mixture, wherein M in the first macromonomer is different from M in the second macromonomer; and (b) mixing the polymerization mixture from step (a) with a solution of a platinum complex of Formula (I):

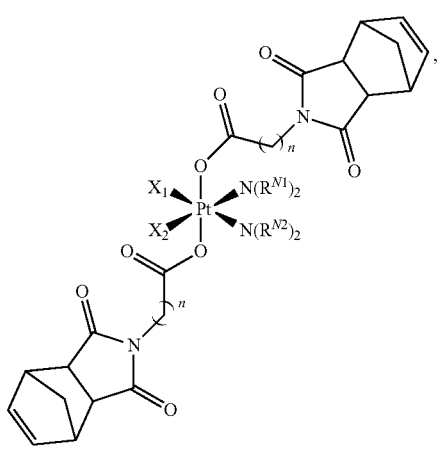

(I)

wherein a, b, c, e, M, L, $X_1$, $X_2$, $R^{N1}$, $R^{N1}$, and $R^{N2}$, are as defined herein.

In Method B, step (a) may be performed in the presence of a non-agent-loaded MM, such as a macromonomer of Formula (IV):

In certain embodiments, the non-agent-loaded MM is macromonomer PEG-MM. In certain embodiments of the Pt-BASPs loaded with more than one therapeutic, diagnostic, or prophylactic agents, Ms in the first and second macromonomers are different. In certain embodiments. Ms in the first and second macromonomers are not cisplatin. In certain embodiments of the Pt-BASPs loaded with more than one therapeutic, diagnostic, or prophylactic agents. Ms in the first and second macromonomers are different therapeutic agents. In certain embodiments of the Pt-BASPs loaded with more than one therapeutic, diagnostic, or prophylactic agents, M in the first macromonomer is camptothecin, and M in the second macromonomer is doxorubicin. In certain embodiments of the Pt-BASPs loaded with more than one therapeutic, diagnostic, or prophylactic agents, M in the first macromonomer is doxorubicin, and M in the second macromonomer is camptothecin.

The synthesis of Pt-BASPs involves ROMP of MM in step (a) and ROMP of the platinum complex in step (b). In certain embodiments, the ROMP catalyst is a tungsten (W), molybdenum (Mo), or ruthenium (Ru) catalyst. In certain embodiments, the ROMP catalyst is a ruthenuim catalyst. ROMP catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

In certain embodiments, the ROMP catalyst is a Grubbs catalyst. In certain embodiments, the Grubbs catalyst is selected from the group consisting of:

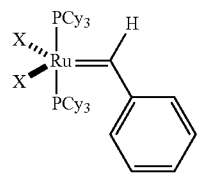

X = Cl; Br; I
Cy = cyclohexyl

Benzylidenebis-(tricyclohexylphosphine)-dichlororuthenium (X=Cl);

Benzylidenebis-(tricyclohexylphosphine)-dibromoruthenium (X=Br);

Benzylidenebis-(tricyclohexylphosphine)-diiodoruthenium (X=I);

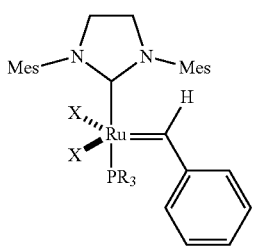

X = Cl; Br; I
R = cyclohexyl (Cy); phenyl (Ph); benzyl (Bn)

1,3-(Bis(mesityl)-2-imidazolidinylidene)dichloro-(phenyl-methylene) (tricyclohexyl-phosphine)ruthenium (X=Cl; R=cyclohexyl);

1,3-(Bis(mesityl)-2-imidazolidinylidene)dibromo-(phenyl-methylene) (tricyclohexyl-phosphine)ruthenium (X=Br, R=cyclohexyl);

1,3-(Bis(mesityl)-2-imidazolidinylidene)diiodo-(phenylmethylene) (tricyclohexyl-phosphine)ruthenium (X=I; R=cyclohexyl);

1,3-(Bis(mesityl)-2-imidazolidinylidene)dichloro-(phenyl-methylene) (triphenylphosphine)ruthenium (X=Cl; R=phenyl);

1,3-(Bis(mesityl)-2-imidazolidinylidene)dichloro-(phenyl-methylene) (tribenzylphosphine)ruthenium (X=Cl; R=benzyl):

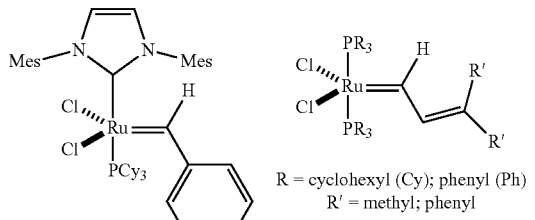

R = cyclohexyl (Cy); phenyl (Ph)
R' = methyl; phenyl

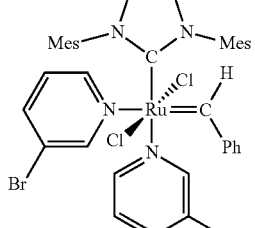

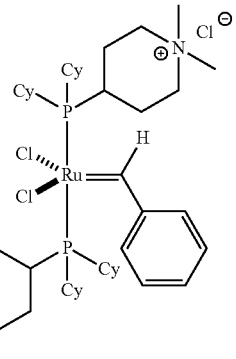

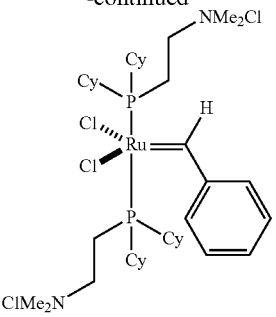

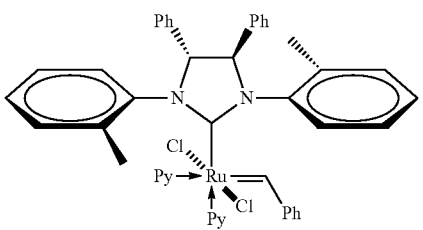

Py = pyridine
Ph = phenyl

In certain embodiments, the ROMP catalyst is a Grubbs-Hoveyda catalyst. In certain embodiments, the Grubbs-Hoveyda catalyst is selected from the group consisting of:

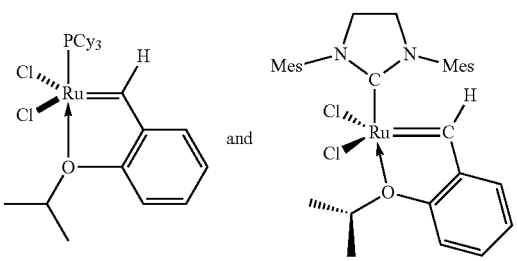

and

In certain embodiments, the ROMP catalyst is selected from the group consisting of:

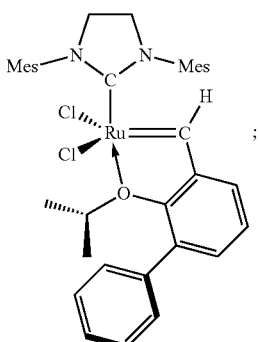

Blechart Catalyst

-continued

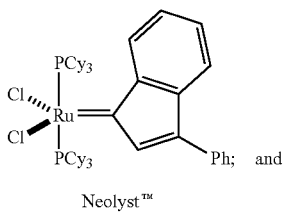

Neolyst™

In certain embodiments, the ROMP catalyst is of the formula:

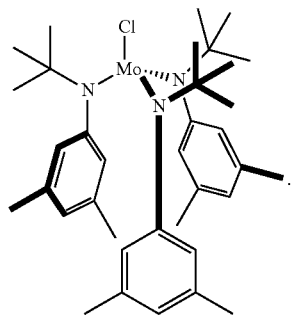

The ROMP can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

The ROMP can be quenched with a vinyl ether of the formula

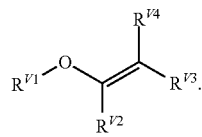

Each of $R^{V1}$, $R^{V2}$, $R^{V3}$, and $R^{V4}$ is independently optionally substituted alkyl, optionally substituted alkenyl, optionally substituted alkynyl, optionally substituted carbocyclyl, optionally substituted phenyl, optionally substituted heterocyclyl, or optionally substituted heteroaryl. In certain embodiments, $R^{V1}$ is optionally substituted alkyl, and $R^{V2}$, $R^{V3}$, and $R^{V4}$ are hydrogen. In certain embodiments, $R^{V1}$ is unsubstituted alkyl, and $R^{V2}$, $R^{V3}$, and $R^{V4}$ are hydrogen. In certain embodiments, $R^{V1}$ is substituted alkyl, and $R^{V2}$, $R^{V3}$, and $R^{V4}$ are hydrogen. In certain embodiments, $R^{V1}$ is methyl, and $R^{V2}$, $R^{V3}$, and $R^{V4}$ are hydrogen. In certain embodiments, $R^{V1}$ is ethyl, and $R^{V2}$, $R^{V3}$, and $R^{V4}$ are hydrogen. In certain embodiments, $R^{V1}$ is propyl, and $R^{V2}$, $R^{V3}$, and $R^{V4}$ are hydrogen. In certain embodiments, $R^{V1}$ is optionally substituted alkenyl, and $R^{V2}$, $R^{V3}$, and $R^{V4}$ are hydrogen. In certain embodiments, $R^{V1}$ is unsubstituted alkenyl, and $R^{V2}$, $R^{V3}$, and $R^{V4}$ are hydrogen. In certain embodiments, $R^{V1}$ is vinyl, and $R^{V2}$, $R^{V3}$, and $R^{V4}$ are hydrogen. In certain embodiments, at least one of $R^{V1}$, $R^{V2}$, $R^{V3}$, and $R^{V4}$ is conjugated with a diagnostic agent as defined above. In certain embodiments, the ROMP is quenched by ethyl vinyl ether. Excess ethyl vinyl ether can be removed from the Pt-BASPs by vacuum.

The Pt-BASPs can be multi-agent loaded star polymers. In certain embodiments, the inventive Pt-BASPs are capable of releasing multiple chemotherapeutic agents for combination therapy. In certain embodiments, the Pt-BASPs are capable of releasing two chemotherapeutic agents. In certain embodiments, the Pt-BASPs are capable of releasing three chemotherapeutic agents. In certain embodiments, the Pt-BASPs are capable of releasing four chemotherapeutic agents. In certain embodiments, the Pt-BASPs are capable of releasing five chemotherapeutic agents. In certain embodiments, the Pt-BASPs incorporate only a platinum-based agent which is introduced from the platinum-based complex crosslinkers. In certain embodiments, the inventive Pt-BASPs incorporate only cisplatin. In certain embodiments, the Pt-BASPs incorporate one or more therapeutic, diagnostic, or prophylactic agents. The one or more therapeutic, diagnostic, or prophylactic agents are introduced from macromonomers in the synthesis of Pt-BASPs. In certain embodiments, a therapeutic agent is incorporated in the macromonomer. In certain embodiments, an anti-cancer agent is incorporated in the macromonomer. In certain embodiments, the macromonomer is camptothecin (CPT) macromonomer. In certain embodiments, the macromonomer is doxorubicin (DOX) macromonomer. In certain embodiments, the inventive Pt-BASPs incorporate a platinum therapeutic agent and CPT. In certain embodiments, the inventive Pt-BASPs incorporate cisplatin and CPT. In certain embodiments, the inventive Pt-BASPs incorporate a platinum therapeutic agent, CPT, and DOX. In certain embodiments, the inventive Pt-BASPs incorporate cisplatin, CPT, and DOX. In certain embodiments, the one or more therapeutic, diagnostic, or prophylactic agents are connected to Pt-BASPs by a photocleavable linker. When the Pt-BASP is irradiated with light, DOX is released, and the IC50 of the Pt-BASPs have a lower value. In certain embodiments, the inventive Pt-BASPs incorporate a diagnostic agent and a platinum therapeutic agent. In certain embodiments, the inventive Pt-BASPs incorporate a prophylactic agent and a platinum therapeutic agent.

In certain embodiments, the Pt-BASPs are biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In certain embodiments, the solvents in step (a) is be same as the solvent of the platinum complex solution in step (b). In certain embodiments, the solvents in step (a) is different from the solvent of the platinum complex solution in step (b). Exemplary solvents for step (a) and platinum complex solution include, but are not limited to, methylene chloride, acetonitrile, chloroform, dimethylformamide, tetrahydrofuran, and acetone. Specific reaction conditions can be determined by those of ordinary skill in the art using no more than routine experimentation.

In certain embodiments of one type of macromonomer in Pt-BASPs, the amount of all the macromonomers, the platinum complex crosslinker, and the metathesis catalyst is of the molar ratio m:N:1, wherein m is an integer from 1 to 20, inclusive; and N is an integer from 1 to 20, inclusive. In certain embodiments, m is an integer from 3 to 12 inclusive. In certain embodiments, m is 1. In certain embodiments, m is 2. In certain embodiments, m is 3. In certain embodiments, m is 4. In certain embodiments, m is 5. In certain embodiments, m is 6. In certain embodiments, m is 7. In certain embodiments, m is 8. In certain embodiments, m is 9. In certain embodiments, m is 10. In certain embodiments, m is 11. In certain embodiments, m is 12. In certain embodiments, N is an integer from 1 to 10 inclusive. In certain embodiments, N is 1. In certain embodiments, N is 2. In certain embodiments, N is 3. In certain embodiments, N is 4. In certain embodiments, N is 5. In certain embodiments, N is 6. In certain embodiments, N is 7. In certain embodiments, N is 8. In certain embodiments, N is 9. In certain embodiments, N is 10. In certain embodiments, the amount of macromonomer, platinum complex crosslinker, and metathesis catalyst is of the ratio 5:3:1. In certain embodiments, the amount of macromonomer, platinum complex crosslinker, and metathesis catalyst is of the molar ratio 5:5:1. In certain embodiments, the amount of macromonomer, platinum complex crosslinker, and metathesis catalyst is of the molar ratio 5:7:1. In certain embodiments, the amount of macromonomer, platinum complex crosslinker, and metathesis catalyst is of the molar ratio 7:3:1. In certain embodiments, the amount of macromonomer, platinum complex crosslinker, and metathesis catalyst is of the molar ratio 7:5:1. In certain embodiments, the amount of macromonomer, platinum complex crosslinker, and metathesis catalyst is of the molar ratio 7:7:1. In certain embodiments, the amount of macromonomer, platinum complex crosslinker, and metathesis catalyst is of the molar ratio 11:1:1. In certain embodiments, the amount of macromonomer, platinum complex crosslinker, and metathesis catalyst is of the molar ratio 11:3:1. In certain embodiments, the amount of macromonomer, platinum complex crosslinker, and metathesis catalyst is of the molar ratio 11:5:1.

In certain embodiments of multi-agent loaded Pt-BASPs, the amount of the first macromonomer, second macromonomer, and platinum complex crosslinker is of the molar ratio of m1:m2:N, wherein m1 and m2 are each independently an integer from 1 to 20, inclusive; and N is an integer from 1 to 20, inclusive. In certain embodiments, the amount of the first macromonomer, second macromonomer, and platinum complex crosslinker is of the molar ratio of 3:4:3. In certain embodiments, the amount of the first macromonomer, second macromonomer, and platinum complex crosslinker is of the molar ratio of 4:3:3. In certain embodiments of more than one types of macromonomers in the multi-agent loaded Pt-BASPs, the amount of the first macromonomer, second macromonomer, and platinum complex crosslinker is of the molar ratio of m1:m2:N:1, wherein m1 and m2 are each independently an integer from 1 to 20, inclusive; and N is an integer from 1 to 20, inclusive. In certain embodiments, the amount of the first macromonomer, second macromonomer, and platinum complex crosslinker is of the molar ratio of 3:4:3:1. In certain embodiments, the amount of the first macromonomer, second macromonomer, and platinum complex crosslinker is of the molar ratio of 4:3:3:1.

Figure 5A:
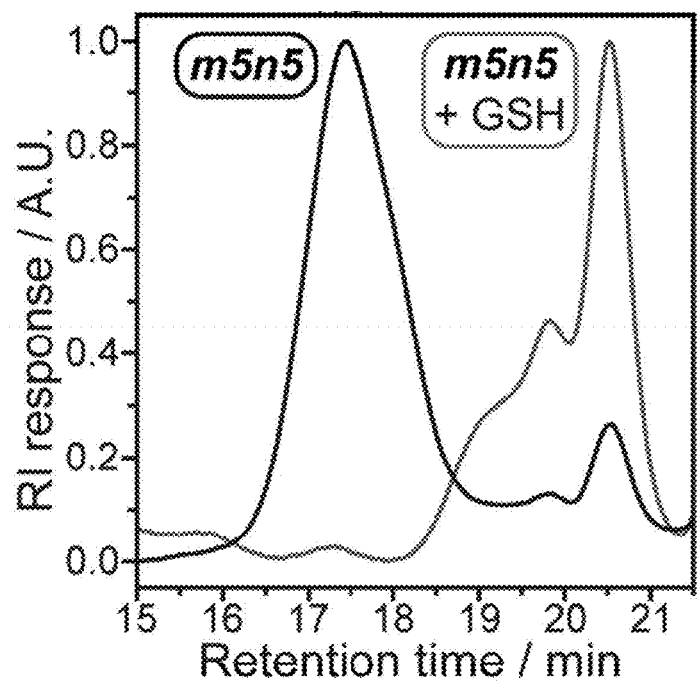
FIG. 5A shows GPC traces before and after exemplary cisplatin-based Pt-BASPs degradation in the presence of glutathione (GSH). Exposure of a Pt-BASP (m5N5) sample to excess glutathione (GSH) reducing agent in deionized water led to complete degradation of the Pt-BASP as confirmed by GPC.
Figure 5B:
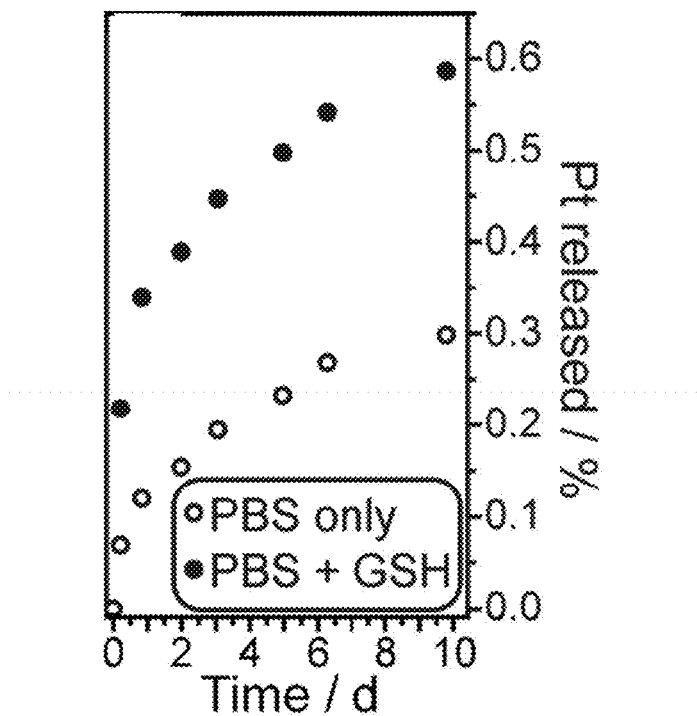
FIG. 5B shows release kinetics curve of exemplary cisplatin carried by m5N5 sample. Two sets of conditions were explored: first, the Pt-BASP was dialyzed against 100 mL of PBS at pH 7.4 and 37° C.; second, the Pt-BASP was dialyzed against 100 mL of 10 mM GSH in PBS at pH 7.4 and 37° C. The former conditions mimic extracellular media, whereas the latter mimic the reducing intracellular environment. The Pt content from samples of the solution outside the dialysis membrane was obtained by inductively coupled plasma atomic emission spectroscopy (ICP-AES). Data for % Pt released versus time are shown in FIG. 5B. Under both sets of conditions, extended release of Pt was observed over the course of 10 d. In the presence of GSH the % Pt released was 50% after 5 d, and reached 60% after 10 d. In the absence of GSH, the % Pt released was 30% after 10 d. The presence of GSH led to a significant burst release over the first 2 d followed by an extended period of linear release. These results indicate that Pt-BASPs may be useful architectures for triggered intracellular release of cisplatin. From the release kinetics experiment, only a fraction (~39% for the GSH sample) of the cisplatin carried by m5N5 is released within 48 h.
Figure 5C:
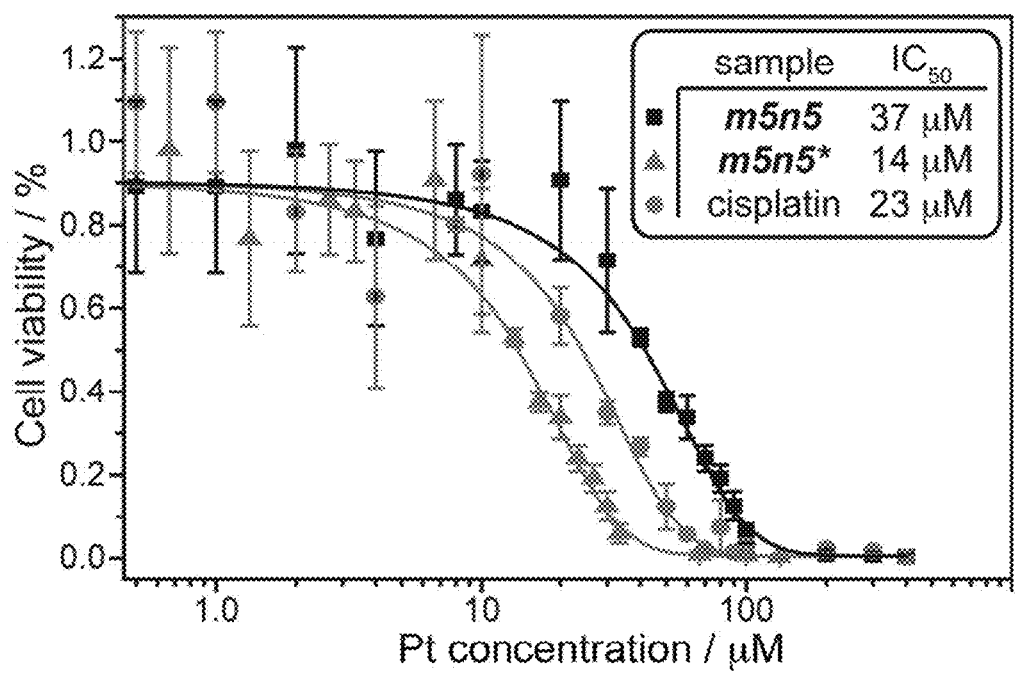
FIG. 5C shows HeLa cell viability in the presence of m5N5 and free cisplatin (compound 1) as quantified by MTT assay. The cells were exposed to solutions of Pt-BASP or free cisplatin with varied total Pt concentration for 48 hours.
Figure 6:
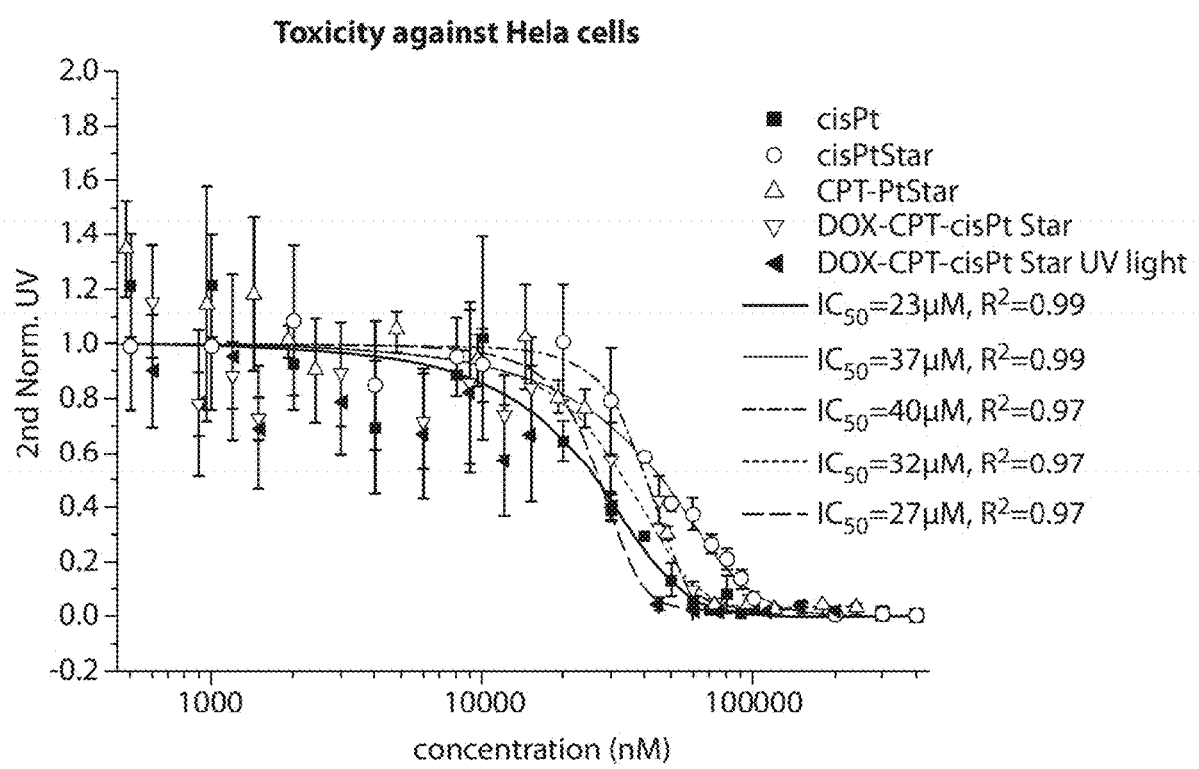
FIG. 6 shows the toxicity of exemplary Pt-BASPs against Hela cells. The various Pt-BASPs carry either Pt alone, Pt and camptothecin (CPT), or PT and CPT and doxorubicin (DOX). The DOX is connected to Pt-BASPs by a photo-cleavable linker. When the Pt-BASP is irradiated with light, DOX is released, and the $IC_{50}$ is shifted to a lower value. These Pt-BASP particles are capable of releasing 3 different chemotherapeutic agents for combination therapy.
Figure 7:
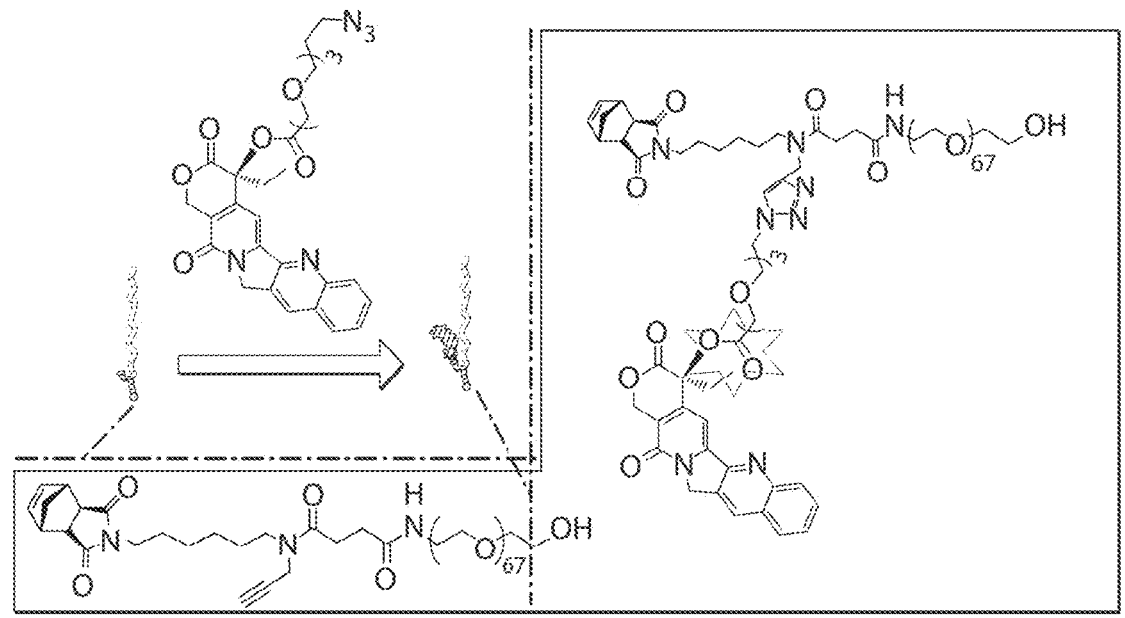
FIG. 7 shows an exemplary camptothecin-loaded macromonomer (CPT-MM) and doxorubicin-loaded macromonomer (Dox-MM).
Figure 7:
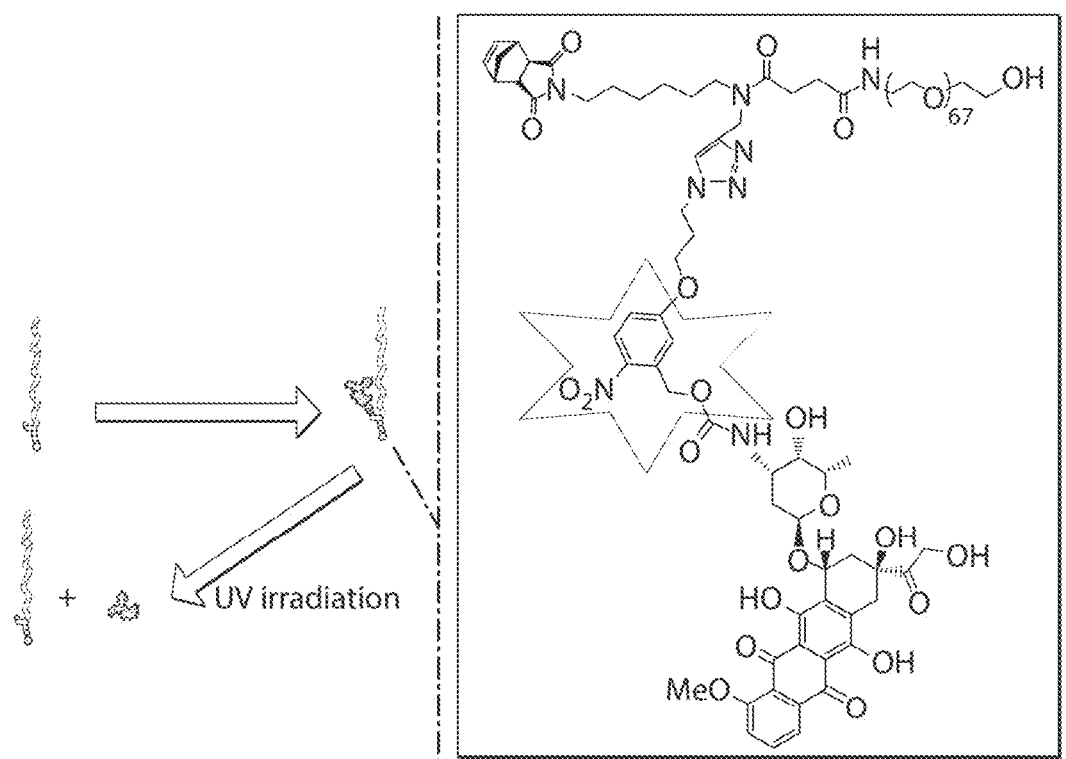
Figure 8A:
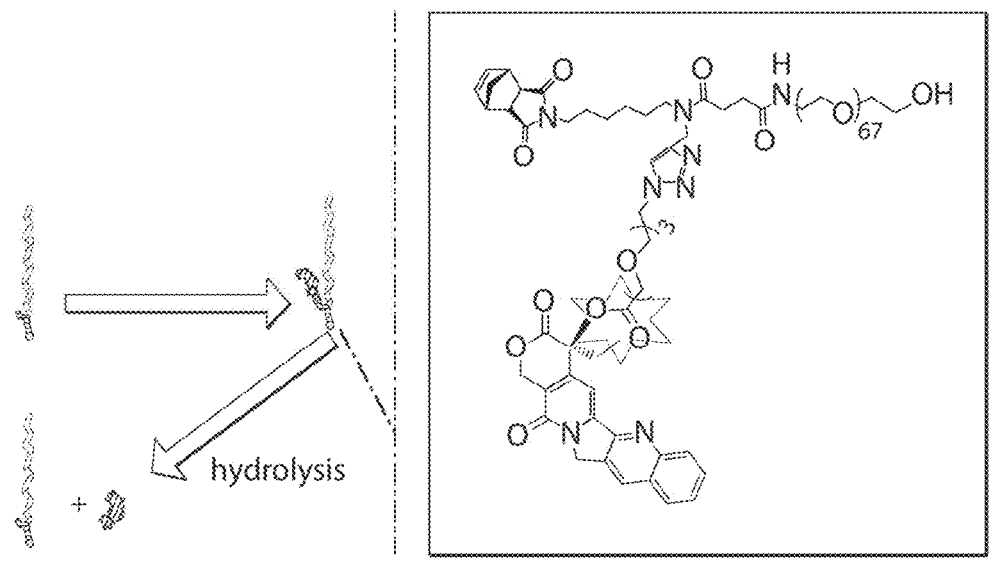
FIG. 8A shows release of camptothecin from a camptothecin-loaded macromonomer.
Figure 8B:
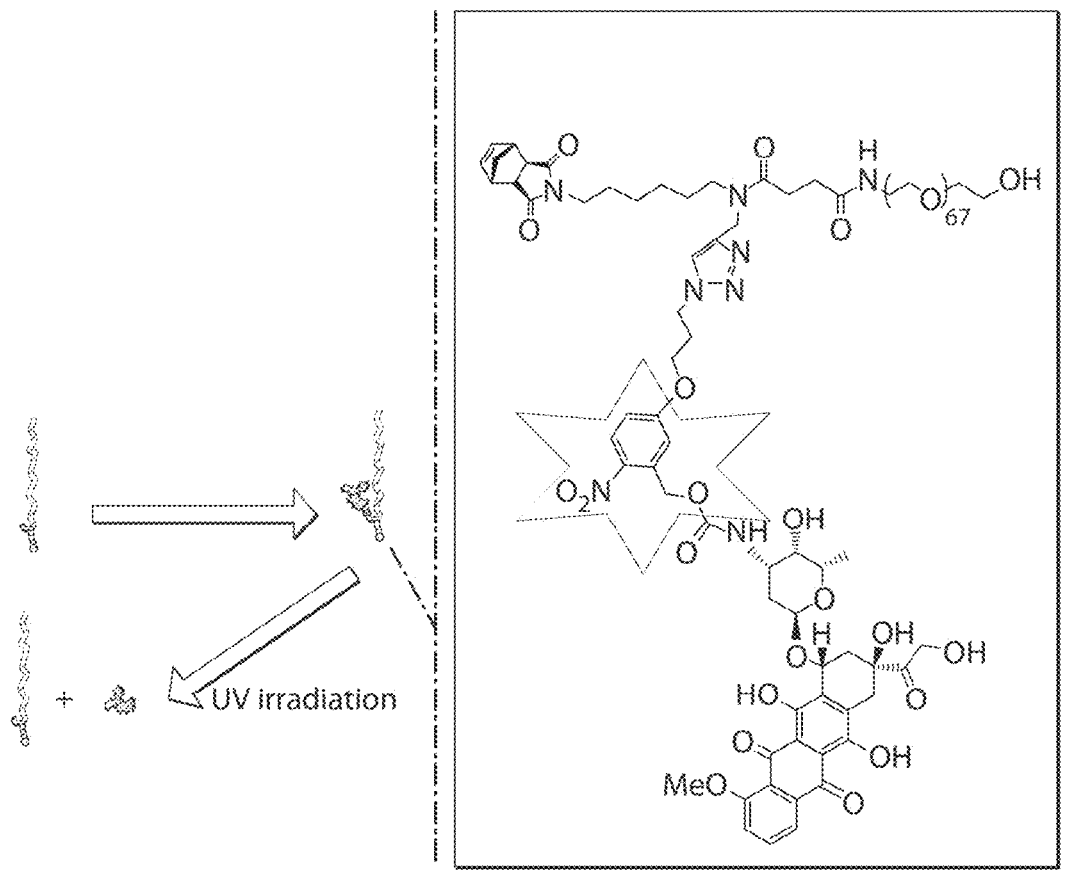
FIG. 8B shows release of doxorubicin from a doxorubicin-loaded macromonomer.
Figure 9A:
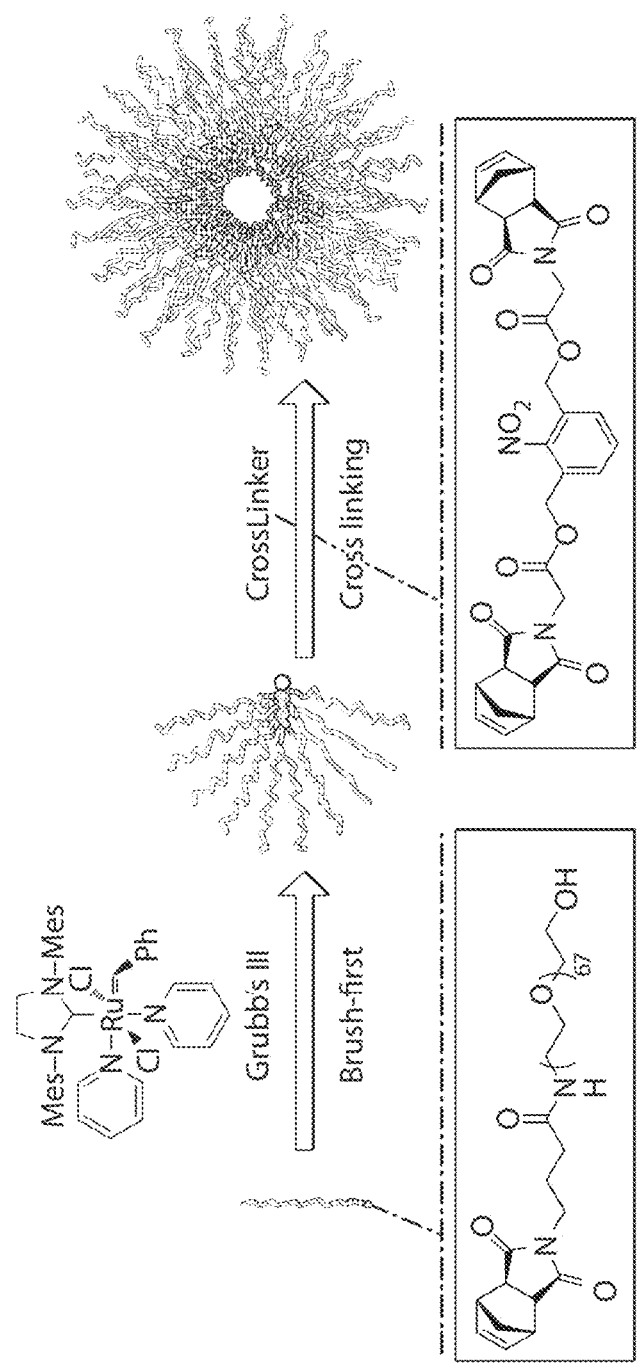
FIG. 9A shows Brush-First synthesis of nanoparticles from a doxorubicin-loaded macromonomer (Dox-MM).
Figure 9B:
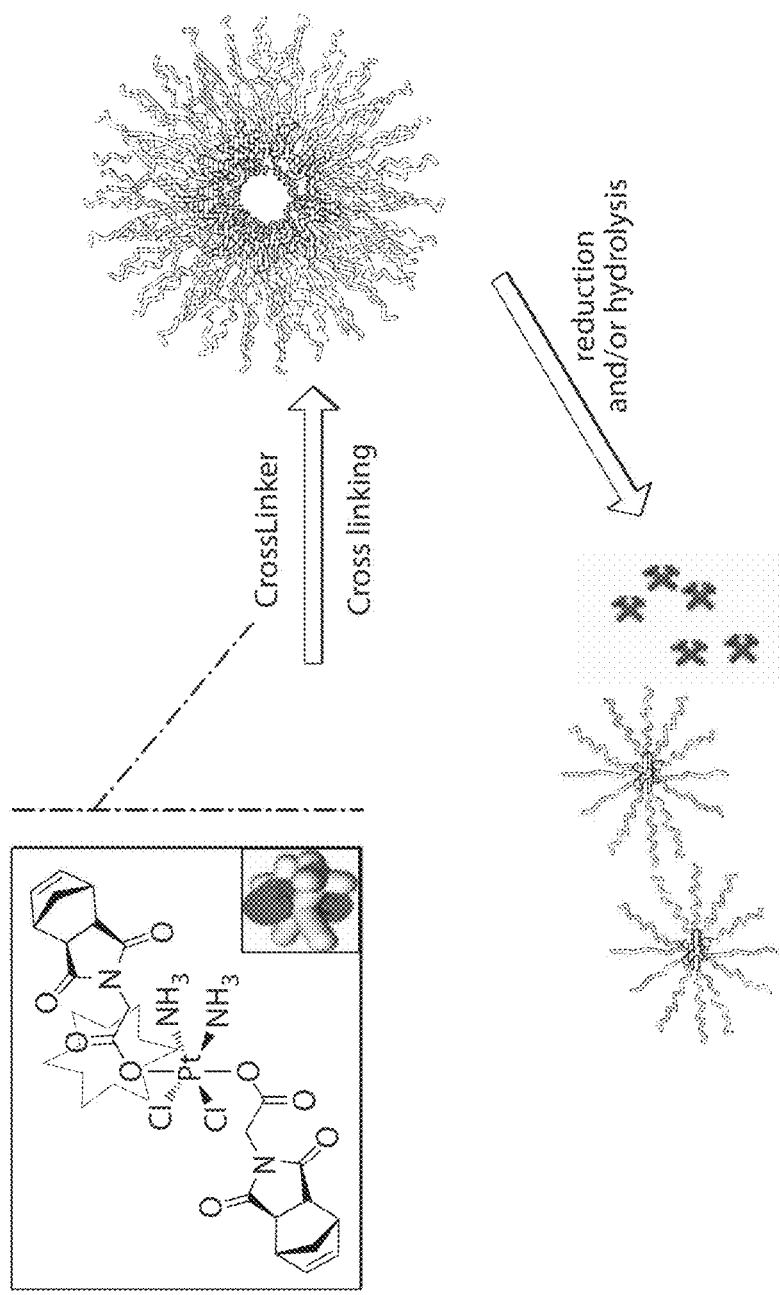
FIG. 9B shows use of an exemplary platinum-based cross-linker in the Brush-First synthesis of nanoparticles.
Figure 10:
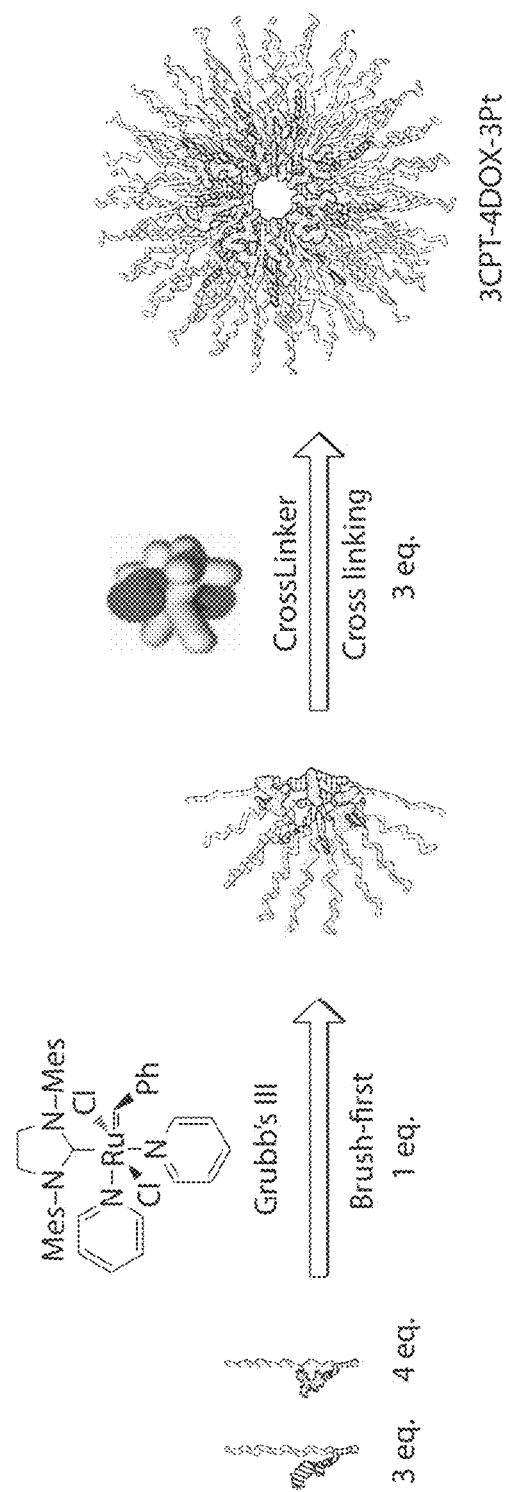
FIG. 10 shows synthesis of exemplary multi-drug loaded nanoparticles, 3CPT-4DOX-3Pt, using "brush-first" ring-opening metathesis polymerization (ROMP). The exemplary nanoparticles are prepared from 3 equivalents of CPT-MM (see FIG. 7), 4 equivalents of Dox-MM (see FIG. 7), and 3 equivalents of the platinum-based cross-linker (see FIG. 9B).
Figure 11:
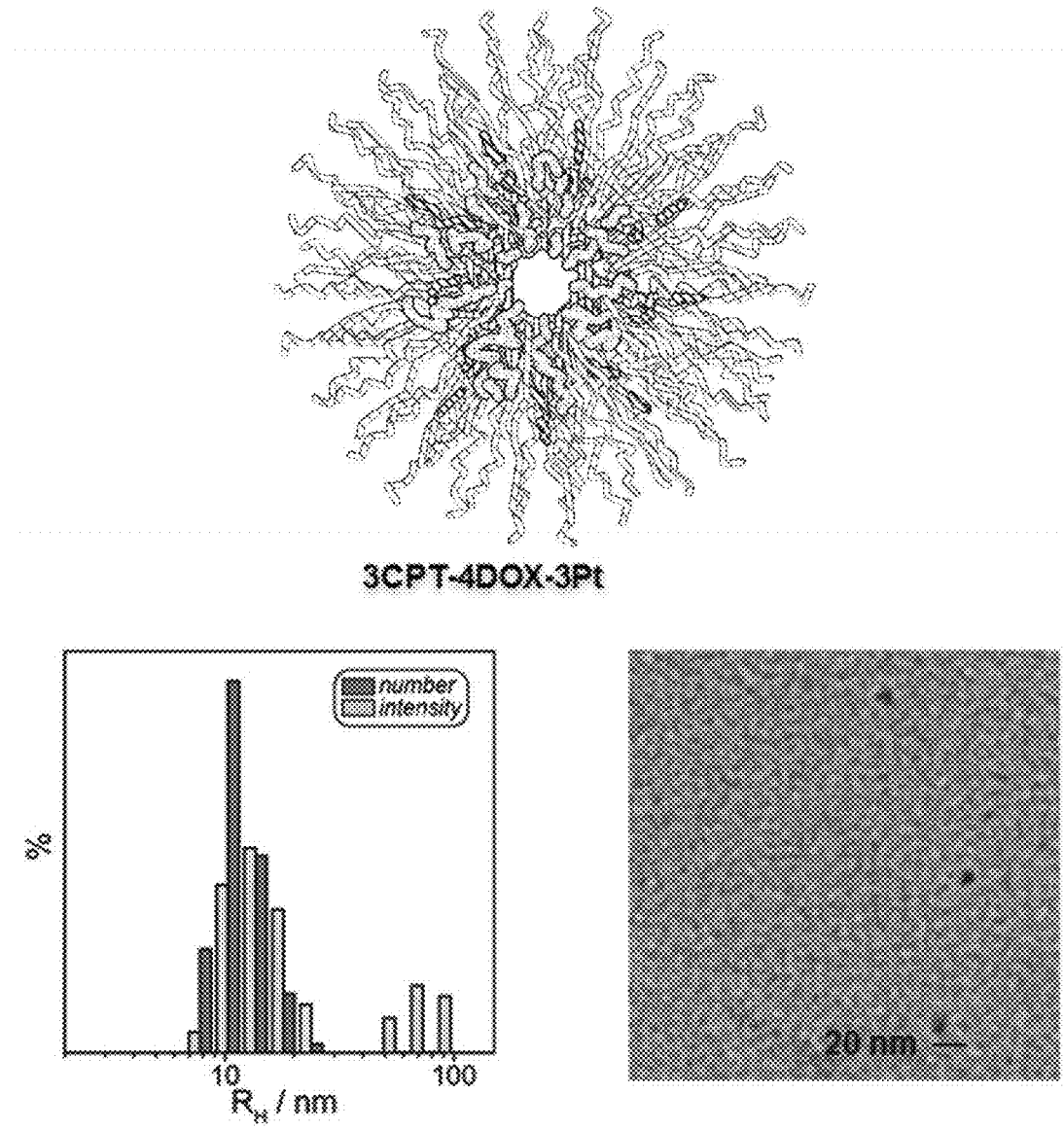
FIG. 11 shows characterization of the exemplary multi-drug loaded nanoparticle 3CPT-4DOX-3Pt.
Figure 12:
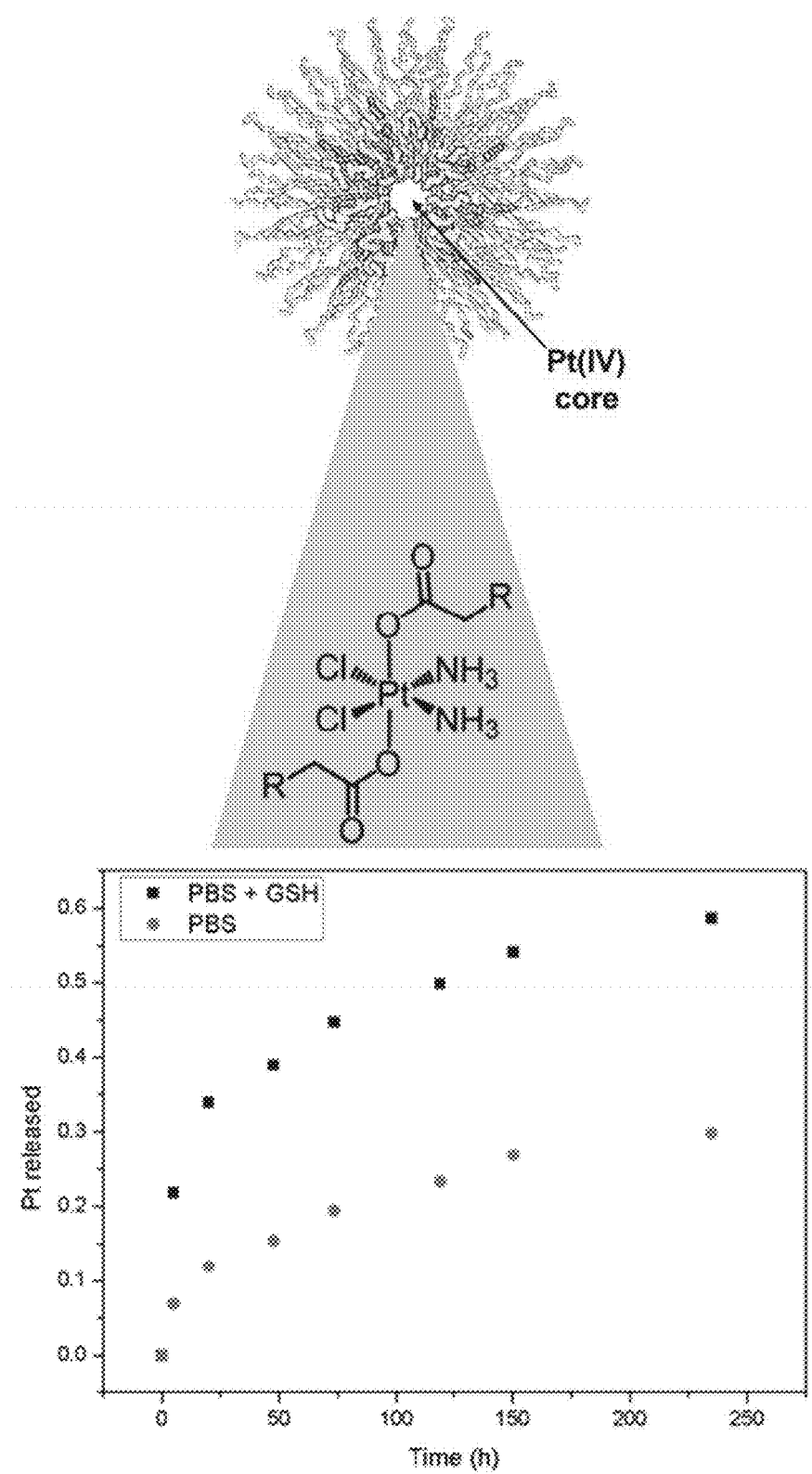
FIG. 12 shows the Pt-release from the exemplary multi-drug loaded nanoparticle 3CPT-4DOX-3Pt.
Figure 13:
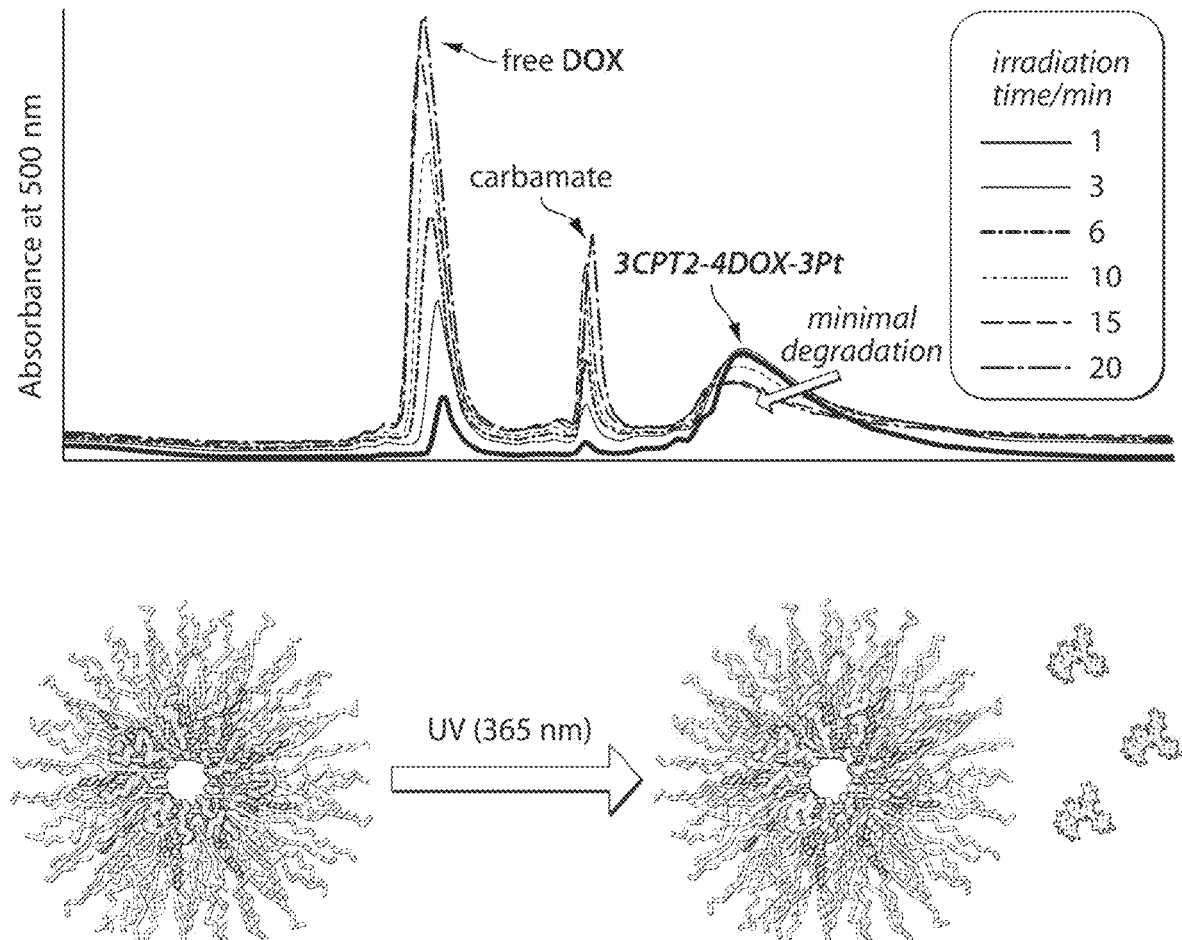
FIG. 13 shows UV-absorbance changes over 1 min, 3 min, 6 min, 10 min, 15 min, and 20 min during the drug release from the exemplary multi-drug loaded nanoparticle 3CPT-4DOX-3Pt.
Figure 14A:
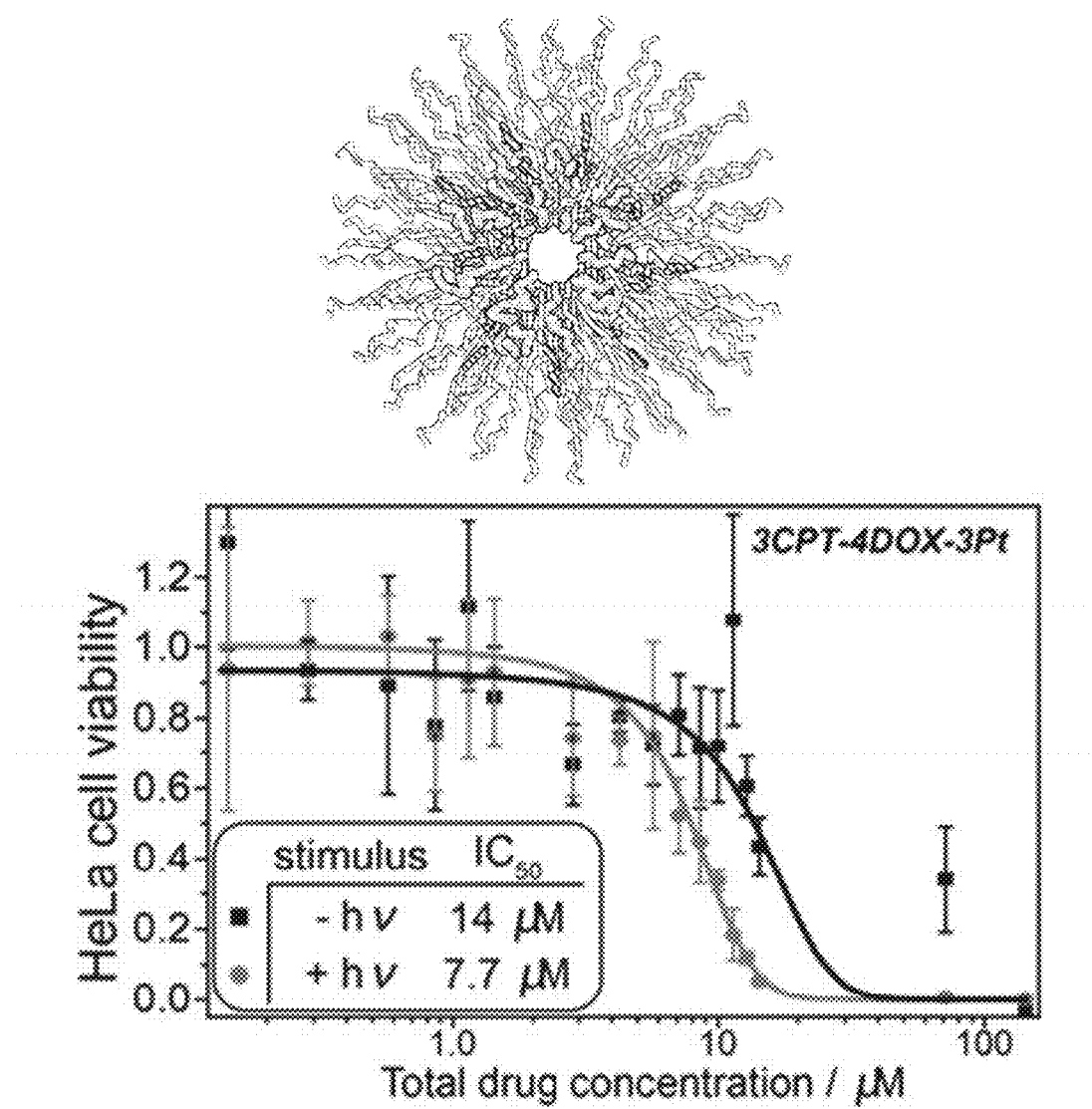
FIG. 14A shows in vitro cytotoxicity of the exemplary multi-drug loaded nanoparticle 3CPT-4DOX-3Pt against Hela cells.
Figure 14B:
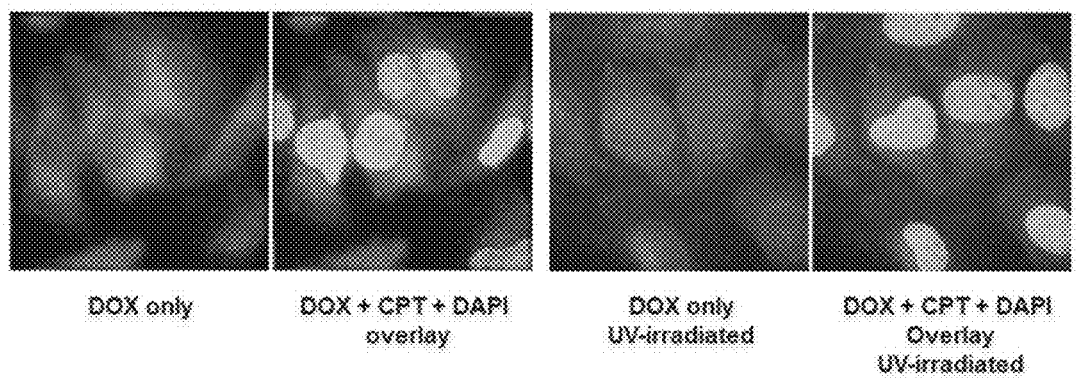
FIG. 14B shows exemplary internalization results of 3CPT-4DOX-3Pt into Hela cells. DAPI: 4',6-diamidino-2-phenylindole.

Exposure to physiologically relevant conditions can lead to the Pt-BASPs degradation and controlled, extended release of platinum-based agents. In certain embodiments, the release rate can increased by addition of GSH. In vitro cytotoxicity assays demonstrates that Pt-BASPs effectively kill cancer cells (FIG. 5).

Pharmaceutical Compositions, Kits, and Administration

The present invention provides pharmaceutical compositions comprising Pt-BASPs, as described herein, and optionally a pharmaceutically acceptable excipient. In certain embodiments, the Pt-BASPs are provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the Pt-BASPs into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80)), polyoxyethylene esters (e.g. polyoxyethylene monostearate (MYRJ 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers. (e.g. polyoxyethylene lauryl ether (BRIJ 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste); gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzethonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS, PHENONIP, methylparaben, GERMALL 115, GERMABEN II, NEOLONE, KATHON, and EUXYL.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution. U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin. (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

Dosage forms for topical and/or transdermal administration of a compound of this invention may include ointments, pastes, creams, lotions, gels, powders, solutions, sprays, inhalants and/or patches. Generally, the Pt-BASPs are admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles of Pt-BASPs described herein. Such compositions are conveniently in the form of dry powders for administration using a device comprising a dry powder reservoir to which a stream of propellant can be directed to disperse the powder and/or using a self-propelling solvent/powder dispensing container.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the Pt-BASPs in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the Pt-BASPs and having an average particle from about 0.2 to 500 micrometers. Such a formulation is administered by rapid inhalation through the nasal passage from a container of the powder held close to the nares.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Pt-BASPs provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The Pt-BASPs and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of the inventive polymer for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the inventive polymer may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise the Pt-BASPs described herein, or a pharmaceutical composition thereof, and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Methods of Treatment and Uses

The present invention also provides methods of using the Pt-BASPs described herein, or a pharmaceutical composition thereof, for the treatment or prevention of a proliferative disease such as cancer (e.g. lung cancer, large bowel cancer, pancreas cancer, biliary tract cancer, or endometrial cancer), benign neoplasm, angiogenesis, inflammatory disease, autoinflammatory disease, or autoimmune disease in a subject.

In some embodiments, the Pt-BASPs described herein, or a pharmaceutical composition thereof are useful in treating a cancer. In some embodiments, the Pt-BASPs described herein, or a pharmaceutical composition thereof, are useful to delay the onset of, slow the progression of, or ameliorate the symptoms of cancer. In some embodiments, the Pt-BASPs described herein, or a pharmaceutical composition thereof, are administered in combination with other compounds, drugs, or therapeutics to treat cancer.

In some embodiments, the Pt-BASPs described herein, or a pharmaceutical composition thereof are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLUSLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, the Pt-BASPs described herein, or a pharmaceutical composition thereof, are useful in treating lung cancer, head-and-neck cancer, esophagus cancer, stomach cancer, breast cancer, pancreas cancer, liver cancer, kidney cancer, prostate cancer, glioblastomas, metastatic melanomas, peritoneal or pleural mesotheliomas.

In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

In certain embodiments, the methods described herein include administering to a subject with an effective amount of the Pt-BASPs described herein, or a pharmaceutical composition thereof. In certain embodiments, the methods described herein include implanting to a subject with an effective amount of the Pt-BASPs described herein, or a pharmaceutical composition thereof.

In certain embodiments, the Pt-BASPs described herein, or a pharmaceutical composition thereof, are administered in combination with one or more additional pharmaceutical agents described herein. In certain embodiments, the additional pharmaceutical agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrelin and leuprolide), antiandrogens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g., mercaptopurine and Thioguanine). Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AGO13736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer). GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

EXAMPLES

In order that the invention described herein may be more fully understood, the following examples are set forth. It should be understood that these examples are for illustrative purposes only and are not to be construed as limiting this invention in any manner.

All reagents and solvents were purchased from Aldrich or VWR and used as supplied unless otherwise noted. Platinum complexes 1 and 2 (Hall et al. *J. Biol. Inorg. Chem.* 2003, 8, 726), ruthenium catalyst C-1 (cat.; Love, J. A.; Morgan, J. P.; Trnka, T. M.; Grubbs. R. H. *Angew. Chem. Int. Ed.* 2002, 41, 4035), N-(glycine)-cis-5-norbornene-exo-dicarboximide 5 (a1) (Conrad, R. M.; Grubbs. R. H. *Angew. Chem. Int. Ed.* 2009, 48, 8328), and norbornene-PEG MM (PEG-MM, 4) (Liu, J.; Burts, A. O.; Li, Y.; Zhukhovitskiy, A. V.; Ottaviani, M. F.; Turro, N. J.; Johnson, J. A. *J. Am. Chem. Soc.* 2012, 134, 16337), were prepared according to literature procedures. Degassed dichloromethane (DCM) and tetrahydrofuran (THF) were passed through solvent purification columns prior to use.

Liquid chromatography-mass spectrometry (LC/MS) and preparative HPLC were performed on an Agilent 1260 LC system equipped with a Zorbax SB-$C_{18}$ rapid resolution HT column and a Zorbax SB-$C_{18}$ semi-preparative column. Solvent gradients consisted of mixtures of nano-pure water with 0.1% acetic acid (AcOH) and HPLC-grade acetonitrile. Mass spectra were obtained using an Agilent 6130 single quadrupole mass spectrometer.

Dynamic light scattering (DLS) measurements were made at room temperature using a Brookhaven ZetaPALS DLS instrument or a Wyatt Technology DynaPro Titan DLS instrument. Samples were dissolved in nanopure water at a concentration of ~1 mg/mL. A fresh, clean, polystyrene cuvette was washed with compressed air to remove dust. The sample solution was passed through a 0.4 μm TEFLON syringe filter directly into the cuvette; the cuvette was capped and placed in the DLS instrument for particle sizing. At least 3 measurements were made per sample and average hydrodynamic diameters were calculated by fitting the DLS correlation function using the CONTIN routine (ISDA software package from Brookhaven instruments or Dynamics V6 software package from DynaPro Wyatt Technology).

$^1$H nuclear magnetic resonance ($^1$H-NMR), $^{13}$C nuclear magnetic resonance ($^{13}$C-NMR), and $^{195}$Pt nuclear magnetic resonance ($^{195}$Pt-NMR) spectra were recorded on Bruker AVANCE-400 NMR spectrometer. Mercury 300 MHz spectrometer, or INOVA 500 MHz spectrometer. Chemical shifts are reported in ppm and referenced to the CHCl3 singlet at 7.26 ppm, DMSO at 2.50 ppm or $CH_2Cl_2$ at 5.30 ppm. $^{13}$C-NMR spectra were referenced to the center line of the $CDCl_3$ triplet at 77.0 ppm, DMSO septet at 39.5 ppm or $CD_2Cl_2$ quintet at 54.0 ppm. $^{195}$Pt-NMR spectra were referenced using an external $K_2PtCl_6$ in $D_2O$ at −1628 ppm. Chemical shifts are expressed in parts per million (ppm), and splitting patterns are designated as s (singlet), d (doublet), t (triplet), m (multiplet) and br (broad). Coupling constants J are reported in Hertz (Hz). Nuclear magnetic resonance (NMR) experiments were performed on either a Mercury 300 MHz spectrometer or an INOVA 500 MHz spectrometer. MESTRENOVA NMR 7.0.1 software was used to analyze the NMR spectra.

Gel permeation chromatography (GPC) measurements were performed on an Agilent 1260 LC system with two Shodex KD-806M GPC columns in series at 60° C., and a flow rate of 1 mL/min. N,N-Dimethyl formamide (DMF) with 0.2 M LiBr was used as the eluent. A T-rEX refractive index detector (Wyatt) and a DAWN EOS 18 angle light scattering (MALS) detector (Wyatt) were used for polymer analysis.

High-resolution mass spectrometry (HRMS) was obtained using a Bruker Daltonics APEXIV 4.7 Tesla Fourier Transform Ion Cyclotron Resonance Mass Spectrometer (FT-ICR-MS).

TEM images were obtained at the MIT Center for Materials Science and Engineering on a JEOL 200CX TEM instrument equipped with a 1 k×1 k CCD camera. The samples were prepared as follows: 5.0 μL of a 0.050 mg/mL solution of 20xL (or 15xL) Pt-BASPs was deposited via pipet on top of a carbon film-coated 200-mesh copper grid (purchased from Electron Microscopy Sciences) placed on a piece of PARAFILM carbon-coated side up. The sample was allowed to dry at room temperature and then ready for TEM imaging.

Photolysis experiments were performed using a Multiple Ray Lamp (UVP) fitted with an 8 W, long wave, filtered blacklight bulb (365 nm).

OVCAR3 cells (ATCC) were maintained in RPMI-1640 media supplemented with 0.01 mg/mL recombinant human insulin (Gibco), 20% fetal bovine serum, and penicillin/streptomycin in a 5% $CO_2$ humidified atmosphere (37° C.). Assays and imaging were performed on cells passaged 12-24 h prior. Dose-response curves were fit using a four-parameter logistic regression analysis and statistical significance was assessed by two-tailed t-test (95% CI) for *P<0.01. P<0.05, and *P<0.001. Pt-BASPs described herein were reconstituted in ultrapure water (18 MS) containing 5% D-glucose and stored at 4° C. in dark prior to use. Viability was assessed by CELLTITER-GLO assay (Promega) following 72 h total incubation time with MDLP-spiked OPTIMEM medium. 90 min after the introduction of the Pt-BASPs, assay plates were exposed for 10 min with a portable UV lamp (UVP Inc; 2.0±0.3 mW/cm² at 365 nm) and returned to the incubator. Confocal fluorescence measurements were performed following incubation with 133 μM acridine orange (Sigma) and 66.6 μg/mL Pt-BASP in complete basal medium. After 30 min, cell growth media were replaced with 10 mM HEPES (pH 7.4) containing 10% FBS and imaging (1 exposure min$^{-1}$) was performed using the 405, 488, and/or 561 nm laser lines of a Nikon 1AR ultra-fast spectral scanning confocal microscope ($\lambda_{em}$: 525/50, 595/50 nm) fitted with a temperature-controlled environment chamber and 60× oil immersion objective.

Example 1. Preparation of XL3 Pt(IV) Cisplatin Prodrug

Synthesis of Norbornene Anhydride 3

N-(glycine)-cis-5-norbornene-exo-dicarboximide 5 (760 mg, 3.4 mmol) and N,N'-Dicyclohexylcarbodiimide (DCC) (360 mg, 1.7 mmol) were dissolved in anhydrous DCM (60 mL) and the resulting solution was stirred at room temperature overnight. The reaction mixture was then filtered and the filtrate was concentrated via rotary evaporator to give 3 as white solid (583 mg, 80% yield). $^1$H NMR (400 MHz, CDCl$_3$) δ 6.31 (t, J=1.8 Hz, 2H), 4.38 (s, 2H), 3.35-3.31 (m, 2H), 2.78 (d, J=1.4 Hz, 2H), 1.65 (d, J=10.1 Hz, 1H), 1.54 (dt, J=10.1, 1.4 Hz, 1H). $^{13}$C NMR (101 MHz, CDCl$_3$) δ 176.6, 161.6, 138.0, 48.1, 45.4, 42.9, 39.9. IR (neat): 1701, 1709, 1411, 1079 cm$^{-1}$. MS (ESI) m/z (M+Li)$^+$ calculated for $C_{22}H_{20}N_2O_7Li$: 431.1; observed: 431.1.

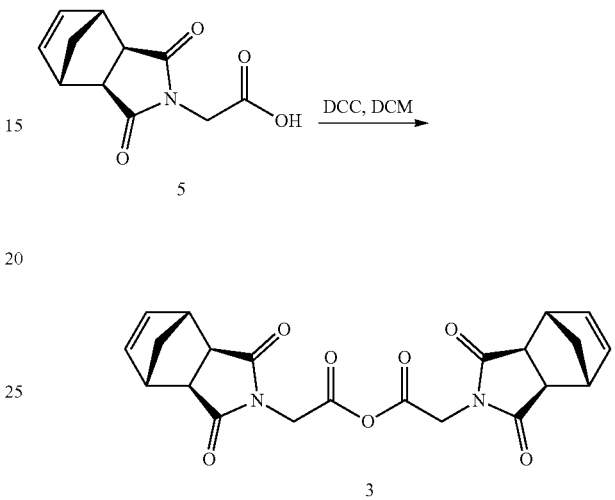

Synthesis of Cross-Linker XL3

Norbomene anhydride 3 (550 mg, 1.3 mmol) and platinum complex 2 (100 mg, 0.30 mmol) were dissolved in anhydrous DCM (10 mL), and the resulting solution was stirred at room temperature for 2 weeks. The reaction mixture was then filtered, and the residue solid was washed with DCM (20 mL×3). The solid was collected and dried in vacuo to give XL3 (white solid, 199 mg, 90% yield). $^1$H NMR (500 MHz, DMSO-d$_6$) δ 6.50 (s, br, 6H), 6.31 (s, 4H), 4.13 (s, 4H), 3.10 (s, 4H), 2.70 (s, 4H), 1.66 (d, J=9.0 Hz, 2H), 1.32 (d, J=9.0 Hz, 2H). $^{13}$C NMR (101 MHz, DMSO-d$_6$) δ 176.8, 174.0, 137.8, 47.2, 44.6, 42.6. (NOTE: one peak for the compound is buried under the solvent picks.) $^{195}$Pt NMR (86 MHz, DMSO-d$_6$) δ 1234.3. IR (neat): 1712, 1682, 1246, 1178 cm$^{-1}$. MS (ESI) m/z (M+H)$^+$ calculated for $C_{22}H_{27}Cl_2N_4O_8Pt$: 741.0837; observed: 741.0837.

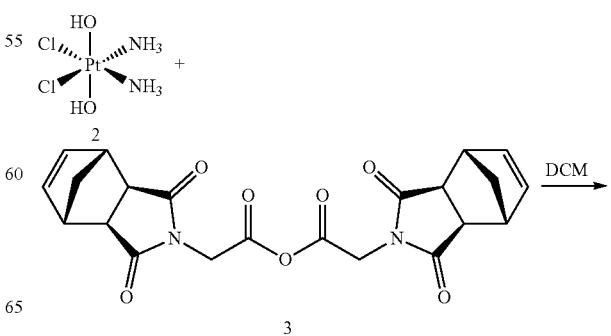

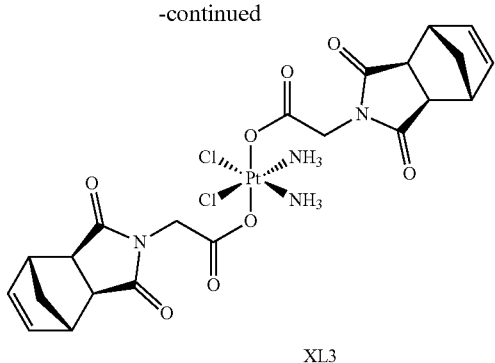

XL3

Example 2. Preparation of Macromonomer DOX-MM

Figure 15A:
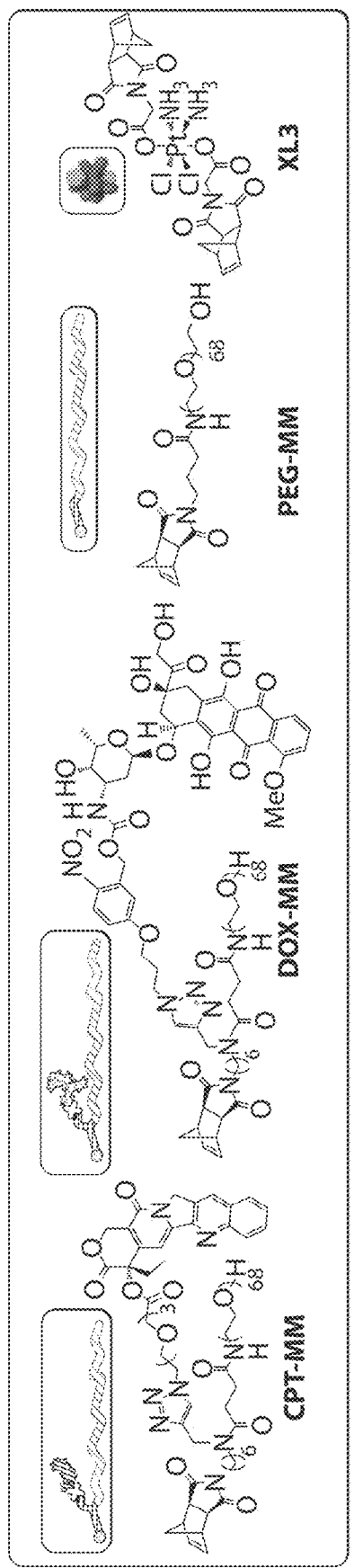
FIG. 15A shows the chemical structures exemplary macromonomers.
Figure 15B:
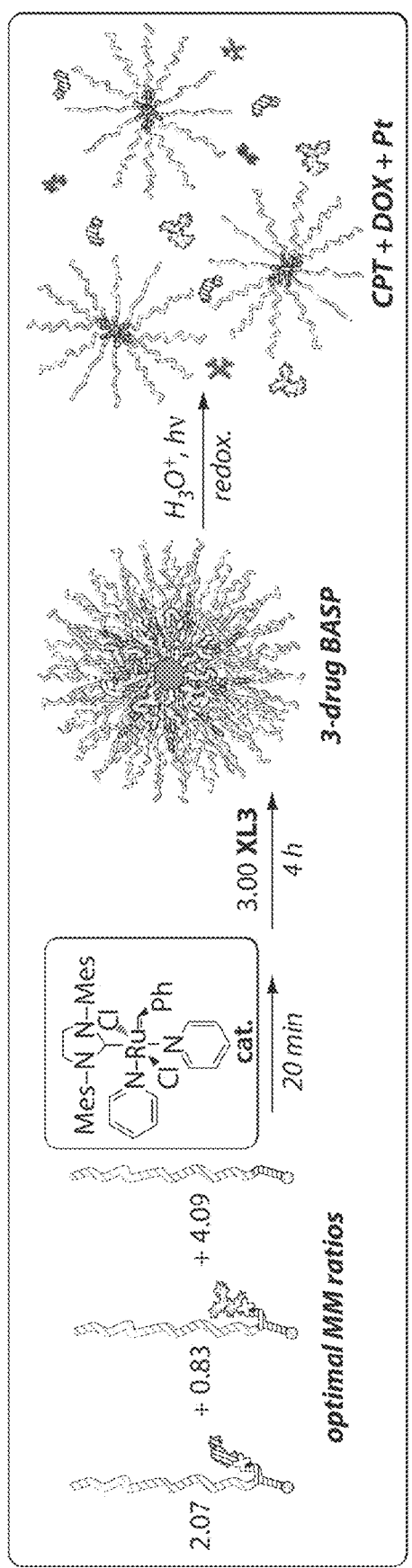
FIG. 15B shows an exemplary synthesis of polymer P3 (3-drug BASP). Orthogonal drug release occurs in response to three distinct triggers (e.g., $H_3O^+$ (hydrolysis), hv (UV irradiation), and redox. (reduction)). Pt: cisplatin.

Two macromonomers CPT-MM and DOX-MM (FIG. 15A) were prepared. CPT-MM and DOX-MM are branched MMs (Burts, A. O.; Li, Y. J.; Zhukhovitskiy, A. V.; Patel, P. R.; Grubbs, R. H.; Ottaviani, M. F.; Turro, N. J.; Johnson. J. A. *Macromolecules* 2012, 45, 8310) that release unmodified CPT and DOX in response to acidic media (Chen, X.; McRae, S.; Parelkar, S.; Emrick, T. *Bioconjugate Chem.* 2009, 20, 2331) and long-wavelength UV light, respectively. Both MMs feature a 3 kDa poly(ethylene glycol) (PEG) chain that confers water solubility and neutral surface charge to the final Pt-BASPs (Greenwald, R. B.; Choe, Y. H.; McGuire, J.; Conover. C. D. *Adv. Drug Delivery Rev.* 2003, 55, 217; Arvizo, R. R.; Miranda, O. R.; Moyano, D. F.; Walden, C. A.; Giri, K.; Bhattacharya, R.; Robertson, J. D.; Rotello, V. M.; Reid, J. M.; Mukherjee. P. *PLoS One* 2011, 6).

Synthesis of 5-(3-chloropropoxy)-2-nitrobenzaldehyde b2

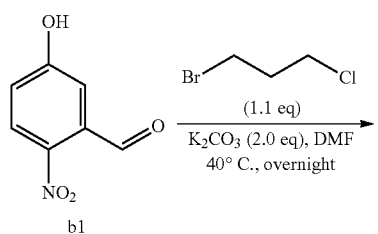

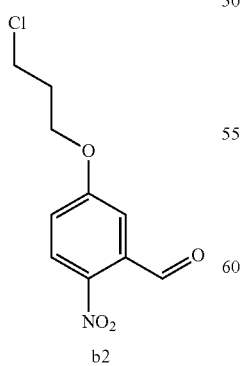

Compound b2 may be prepared according to reported methods (see, e.g., Gumbley, P.; Koylu, D.; Thomas. S. W. *Macromolecules* 2011, 44, 7956). 1-Bromo-3-chloropropane (0.650 mL, 0.00658 moles) was added to a solution of 5-hydroxy-2-nitrobenzaldehyde (1.0 g. 0.00598 moles), and potassium carbonate (1.66 g, 0.0120 moles) in anhydrous DMF (6 mL). The solution was stirred at 40° C. for 24 hours. The reaction was diluted with ethyl acetate (75 mL) and washed with saturated sodium bicarbonate solution (75 mL), water (75 mL), and brine (75 mL). The organic layer was dried with anhydrous magnesium sulfate, which was removed by filtration. The filtrate was concentrated, and the resulting residue was subject to silica gel chromatography using a gradient of 100% hexanes to 50% ethyl acetate in hexanes. The fractions containing the product were collected, and volatiles were removed by rotary evaporation. The resulting residue was dried overnight to yield 5-(3-chloropropoxy)-2-nitrobenzaldehyde as a bright-green yellow solid (yield 87%*). $^1$H NMR (400 MHz, CD$_2$Cl$_2$) δ 10.42 (s, 1H), 8.15 (d, J=9.1 Hz, 1H), 7.32 (d, J=2.9 Hz, 1H), 7.18 (dd, J=9.0, 2.9 Hz, 1H), 4.27 (t, J=5.9 Hz, 2H), 3.76 (t, J=6.3 Hz, 2H), 2.35-2.24 (m, 2H). $^{13}$C-NMR (100 MHz, CD$_2$Cl$_2$) δ 189.05, 163.84, 135.04, 127.84, 119.16, 114.57, 66.28, 41.74, 32.35 HRMS m/z: calculated for C$_{10}$H$_{10}$ClNO$_4$ [M+H]$^+$, 244.0371, found, 244.0366.

*Observed extra peaks, but does not interfere with next step: $^1$H NMR (400 MHz, CD$_2$Cl$_2$) δ 4.27 (t, J=5.9 Hz, 0.16), 3.62 (t, J=6.4 Hz, 0.15H), 2.39-2.36 (m, 0.14H).

Synthesis of (5-(3-chloropropoxy)-2-nitrophenyl)methanol b3

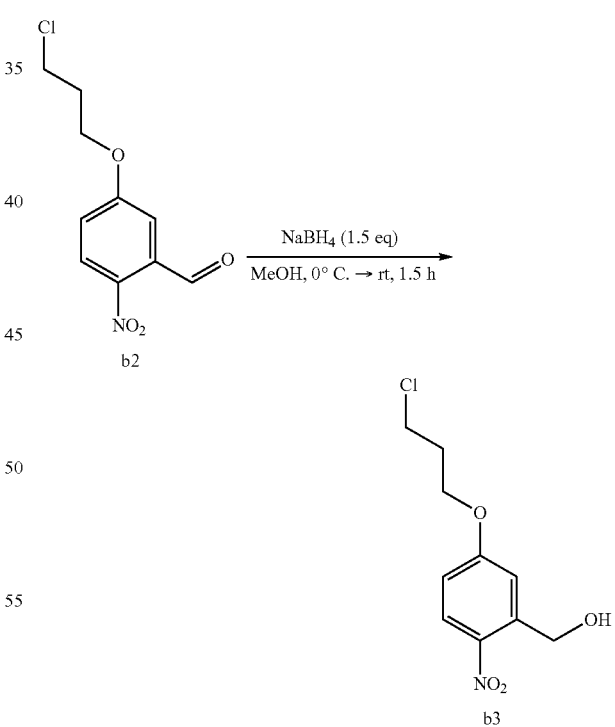

Sodium borohydride (133 mg, 0.00351 moles) was added to 5-(3-chloropropoxy)-2-nitrobenzaldehyde (570 mg, 0.00234 moles) in anhydrous methanol (12 mL) at 0° C. under nitrogen. The reaction was stirred for 1.5 hours and then concentrated with a rotary evaporator. The mixture was diluted with ethyl acetate (75 mL) and washed with 30 mL each of saturated sodium bicarbonate solution, water, and brine. The organic layer was dried with anhydrous magnesium sulfate, which was removed by filtration. The filtrate was concentrated, and the resulting residue was subject to silica gel chromatography using a gradient of 100% hexanes to 60% ethyl acetate in hexanes. The fractions containing the product were collected and volatiles were removed by rotary evaporation. The resulting residue was dried overnight to yield (5-(3-chloropropoxy)-2-nitrophenyl)methanol as a pale yellow solid (yield 69%*). $^1$H NMR (400 MHz, CD$_2$Cl$_2$) δ 8.16 (d, J=9.1 Hz, 1H), 7.27 (d, J=2.7 Hz, 1H), 6.92 (dd, J=9.1, 2.8 Hz, 1H), 4.98 (s, 2H), 4.24 (t, J=5.9 Hz, 2H), 3.77 (t, J=6.3 Hz, 2H), 2.28 (p**, J=6.1 Hz, 2H). $^{13}$C-NMR (100 MHz, CD$_2$Cl$_2$) δ 163.99, 141.21, 128.42, 114.95, 113.90, 65.80, 63.24, 41.91, 32.52 HRMS m/z: calculated for C$_{10}$H$_{12}$ClNO$_4$ [M+H]$^+$, 246.0528; found, 246.0529.

*Observed extra NMR peaks, but does not interfere with next step: $^1$H NMR (400 MHz, Methylene Chloride-d2) δ 3.63 (t, J=6.3 Hz, 0.14H), 2.39-2.31 (m, 0.24H). ** Pseudo pentet.

Synthesis of (5-(3-azidopropoxy)-2-nitrophenyl)methanol b4

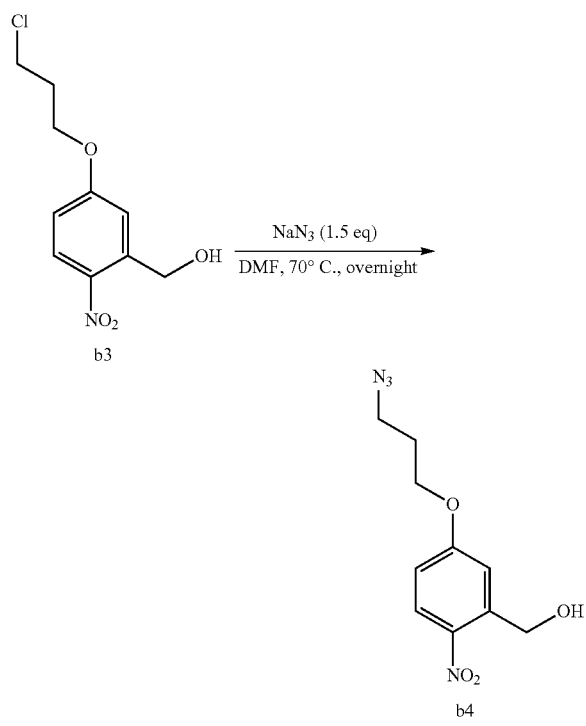

DMF (7.5 mL) was added to (5-(3-chloropropoxy)-2-nitrophenyl)methanol (635 mg, 0.00258 moles) and sodium azide (252 mg, 0.00387 moles) in a flask, and the resulting mixture was heated to 70° C., and stirred overnight. The reaction was diluted in ethyl acetate (100 mL) and washed twice with water (75 mL each) and once with brine (75 mL). The organic layer was dried with anhydrous magnesium sulfate, which was filtered out. The filtrate was concentrated on a rotary evaporator and dried in vacuo overnight to yield (5-(3-azidopropoxy)-2-nitrophenyl)methanol as a yellow solid (yield 88%). $^1$H NMR (400 MHz, CD$_2$Cl$_2$) δ 8.16 (d, J=9.1 Hz, 1H), 7.27 (d, J=2.8 Hz, 1H), 6.91 (dd, J=9.1, 2.8 Hz, 1H), 4.98 (s, 2H), 4.18 (t, J=6.0 Hz, 2H), 3.53 (t, J=6.6 Hz, 2H), 2.12-2.06 (m, 2H). $^{13}$C-NMR (100 MHz, CD$_2$Cl$_2$) δ 163.99, 141.22, 128.43, 114.97, 113.93, 66.15, 63.26, 48.68, 29.13 HRMS m/z: calculated for C$_{10}$H$_{12}$N$_4$O$_4$ [M+H]$^+$, 253.0931; found, 253.0939.

Synthesis of Compound b5

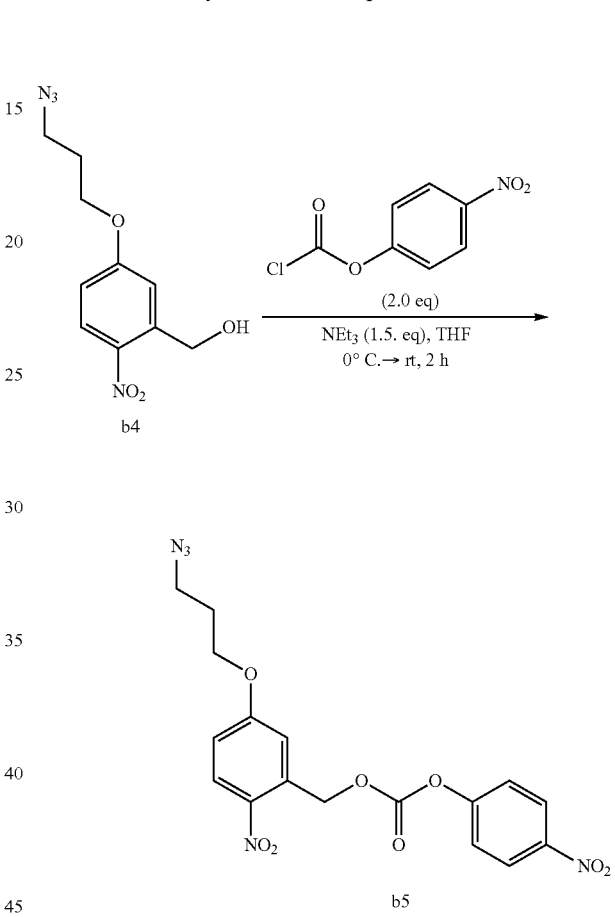

A previously reported reaction (Johnson, J. A.; Lu, Y. Y.; Burts, A. O.; Xia, Y.; Durrell, A. C.; Tirrell, D. A.; Grubbs. R. H. *Macromolecules* 2010, 43, 10326) was modified. A solution of (5-(3-azidopropoxy)-2-nitrophenyl)methanol (250 mg, 0.00099 moles) and triethylamine (0.21 mL, 0.0015 moles) in tetrahydrofuran (5 mL) was added dropwise to a flask containing 4-nitrophenyl chloroformate (423 mg, 0.0021 moles) in tetrahydrofuran (15 mL) at 0° C. under nitrogen. The ice-bath was removed, and the reaction was left to stir for one hour. The mixture was concentrated on a rotary evaporator and purified by silica gel chromatography eluted with a gradient from 100% hexanes to 100% ethyl acetate. The fractions containing the product was concentrated on a rotary evaporator and dried in vacuo overnight to yield b5 as a yellow solid (yield 65%*). $^1$H NMR (400 MHz, CD$_2$Cl$_2$) δ 8.31-8.25 (m, 2H), 8.23 (d, J=9.2 Hz, 1H), 7.49-7.40 (m, 2H), 7.20 (d, J=2.7 Hz, 1H), 6.99 (dd, J=9.2, 2.8 Hz, 1H), 5.72 (s, 2H), 4.19 (t, J=6.0 Hz, 2H), 3.55 (t, J=6.5 Hz, 2H), 2.16-2.05 (m, 2H). *Observed impurity peaks, but does not interfere with next step: $^1$H NMR (400 MHz, CD$_2$Cl$_2$) δ 8.12-8.08 (m), 6.92-6.88 (m). $^{13}$C-NMR (100 MHz, CD$_2$Cl$_2$) δ 163.88, 156.02, 152.65, 146.13, 140.66, 134.37, 128.73, 126.5, 125.81, 122.35, 116.1, 115.11, 114.15, 68.12, 66.33, 48.58, 29.02 HRMS m/z: calculated for C$_{17}$H$_{15}$N$_5$O$_8$[M+NH$_4$]$^+$. 435.1259; found, 435.1251.

Synthesis of Compound DOX-N$_3$

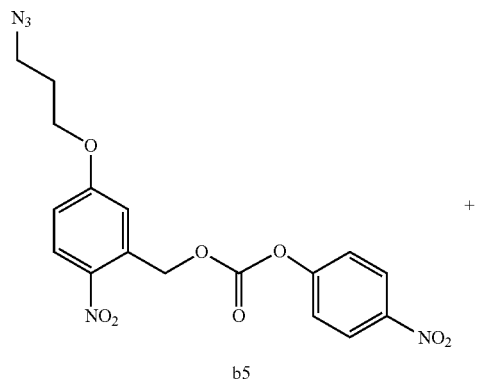

b5

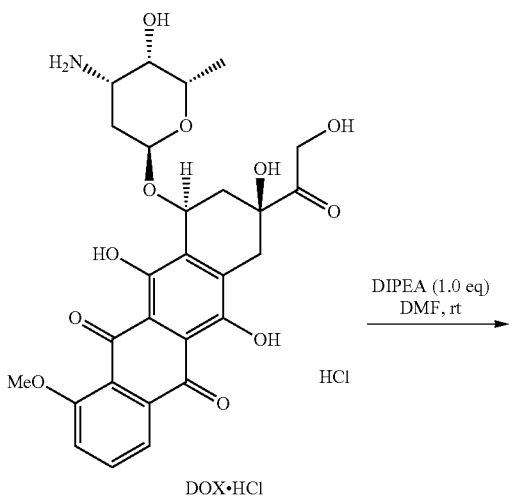

DOX·HCl

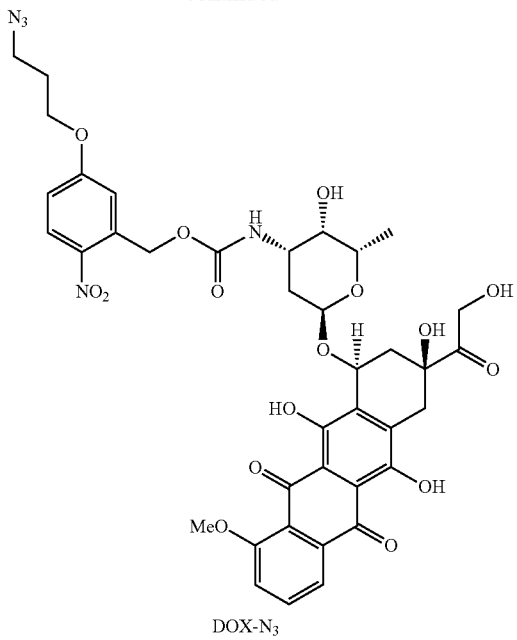

DOX-N$_3$

Doxorubicin hydrochloride (70.6 mg, 0.000122 moles) was dissolved DMF (1.5 mL), followed by addition of N,N-diisopropylethylamine (DIPEA) (0.021 mL, 0.000122 moles) and b5 (48 mg, 0.000116 moles). The solution was stirred at room temperature overnight, diluted with ethyl acetate (75 mL), and washed twice with water (50 mL each) and brine (50 mL). The organic layer was dried with anhydrous magnesium sulfate, which was removed by filtration. The filtrate was concentrated, and the residue was subject to silica gel chromatography using a gradient of 100% dichloromethane to 10% methanol in dichloromethane. The fractions containing the product were collected, and volatiles were removed by rotary evaporation. The resulting residue was dried overnight to yield DOX-N$_3$ as a red solid (yield 92%*). $^1$H NMR (400 MHz, CD$_2$Cl$_2$) δ 13.94 (s, 1H), 13.10 (s, 1H), 8.09 (d, J=9.1 Hz, 1H), 7.91 (dd, J=7.7, 1.1 Hz, 2H), 7.74 (t, J=8.1 Hz, 1H), 7.35 (dd, J=8.5, 1.1 Hz, 1H), 7.03-6.97 (m, 1H), 6.86-6.81 (m, 1H), 5.54 (d, J=8.6 Hz, 1H), 5.51-5.47 (m, 1H), 5.40 (dd, 24.6, 15.7, 1H), 5.24-5.19 (m, 1H), 4.74 (s, 2H), 4.60 (s, 1H), 4.19-4.11 (m, 1H), 4.09 (t, J=6.0 Hz, 2H) 3.99 (s, 3H), 3.89-3.82 (m, 1H), 3.68 (s, 1H), 3.48 (t, J=6.5 Hz, 2H), 3.22-3.12 (m, 1H), 2.94-2.87 (m, 1H), 2.50 (s, 1H), 2.34 (d, J=14.7 Hz, 1H), 2.13 (dd, J=14.6, 4.1 Hz, 1H), 2.02 (p**, J=6.3 Hz, 2H). 1.91-1.80 (m, 2H), 1.29 (d, J=6.5 Hz, 3H). $^{13}$C-NMR (100 MHz, CD$_2$Cl$_2$) δ 214.52, 187.20, 163.64, 161.60, 156.56, 155.90, 155.49, 140.54, 136.24, 135.77, 134.17, 133.96, 128.32, 120.00, 119.21, 114.20, 113.48, 112.02, 111.87, 101.11, 77.18, 69.96, 67.96, 66.08, 66.03, 63.99, 57.03, 48.57, 47.48, 36.09, 34.40, 30.61, 28.97, 17.15 HRMS m/z: calculated for C$_{38}$H$_{39}$N$_5$O$_{16}$ [M+Na]$^+$, 844.2284: found, 844.2271. *Observed DMF, but does not interfere with the next step: $^1$H NMR (400 MHz, CD$_2$Cl$_2$) δ 7.96 (s), 2.91 (s), 2.82 (s); $^{13}$C-NMR (100 MHz, CD$_2$Cl$_2$) δ 162.89, 36.79, 31.61. **Pseudo-pentet.

Synthesis of DOX-MM

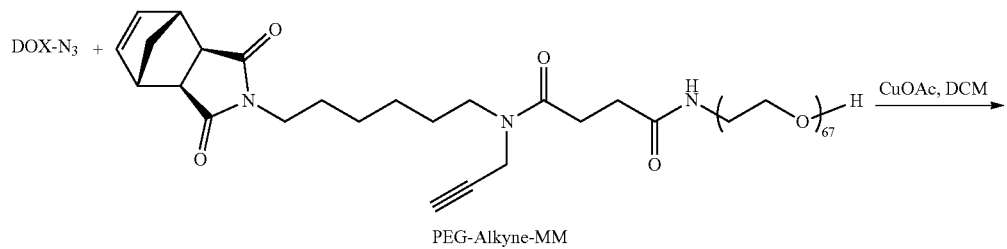

PEG-Alkyne-MM

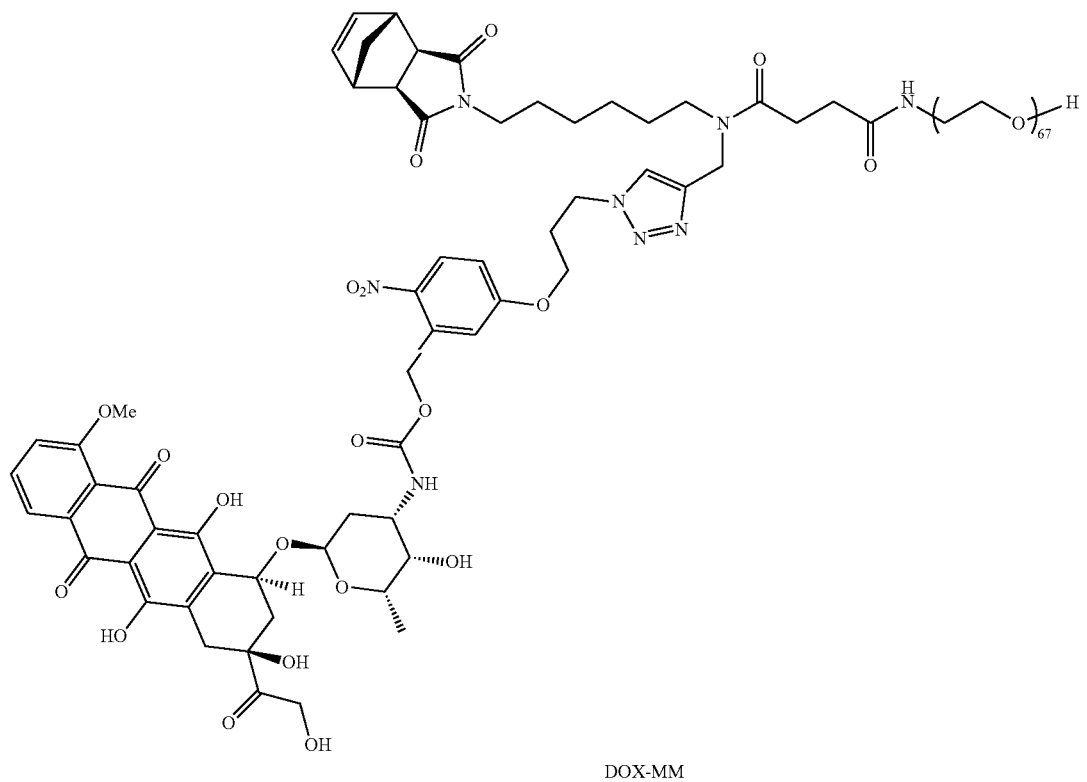

DOX-MM

Figure 25:
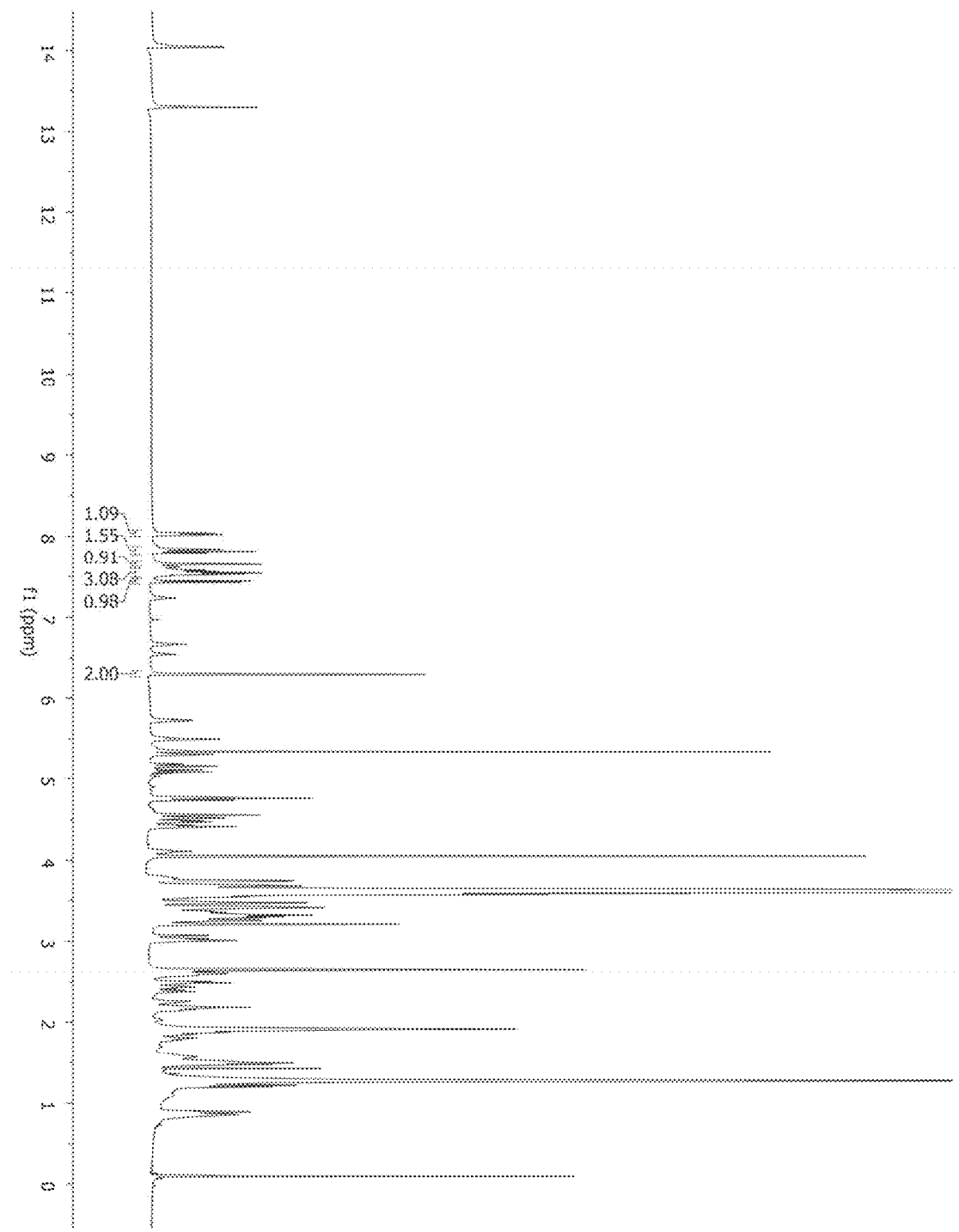
FIG. 25 shows an exemplary $^1$H NMR spectrum of DOX-MM in $CD_2Cl_2$.

To a solution of DOX-N$_3$ (49 mg, 0.060 mmol) and PEG-Alkyne-MM (300 mg. 0.060 mmol) in 10 ml DCM was added CuOAc (0.6 mg, 4.8 μmmol) under N$_2$. The reaction was allowed to stir at room temperature and monitored by LC-MS until the complete consumption of PEG-Alkyne-MM. Then the solvent was removed under vacuum, and the residue was purified by HPLC eluted with water (containing 0.1% acetic acid) and acetonitrile. The desired DOX-MM was obtained as light yellow powder (174 mg, 70% yield). HRMS (MALDI): m/z ((M+Li)$^+$ calculated for C$_{194}$H$_{336}$N$_8$O$_{87}$Li: 4177.23; observed: 4176.73; m/z (M+MeOH+H)$^+$ calculated for C$_{195}$H$_{341}$N$_8$O$_{88}$: 4203.25; Observed: 4201.77. An $^1$H NMR Spectrum is Shown in FIG. 25.

Example 3. Preparation of Macromonomer CPT-MM

Synthesis of c2

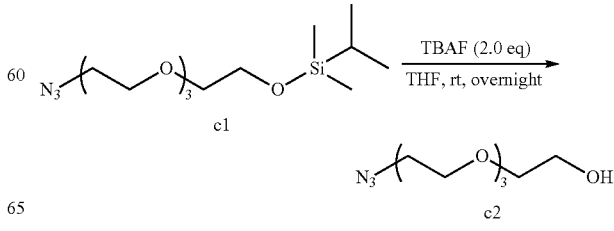

A THF (35 mL) solution of the silyl ether c1 (Zhou, H.; Woo, J.; Cok, A. M.; Wang, M.; Olsen, B. D.; Johnson, J. A. *Proc. Natl. Acad. Sci. USA* 2012) (3.5 g, 10.5 mmol) and tetra-n-butylammonium fluoride (TBAF) (5.5 g, 21 mmol) was allowed to stir under N2 at room temperature overnight. Then the reaction mixture was concentrated under vacuum, and the residue was purified by flash chromatography eluted with hexanes and ethyl acetate to give c2 (colorless oil, 2.3 g, 99% yield). The analytic data were comparable to previously reported data (Sanders, B. C.; Friscourt, F.; Ledin, P. A.; Mbua, N. E.; Arumugam, S.; Guo, J.; Boltje, T. J.; Popik, V. V.; Boons, G.-J. *J. Am. Chem. Soc.* 2010, 133, 949).

Synthesis of c3

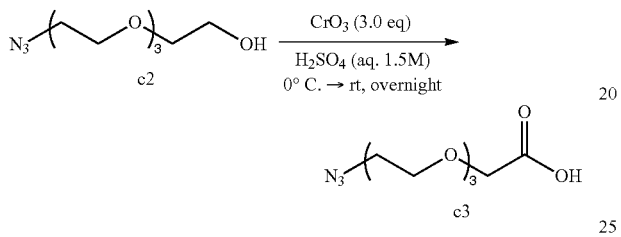

To a solution of c2 (1.1 g, 5.0 mmol) in acetone (55 mL) at 0° C. was added a solution of $CrO_3$ (1.5 g, 15 mmol) in 1.5 M $H_2SO_4$ in water (31 mL) dropwise by an additional funnel. After addition, the reaction was allowed to stir at room temperature overnight. The reaction was then quenched by addition of isopropanol (30 mL) and concentrated under vacuum. The aqueous residue was extracted by DCM (50 mL×4). The organic layers were combined, dried over Na2SO4, and concentrated under vacuum. The residue was purified by silica flash chromatography eluted with hexanes and ethyl acetate to give a colorless oil (1.2 g, 99% yield). The analytic data were comparable to previously reported data (Khiar, N.; Leal, M. P.; Baati, R.; Ruhlmann, C.; Mioskowski, C.; Schultz, P.; Fernandez. I. *Chem. Commun.* 2009, 4121).

Synthesis of CPT-N$_3$

The mixture of CPT (64 mg, 0.18 mmol), c3 (86 mg, 0.37 mmol), N-(3-dimethylaminopropyl)-N'-ethylcarbodiimide hydrochloride (EDC.HCl, 71 mg, 0.37 mmol), and 4-dimethylaminopyridine (DMAP, 45 mg, 0.37 mmol) in DCM (10 mL) was allowed to stir under $N_2$ at room temperature overnight. The reaction was then concentrated under vacuum, and the residue was purified by flash chromatography eluted with 5% MeOH in DCM to give yellow solid (81 mg, 78% yield). $^1$H NMR (400 MHz. Chloroform-d) δ 8.40 (s, 1H), 8.22 (d, J=8.4 Hz, 1H), 7.95 (d, J=8.0 Hz, 1H), 7.84 (dd, J=8.0, 6.9, 1H), 7.68 (dd, J=8.4, 6.9, 1H), 7.21 (s, 1H), 5.70 (d, J=17.2 Hz, 1H), 5.42 (d, J=17.2 Hz, 1H), 5.29 (s, 2H), 4.36 (d, J=5.5 Hz, 1H), 3.78-3.62 (m, 10H), 3.36 (t, J=7.5 Hz, 2H), 2.35-2.11 (m, 2H), 0.98 (t, J=7.5 Hz, 3H). $^{13}$C NMR (101 MHz, CDCl$_3$) δ 169.5, 167.1, 157.1, 152.1, 148.7, 146.3, 145.2, 131.1, 130.5, 129.4, 128.3, 128.1, 128.0, 127.9, 120.1, 95.7, 76.2, 70, 9, 70.5, 70.5, 70.4, 69.8, 68.0, 67.0, 50.5, 49.8, 31.6, 7.4. MS (ESI) m/z (M+Li)$^+$ calculated for C$_{28}$H$_{29}$N$_5$O$_8$Li: 564.2089; observed: 564.2098.

Synthesis of CPT-MM

-continued

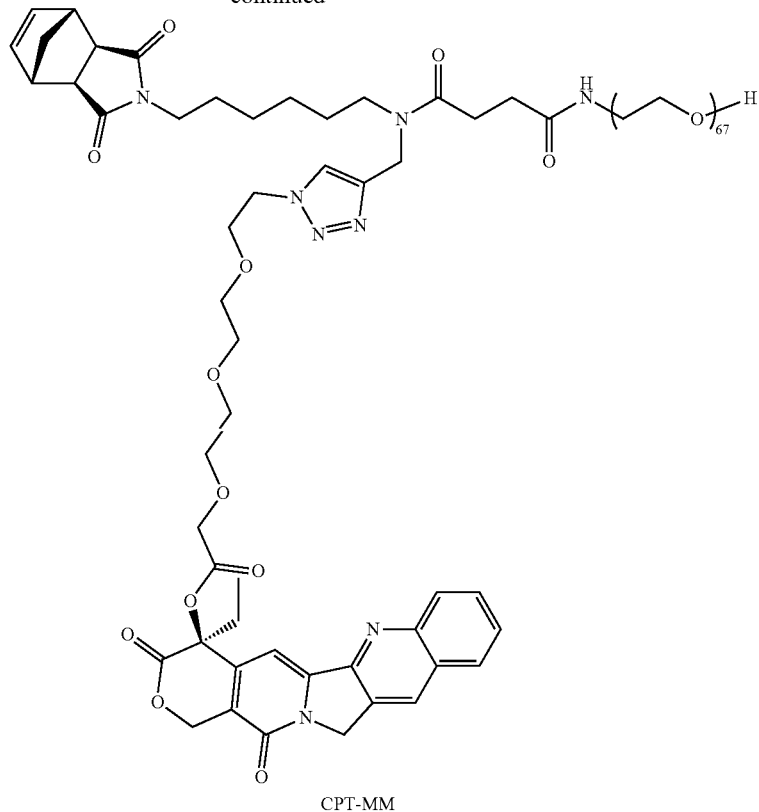

CPT-MM

Figure 26:
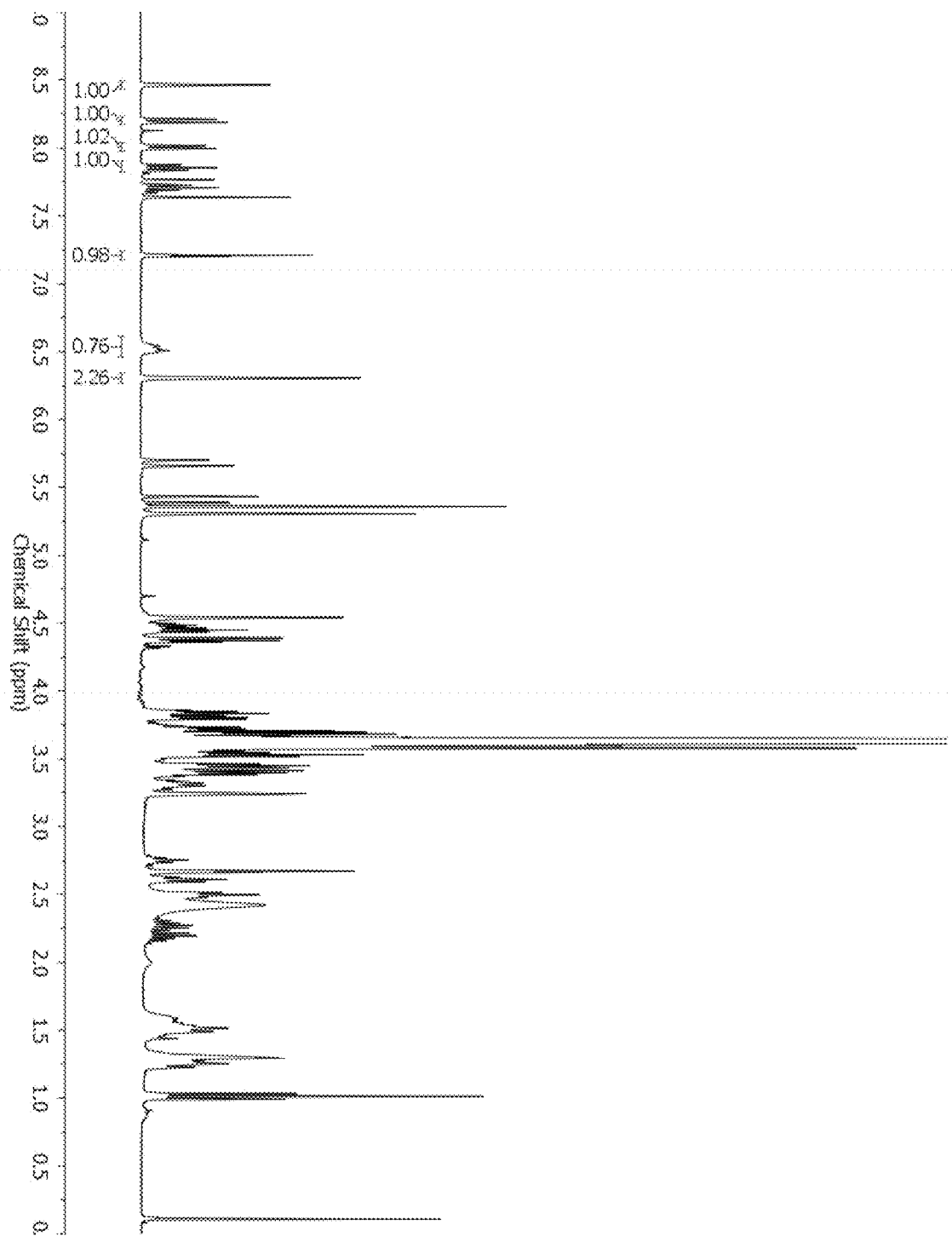
FIG. 26 shows an exemplary $^1$H NMR spectrum of CPT-MM in $CD_2Cl_2$.

To a solution of CPT-N$_3$ (50 mg, 0.089 mmol) and PEG-Alkyne-MM (300 mg. 0.089 mmol) in 10 ml DCM, was added CuOAc (0.6 mg, 4.8 μmmol) under N2. The reaction was allowed to stir at room temperature and monitored by LC-MS until the complete consumption of PEG-Alkyne-MM. Then the solvent was removed under vacuum and the residue was purified by HPLC eluted with water (containing 0.1% acetic acid) and acetonitrile. The desired CPT-MM was obtained as light yellow powder (140 mg, 40% yield). HRMS (MALDI) m/z ((M+H$_2$O+Li)$^+$ calculated for C$_{184}$H$_{328}$N$_8$O$_{80}$Li: 3939.52; observed: 3938.51; (M+Li)$^+$ calculated for C$_{184}$H$_{326}$N$_8$O$_{79}$Li: 3919.19; observed: 3919.69. An $^1$H NMR spectrum is shown in FIG. 26.

Example 4. Pt-BASP Formation Via ROMP

Pt-BASP syntheses were performed in a glovebox under an N$_2$ atmosphere though similar results may be expected under ambient conditions. The weight content of all the drugs (CPT, DOX, and cisplatin) included in a Pt-BASP (e.g., polymer P1, P2a, P2b, or P3) are 3.7% for polymer P1, 5.5% for polymer P2b, 6.5% for polymer P2a, and 8.2% for polymer P3, compared to the total weight of the Pt-BASP.

Synthesis of P1

Macromonomer (MM) 4 (PEG-MM) was added to a 4 mL vial containing a stir bar. N equivalents of XL3 were added to a separate 2 mL vial containing stir bars. DCM was added to the vial with MM 4 followed by a freshly prepared solution of catalyst C-1 (cat.) in DCM (2 mg cat./mL DCM, amount added to give desired MM 4:C-1 (m:1)) such that the total concentration of MM 4 was 0.05 M. After 10 minutes of stirring at 25° C., aliquots of the polymerization mixture were transferred to the vials containing XL3. The resulting mixtures were stirred at 25° C. for 6 hrs, at which point 1 drop of ethyl vinyl ether was added to quench the polymerization. The DCM and excess ethyl vinyl ether were removed under reduced pressure.

In one set of experiments, PEG-MM (70.0 mg) was added to a 4 mL vial containing a stir bar. XL3 (6.4 mg) was added to a separate 4 mL vial containing a stir bar. THF (273 μL) was added to the vial with PEG-MM followed by a freshly prepared solution of catalyst cat, in THF (0.02 mmol/mL, 152 μL) to give desired PEG-MM:cat. (mol:mol)=7. Note that the total concentration of PEG-MM was 0.05 M. After 20 minutes of stirring at 25° C., 406 μL of the polymerization mixture were transferred to the vial containing XL3. The resulting mixtures were stirred at 25° C. for 6 hrs, at which point 1 drop of ethyl vinyl ether was added to quench the polymerization. The THF and excess ethyl vinyl ether were removed under reduced pressure.

Synthesis of P2a

PEG-MM (48.4 mg) and CPT-MM (23.1 mg) were added to a 4 mL vial containing a stir bar. XL3 (6.4 mg) was added to a separate 4 mL vial containing a stir bar. THF (268 μL) was added to the vial with PEG-MM followed by a freshly prepared solution of catalyst cat, in THF (0.02 mmol/mL, 149 μL) to give desired PEG-MM:cat. (mol:mol)=7. Note that the total concentration of CPT-MM and PEG-MM was 0.05 M. After 20 minutes of stirring at 25° C., 406 μL of the polymerization mixture were transferred to the vial containing XL3. The resulting mixtures were stirred at 25° C. for 6 hrs, at which point 1 drop of ethyl vinyl ether was added to quench the polymerization. The THF and excess ethyl vinyl ether were removed under receded pressure.

Synthesis of P2b

PEG-MM (60.0 mg) and DOX-MM (9.7 mg) were added to a 4 mL vial containing a stir bar. XL3 (6.4 mg) was added to a separate 4 mL vial containing a stir bar. THF (265 µL) was added to the vial with PEG-MM followed by a freshly prepared solution of catalyst cat, in THF (0.02 mmol/mL, 147 µL) to give desired PEG-MM:cat. (mol:mol)=7. Note that the total concentration of DOX-MM and PEG-MM was 0.05 M. After 20 minutes of stirring at 25° C. 397 µL of the polymerization mixture were transferred to the vial containing XL3. The resulting mixtures were stirred at 25° C. for 6 hrs, at which point 1 drop of ethyl vinyl ether was added to quench the polymerization. The THF and excess ethyl vinyl ether were removed under reduced pressure.

Synthesis of P3

PEG-MM (38.8 mg), CPT-MM (22.3 mg), and DOX-MM (9.4 mg) were added to a 4 mL vial containing a stir bar. XL3 (6.4 mg) was added to a separate 4 mL vial containing a stir bar. THF (258 µL) was added to the vial with PEG-MM followed by a freshly prepared solution of catalyst cat, in THF (0.02 mmol/mL, 144 µL) to give desired PEG-MM:cat. (mol:mol)=7. Note that the total concentration of CPT-MM, DOX-MM, and PEG-MM was 0.05 M. After 20 minutes of stirring at 25° C., 382 µL of the polymerization mixture were transferred to the vial containing XL3. The resulting mixtures were stirred at 25° C. for 6 hrs, at which point 1 drop of ethyl vinyl ether was added to quench the polymerization. The THF and excess ethyl vinyl ether were removed under reduced pressure.

Example 5. Characterization of Polymers P1, P2a, P2b, and P3

Figure 16:
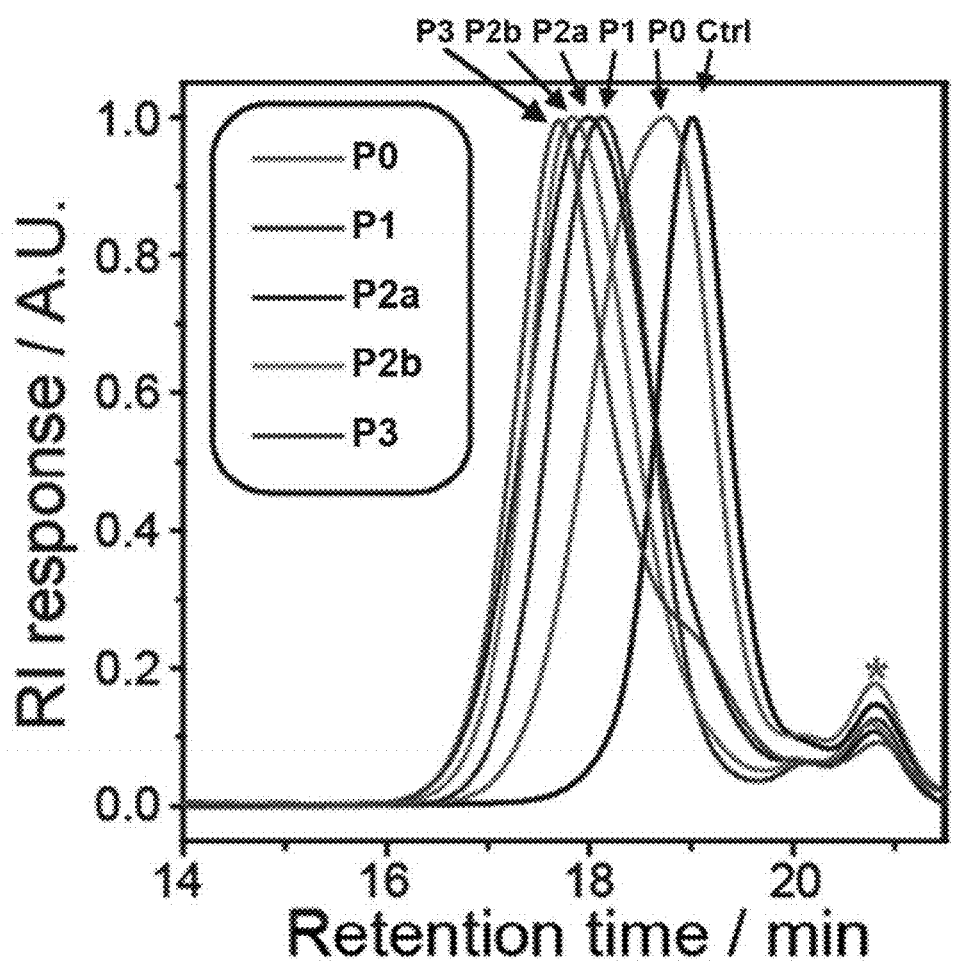
FIG. 16 shows exemplary gel permeation chromatography (GPC) traces of exemplary Pt-BASPs. P0 is a non-agent-loaded (e.g., non-drug-loaded) BASP, which is shown in FIG. 27. Ctrl is a parent brush polymer with no crosslinker (e.g., XL3) added and is not a BASP. Residual macromonomer is indicated with a star.

Upon completion of the brush-first ROMP reactions, the crude reaction mixtures were analyzed by gel permeation chromatography (FIG. 16). In all cases, the conversion of MM to Pt-BASP was >90%.

Figure 17:
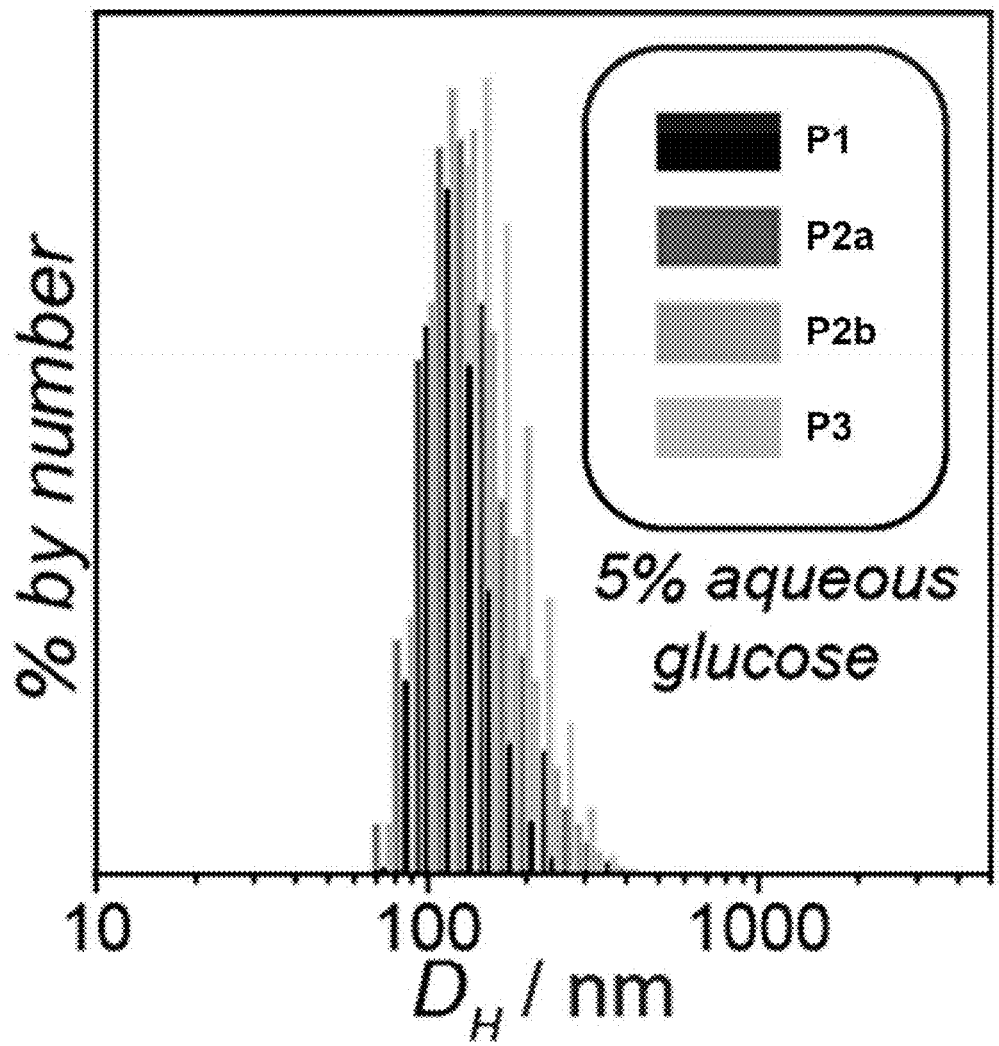
FIG. 17 shows exemplary dynamic light scattering (DLS) histograms for polymers P1, P2a, P2b, and P3.

Dynamic light scattering (DLS) revealed hydrodynamic diameters ($D_H$) from 122-191 nm for the Pt-BASPs (Table 2 and FIG. 17). These values are suitable for passive tumor targeting via the EPR effect (Matsumura, Y.; Maeda. H. *Cancer Res.* 1986, 46, 6387): they are larger than the ca. 6-8 nm renal clearance threshold (Petros, R. A.; DeSimone, J. M. *Nat. Rev. Drug Discovery* 2010, 9, 615) and smaller than the 200-250 nm splenic clearance cutoff (Moghimi, S. M.; Hunter, A. C.; Murray, J. C. *Pharmacological Reviews* 2001, 53, 283).

Figure 18:
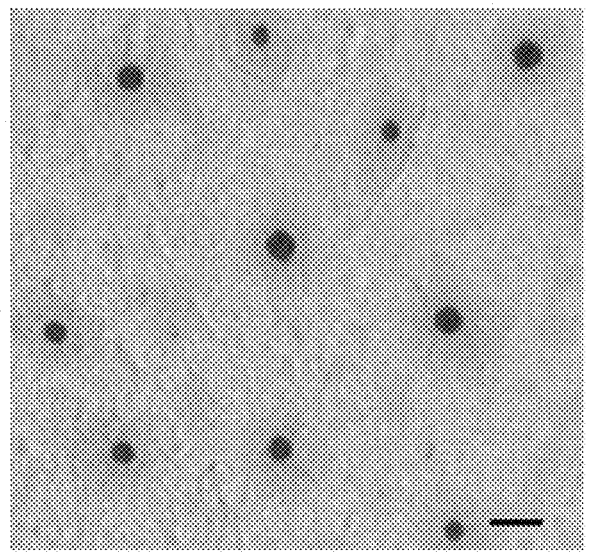
FIG. 18 shows exemplary transmission electron microscopy (TEM) images of polymer P3. Scale bar corresponds to 100 nm.
Figure 19:
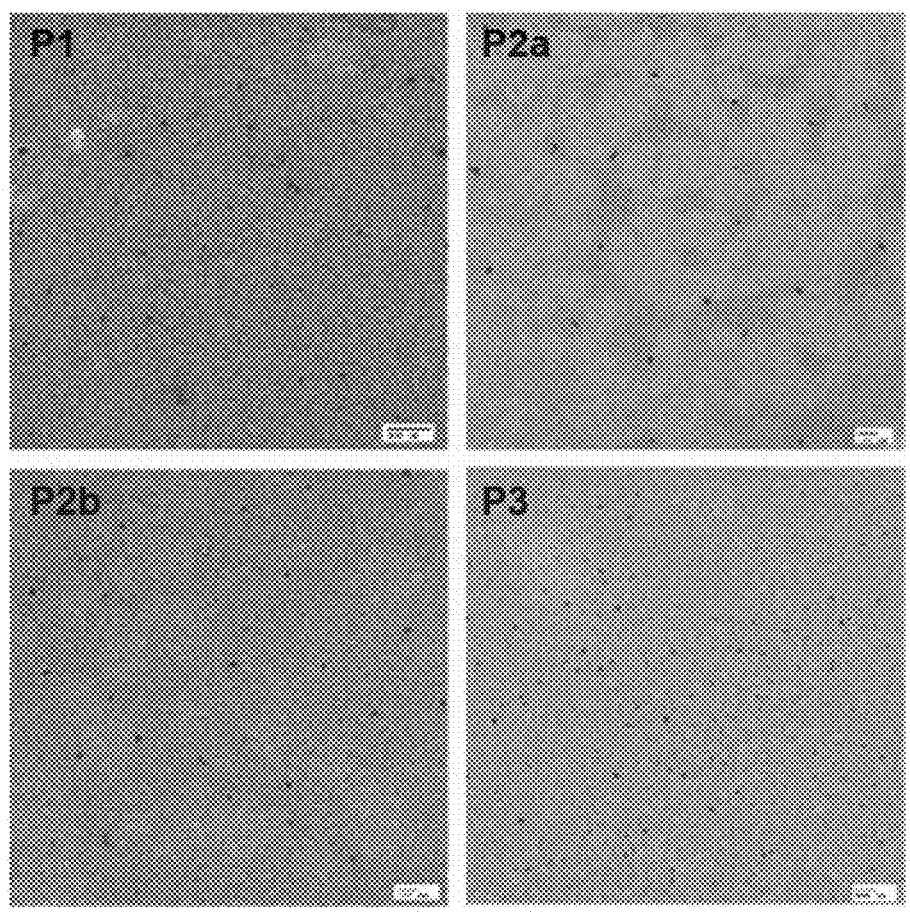
FIG. 19 shows exemplary TEM images of the unstained Pt-BASPs in the dry state (cast from aqueous solution).
Figure 20:
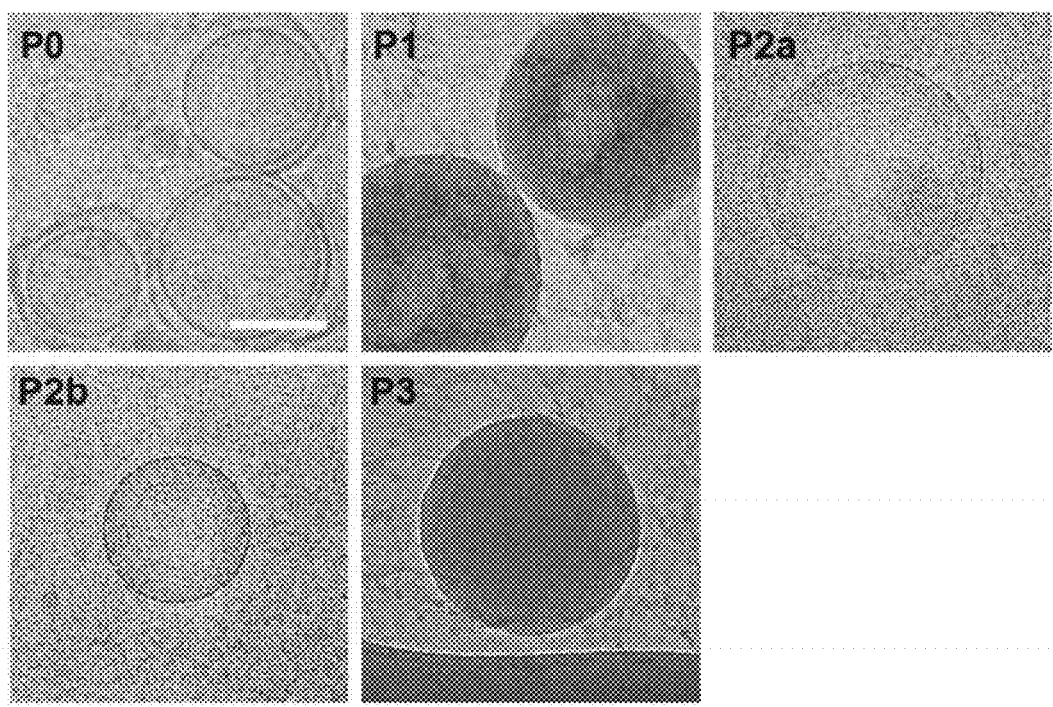
FIG. 20 shows exemplary Cryo TEM images of polymers P1, P2a, P2b, and P3 in aqueous solution. P0: non-drug loaded BASP (FIG. 27). The scale bar is 100 nm.

Transmission electron microscopy (TEM) images of unstained Pt-BASPs showed concentric dark and light regions (FIGS. 18 and 19). These results can be attributed to the dense cisplatin core and PEG corona, respectively. The average diameters of the Pt-BASP as measured by TEM ($D_{TEM}$) in the dry state are provided in Table 2. CryoTEM images of the Pt-BASPs in aqueous solution (FIG. 20) show particle diameters that agree well with the DLS data.

TABLE 2

Exemplary characterization data of exemplary Pt-BASPs: polymers P1, P2a, P2b, and P3

| sample name | drug combination | equiv. PEG-MM | equiv. XL3 | equiv. CPT-MM | equiv. DOX-MM | $D_{TEM}{}^a$/ nm | $D_H{}^b$/ nm |
|---|---|---|---|---|---|---|---|
| P1 | cisplatin only | 7.00 | 3.00 | 0 | 0 | 125(15) | 122(7) |
| P2a | cisplatin & CPT | 4.93 | 3.00 | 2.07 | 0 | 114(20) | 178(6) |
| P2b | cisplatin & DOX | 6.17 | 3.00 | 0 | 0.831 | 110(19) | 191(7) |
| P3 | cisplatin & CPT & DOX | 4.09 | 3.00 | 2.07 | 0.831 | 103(21) | 180(10) |

Diameters as measured by transmission electron microscopy (TEM. $D_{TEM}$) and dynamic light scattering (DLS, $D_H$). [a]TEM data were obtained from dilute aqueous solutions cast onto a TEM grid, dried, and imaged without staining. Particle sizes were measured using IMAGEJ software. Values in parentheses correspond to the standard deviation for at least ten particles. [b]$D_H$ values were measure using 0.1 mg Pt-BASP/mL 5% glucose solutions. DLS correlation functions were fit using the CONTIN algorithm. Values in parentheses correspond to the standard deviation for three particle measurements.

TABLE 3

Exemplary characterization data of exemplary Pt-BASPs: polymers P1, P2a, P2b, and P3

| Sample | $M_w$/kDa[a] | Đ[b] | % P1[c] | % DOX[d] | % CPT[e] |
|---|---|---|---|---|---|
| P1 | 142 | 1.2 | 3.7 | NA | NA |
| P2a | 182 | 1.4 | 3.6 | NA | 2.9 |
| P2b | 103 | 1.7 | 3.7 | 1.8 | NA |
| P3 | 144 | 1.5 | 3.6 | 1.8 | 2.8 |

[a]Weight-average molecular weight ($M_w$) from GPC-MALLS.
[b]Dispersity index ($M_w/M_n$).
[c]Percent cisplatin by weight.
[d]Percent DOX by weight.
[e]Percent CPT by weight.

Example 6. In Vitro Platinum Release

In phosphate buffered saline (PBS).

Drug release from Pt-BASPs was investigated using the dialysis method. The Pt-BASP sample m5N5 was dispersed in PBS with particle concentration of 5 mg/mL. A 1 mL aliquot of the particle dispersion was transferred into a dialysis membrane tubing with molecular weight cutoff of 10000 Da and dialyzed against 99 mL of PBS in a 37° C. water bath at a shaking speed of 80 rpm. At predetermined time points, aliquots of 5 mL were taken and added 150 µL 70% $HNO_3$ for the determination of platinum content by inductively coupled plasma atomic emission spectroscopy (ICP-AES) analysis.

In phosphate buffered saline (PBS) containing glutathione (GSH).

The same procedure was performed as in PBS except that a solution of GSH in PBS (10 mM) was used instead of PBS.

Example 7. In Vitro Cellular Cytotoxicity Assays

Cell Culture.

Human Hela cell line was cultured at 37° C. under a humidified atmosphere of 5% CO2. The cells were grown in the final medium (FMEM) consist of 89% Eagle's minimum essential medium (EMEM, ATCC, 30-2003), 10% fetal bovine serum (Gibco, 10437028) and 1% antibiotics (100 U/mL penicillin and 100 µg/mL streptomycin, Gibco. 105140122). The cells were continuously maintained in the culture medium and subcultured every 3-4 days.

Drug Treatment and Cell Viability Assay.

Hela cells were seeded at 10.000 cells/well in a 96-well plate and allowed to attach for 20 h before drug treatment. Prior to drug exposure, the culture medium was removed. Then, fresh media with drug concentrations ranging from 0 to 400 µM (based on dry weight of polymer dissolved in FMEM) were added to the appropriate wells. The cells were subsequently incubated in a cell culture incubator for 48 h. The medium was removed before fresh drug-free medium was added to each well. The cells were incubated for another 24 h before analysis by the MTT cell proliferation assay (ATCC, 30-1010K). Cells were incubated with fresh medium containing MTT reagent for 4 h at 37° C. DMSO was added to solubilize the purple formazan crystals formed by proliferating cells. Absorbance at 550 nm was measured on a Safire II (Tecan) plate reader. Data were fit to a sigmoidal function to determine the half-maximum inhibitory concentration (IC50).

Results.

Figure 21A:
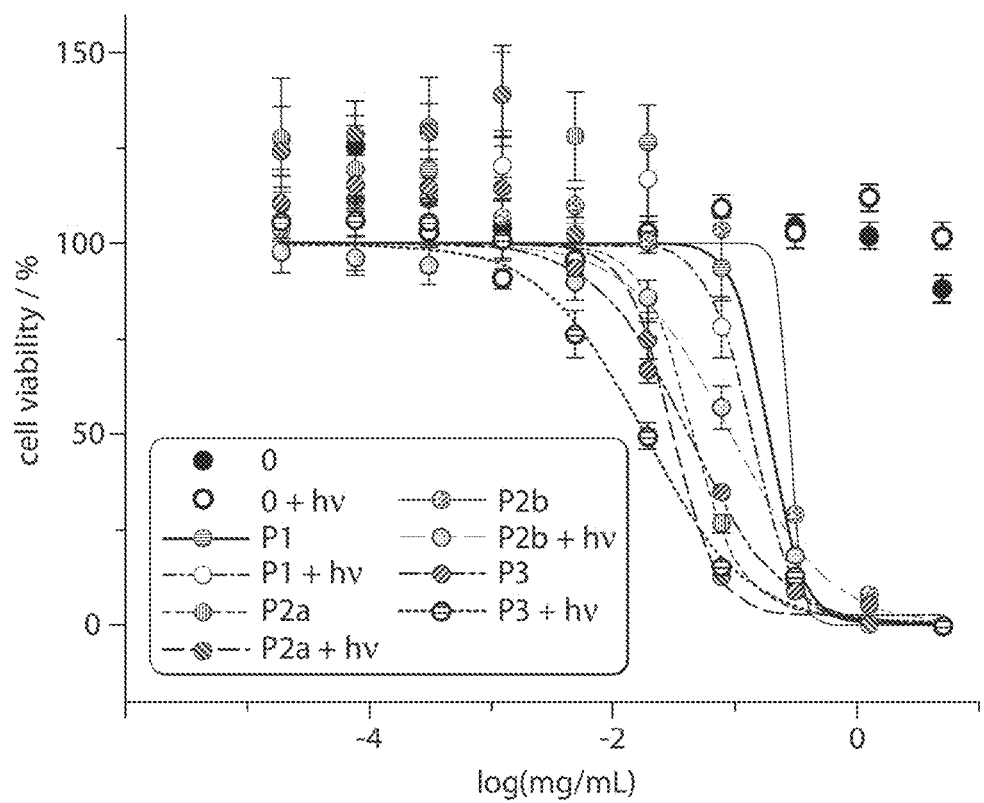
FIG. 21A shows exemplary OVCAR3 cell viability data after 72 h of treatment with 5% glucose (0) and polymers P1, P2a, P2b, and P3. Data labeled "+hv" were obtained from cells treated with polymer P1, P2a, P2b, or P3, irradiated with 365 nm light for 10 min, and then incubated for a total of 72 h. Solid and dashed lines represent sigmoidal fits for dark and irradiated samples, respectively.
Figure 21B:
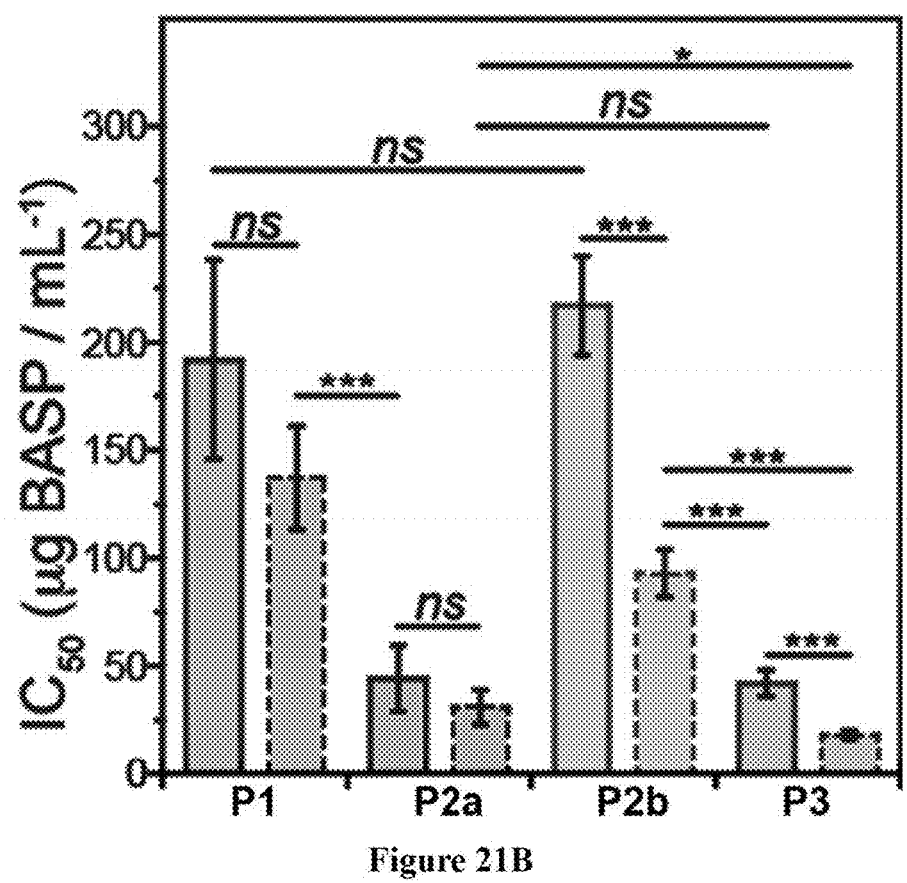
FIG. 21B is a bar chart showing exemplary $IC_{50}$ values of polymers P1, P2a, P2b, and P3 along with statistical comparisons. Error represents SEM of four technical replicates.
Figure 22:
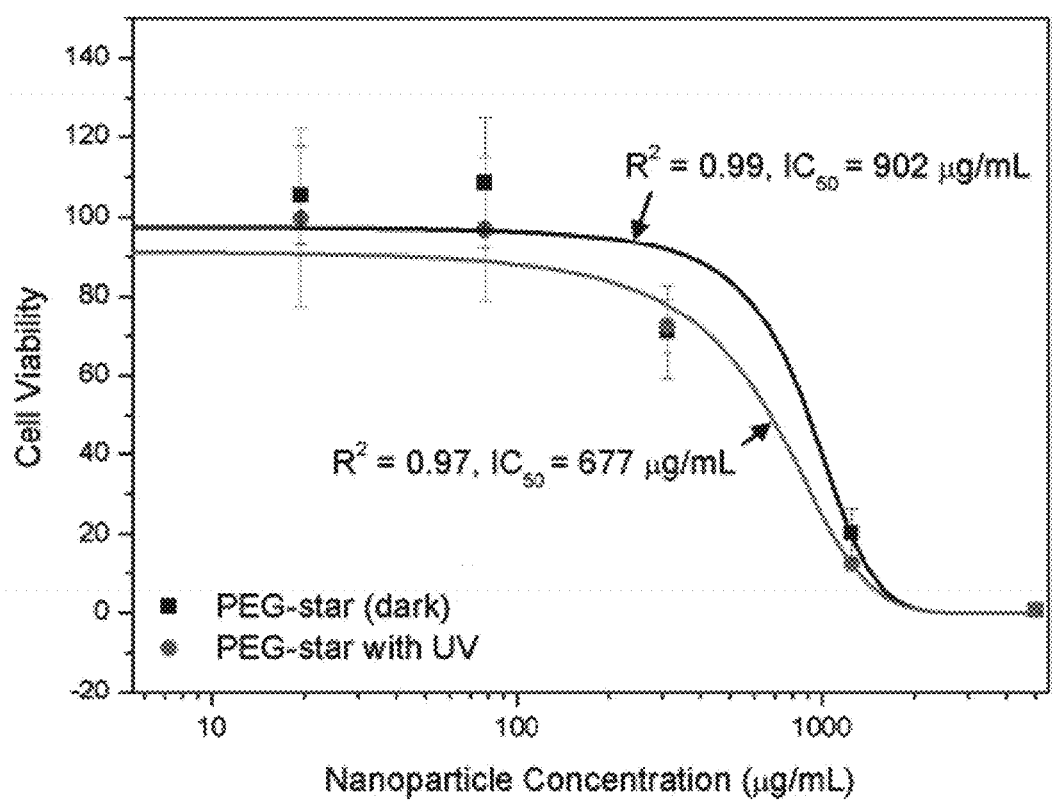
FIG. 22 shows exemplary OVCAR3 cell viability data after 72 h of treatment with P0, a non-agent-loaded BASP (FIG. 27).
Figure 27:
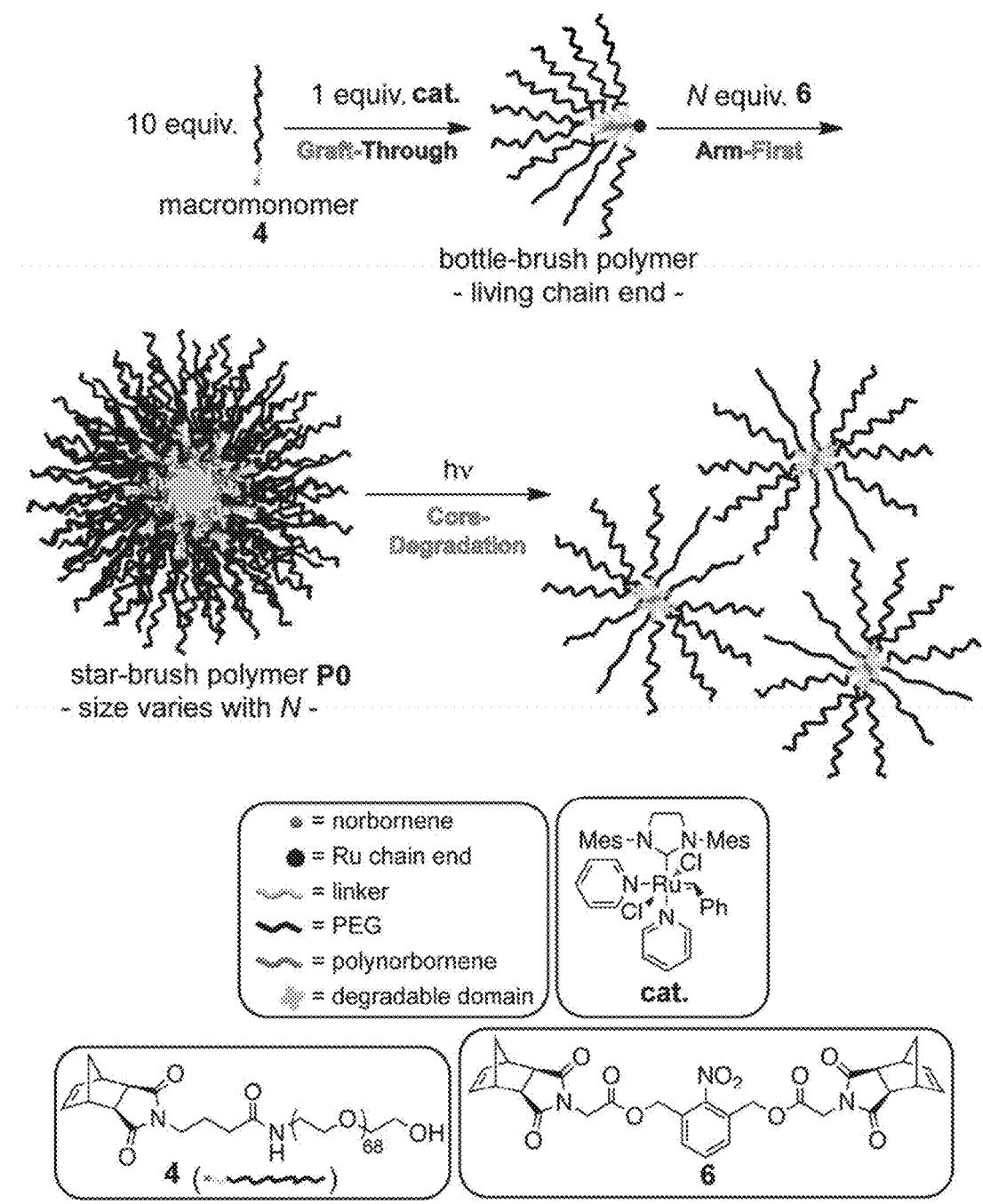
FIG. 27 shows the chemical structure of P0, a non-agent-loaded BASP.

Exemplary results of the cytotoxicity of polymers P1, P2a, P2b, and P3 using OVCAR3 human ovarian cancer cells are shown in FIG. 21A. OVCAR3 is an established model cell line derived from a patient with platinum-refractory (Godwin, A. K.; Meister, A.; Odwyer, P. J.; Huang, C. S.; Hamilton, T. C.; Anderson. M. E. *Proc. Natl. Acad. Sci. U.S.A* 1992, 89, 3070) disease that exhibits genotypic similarity with the high-grade serous subtype (Domcke, S.; Sinha, R.; Levine. D. A.; Sander, C.; Schultz, N. *Nature Communications* 2013, 4, 2126). Given the widespread clinical use of anthracyclines and topoisomerase I inhibitors in second-line therapies for recurrent ovarian carcinoma, OVCAR3 is a suitable model for BASP combination chemotherapy (Huinink, W. T. B.; Gore, M.; Carmichael, J.; Gordon, A.; Malfetano, J.; Hudson. I.; Broom, C.; Scarabelli, C.; Davidson. N.; Spanczynski, M.; Bolis, G.; Malmstrom, H.; Coleman, R.; Fields, S. C.; Heron, J. F. *Journal of Clinical Oncology* 1997, 15, 2183; Yap, T. A.; Carden, C. P.; Kaye, S. B. *Nat. Rev. Cancer* 2009, 9, 167). Exposure of OVCAR3 cells to 365 nm UV light for 10 min (0+hv) induced no observable toxicity. A non-agent-loaded BASP. P0 (FIG. 27; Liu, J.; Burts, A. O.; Li, Y.; Zhukhovitskiy. A. V.; Ottaviani, M. F.; Turro, N. J.; Johnson. J. A. *J. Am. Chem. Soc.* 2012, 134, 16337), displayed toxicity only at very high concentrations (>650 µg/mL) in the presence and absence of UV light (FIG. 22). Amongst the agent-loaded (e.g., drug-loaded) Pt-BASPs, polymer P1 had the largest $IC_{50}$ value: 192±46 µg/mL, 23±5 µM (FIG. 21A).

Polymer P2a showed a much lower $IC_{50}$: 44±15 µg/mL, 8±2 µM (FIG. 21A). Polymer P2b had an $IC_{50}$ of 217±23 µg/mL (32±3 µM) in the absence of irradiation, which is not significantly different from polymer P1; exposure to UV for 20 min led to a 2.3±0.3-fold decreased $IC_{50}$ to 93±11 g/mL (14±1 µM) (FIG. 21A). No significant decrease in viability was observed following photo-exposure of polymers P1 and P2a (P=0.078 and 0.018, respectively). These results suggest that therapeutically active cisplatin and CPT are released from these Pt-BASPs without an external trigger; DOX release is only significant upon irradiation.

When cells were treated with polymer P3 without UV irradiation, the $IC_{50}$ was 42±6 g/mL (9.2±0.8 µM) (FIG. 21A). This result can be rationalized via extrapolation of the results for polymers P1, P2a, and P2b: in the absence of light, polymer P3 only released CPT and cisplatin, i.e., it behaved similarly to P2a (P=0.81). After UV irradiation for 10 min, the $IC_{50}$ for P3 dropped 2.3±0.4-fold to 18±2 g/mL (4.0±0.3 LM total drug); the 3-drug-loaded Pt-BASP (e.g., polymer P3) outperformed the 1- and 2-drug loaded Pt-BASPs (e.g., polymers P1, P2a, and P2b).

Example 8. Cellular Internalization Assays

Figure 23:
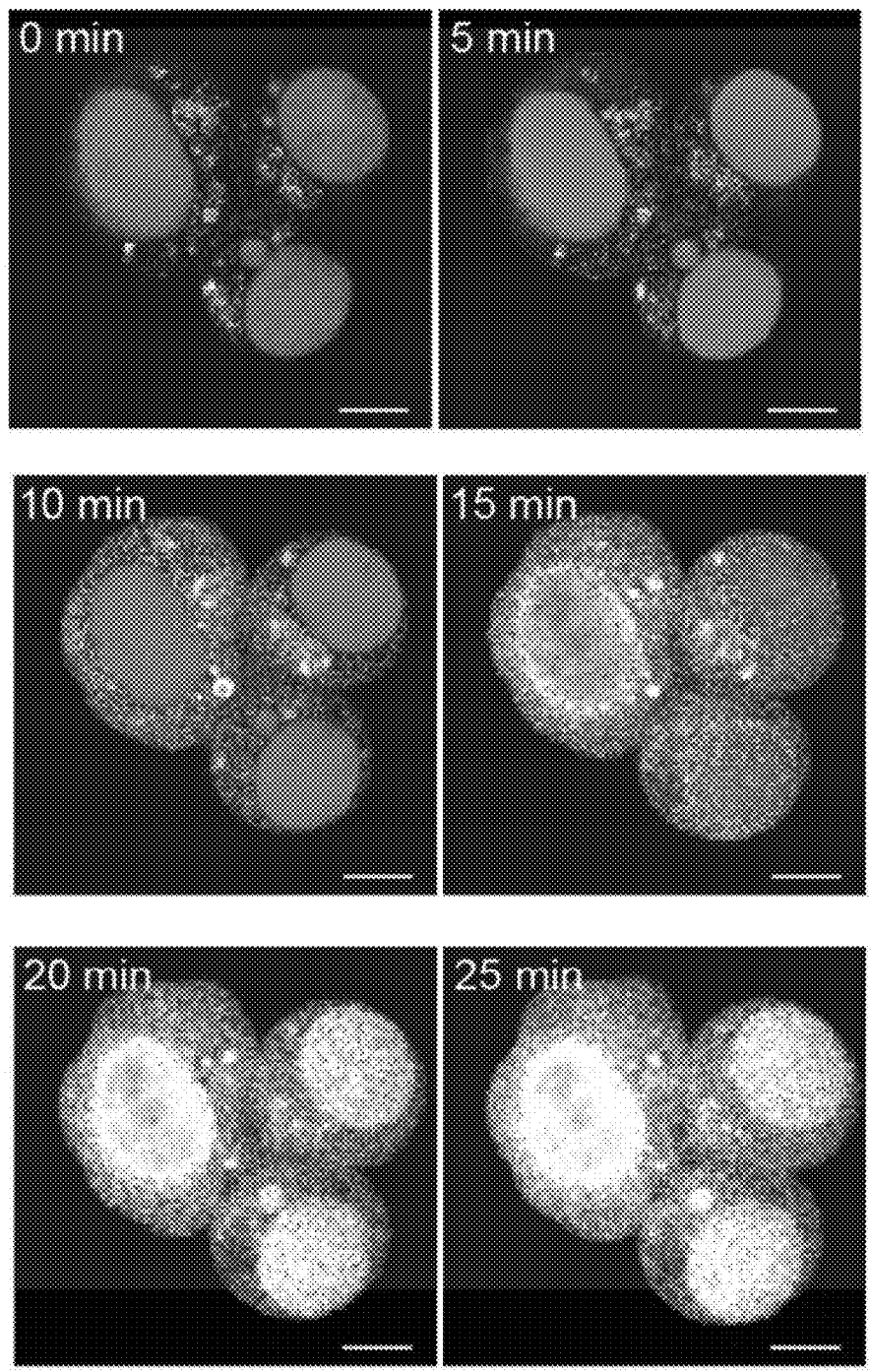
FIG. 23 shows exemplary photo-triggered release of DOX in OVCAR3 cells as monitored by live-cell confocal fluorescence imaging. Cells were loaded with polymer P2b for 30 min and concurrently exposed to 405 nm UV irradiation during imaging of doxorubicin (red or light grey; $\lambda_{ex}/\lambda_{em}$=561/595 nm) and nuclei (acridine orange, green or dark grey; $\lambda_{ex}/\lambda_{em}$=488/525 nm). Scale bar is 5 µm.
Figure 24:
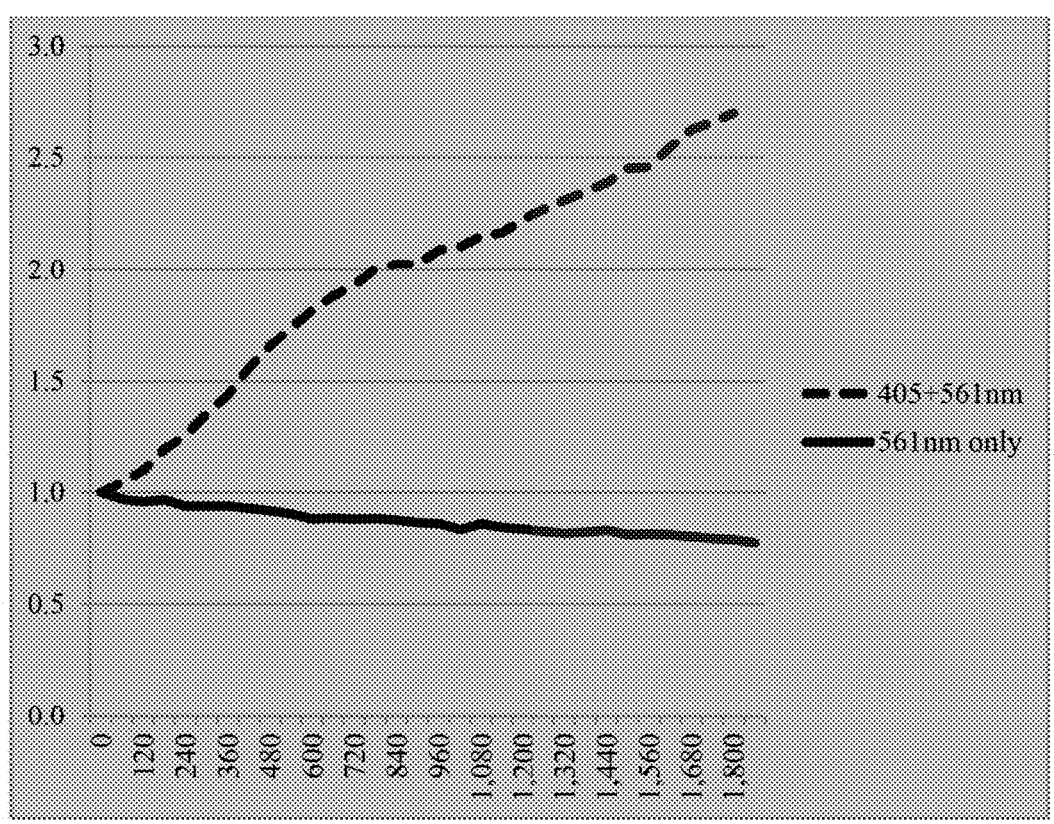
FIG. 24 shows the mean DOX fluorescence intensity (fold versus time 0) of polymer P2b as a function of irradiation time (seconds).

To examine cellular internalization of Pt-BASPs, a series of confocal fluorescence imaging experiments were conducted on live OCVAR3 cells using the inherent fluorescence of DOX. After 30 min of incubation with polymer P2b in the dark, cells were briefly irradiated with 405 nm laser light once per minute and imaged immediately afterwards for 25 min (DOX $\lambda_{ex}/\lambda_{em}$=561/595 nm). FIG. 23 shows images collected at various times. Initially, punctate, extra-nuclear DOX fluorescence was observed to co-localize with acridine orange in the end/lysosomes (FIG. 23, 0 min); photo-induced DOX release lead to rapid re-distribution of fluorescence throughout the cytoplasm and nucleus and a 2.7-fold fluorescence intensity increase (FIG. 23, 25 min; FIG. 24).

To ensure that these results were due to DOX release, a control experiment was conducted wherein cells were pulsed with 561 nm light rather than 405 nm. In this case, the particles remain trapped in the endosomes, and no increase in mean fluorescence intensity was observed.

EQUIVALENTS AND SCOPE

In the claims articles such as "a." "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A platinum complex of Formula (I):

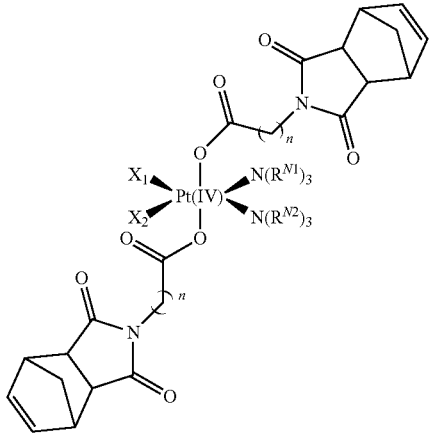

or a salt thereof,
wherein:
  $X_1$ is F, Cl, Br, or I;
  $X_2$ is F, Cl, Br, or I;
  each instance of $R^{N1}$ and $R^{N2}$ is independently hydrogen, optionally substituted $C_{1-6}$ alkyl, or a nitrogen protecting group; or two $R^{N1}$ are taken with the intervening atoms to form an optionally substituted heterocyclic ring; or two $R^{N2}$ are taken with the intervening atoms to form an optionally substituted heterocyclic ring; or $R^{N1}$ and $R^{N2}$ are taken with the intervening atoms to form an optionally substituted heterocyclic ring; and
  n is 1, 2, 3, 4, 5, or 6.

2. The platinum complex of claim 1, wherein the complex is of Formula (II):

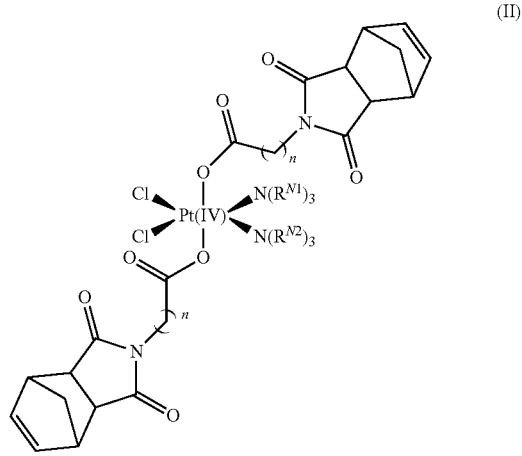

or a salt thereof.

3. The platinum complex of claim 1, wherein the complex is of Formula (II-a):

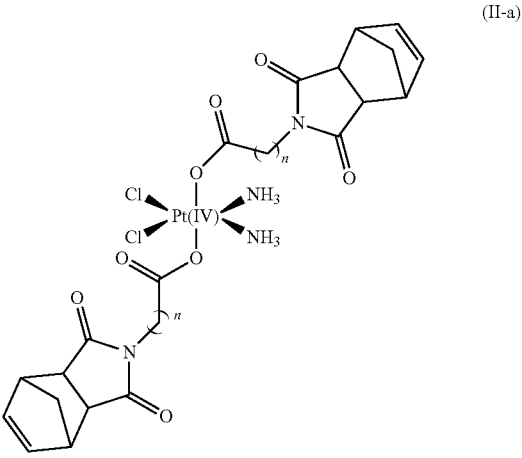

or a salt thereof.

4. The platinum complex of claim 1, wherein n is 1.
5. The platinum complex of claim 1, wherein n is 2.
6. The platinum complex of claim 1, wherein n is 3.
7. A method of preparing a platinum complex of claim 1, the method comprising steps of:
  (a) oxidizing a compound of Formula (s-1) with an oxidant

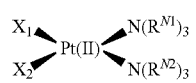

to give a compound of Formula (s-2):

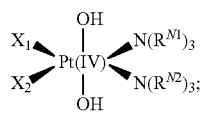

wherein:

$X_1$ is F, Cl, Br, or I;

$X_2$ is F, Cl, Br, or I;

each instance of $R^{N1}$ and $R^{N2}$ is independently hydrogen, optionally substituted $C_{1-6}$ alkyl, or a nitrogen protecting group; or two $R^{N1}$ are taken with the intervening atoms to form an optionally substituted heterocyclic ring; or two $R^{N2}$ are taken with the intervening atoms to form an optionally substituted heterocyclic ring; or $R^{N1}$ and $R^{N2}$ are taken with the intervening atoms to form an optionally substituted heterocyclic ring; and n is 1, 2, 3, 4, 5, or 6; and (b) coupling the compound of Formula (s-2) with a compound of Formula (s-3):

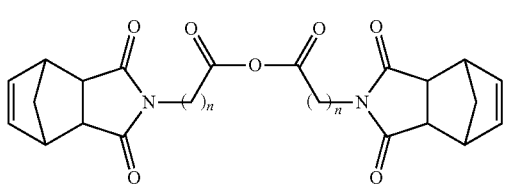

to yield a platinum complex of Formula (I).

8. The method of claim 7, wherein the oxidant used in step (a) is $H_2O_2$.

9. The method of claim 7, wherein an activator is present in step (b).

10. The method of claim 9, wherein the activator is N,N'-dicyclohexylcarbodiimide.

11. The platinum complex of claim 1, wherein each of $X_1$ and $X_2$ is Cl.

12. The platinum complex of claim 1, wherein each instance of $R^{N1}$ and $R^{N2}$ is independently hydrogen or optionally substituted $C_{1-6}$ alkyl.

13. The platinum complex of claim 1, wherein each instance of $R^{N1}$ and $R^{N2}$ is hydrogen.

14. The platinum complex of claim 1, wherein one $R^{N1}$ and one $R^{N2}$ are taken with the intervening atoms to form an optionally substituted heterocyclic ring.

15. The platinum complex of claim 1, wherein the platinum complex is of the formula:

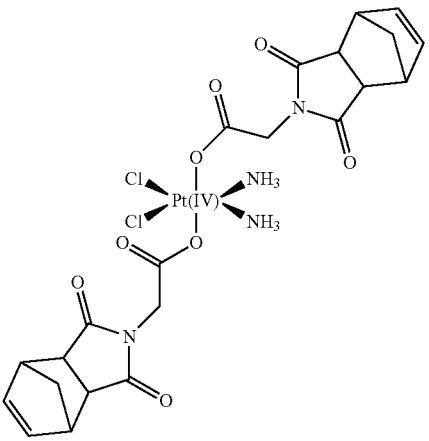

or a salt thereof.

16. The method of claim 7, wherein each of $X_1$ and $X_2$ is Cl.

17. The method of claim 7, wherein each instance of $R^{N1}$ and $R^{N2}$ is hydrogen.

18. The method of claim 7, wherein one $R^{N1}$ and one $R^{N2}$ are taken with the intervening atoms to form an optionally substituted heterocyclic ring.

19. The method of claim 7, wherein the platinum complex is of the formula:

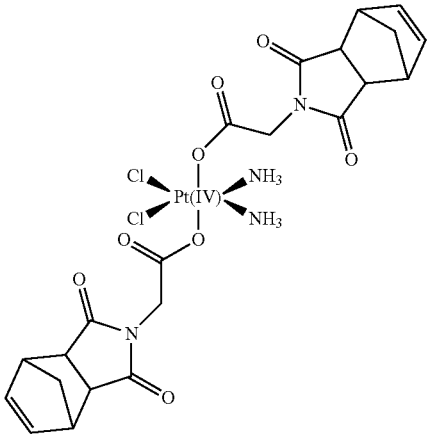

20. The method of claim 9, wherein the activator is 1-ethyl-3-(3-dimethylaminopropyl)carbodiimide hydrochloride, diphenylphosphorylazide, carbonyldiimidazole, diethylcyanophosphonate, benzotriazole-1-yloxy-trispyrrolidinophosphonium, benzotriazole-1-yloxy-trispyrrolidinophosphonium hexafluorophosphate, 1-hydroxybenzotriazole, hydroxysuccinimide, dimethylaminopyridine, 1-hydroxy-7-azabenzotriazole, hydroxyphthalimide, pentafluorophenol, 2-(1H-benzotriazole-1-yl)-1,1,3,3-tetramethyluronium hexafluorophosphate, 0-(7-azabenzotriazole-1-yl)-1,1,3,3-tetramethyluronium hexafluorophosphonate, 0-benzotriazole-1-yl-1,1,3,3-tetramethyluronium tetrafluoroborate, or 3,4-dihydro-3-hydrodi-4-oxa-1,2,3-benzotriazine.

* * * * *